(12) United States Patent
Sohn et al.

(10) Patent No.: US 9,550,997 B2
(45) Date of Patent: Jan. 24, 2017

(54) SCREENING OF ABUNDANTLY SECRETED PROTEINS AND THEIR USE AS FUSION PARTNERS FOR THE PRODUCTION OF RECOMBINANT PROTEINS

(75) Inventors: Jung-Hoon Sohn, Chungbuk (KR); Jung-Hoon Bae, Daejeon (KR); Hyun-Jin Kim, Ulsan (KR); Kwang-Mook Lim, Daejeon (KR)

(73) Assignee: Korean Research Institute of Bioscience and Biotechnology, Daejeon (KR)

( * ) Notice: Subject to any disclaimer, the term of this patent is extended or adjusted under 35 U.S.C. 154(b) by 660 days.

(21) Appl. No.: 12/631,449

(22) Filed: Dec. 4, 2009

(65) Prior Publication Data
US 2010/0159465 A1 Jun. 24, 2010

Related U.S. Application Data

(60) Provisional application No. 61/119,972, filed on Dec. 4, 2008.

(51) Int. Cl.
C12N 15/10 (2006.01)
C12P 21/02 (2006.01)
C12N 15/62 (2006.01)

(52) U.S. Cl.
CPC ......... *C12N 15/625* (2013.01); *C12N 15/1051* (2013.01); *C12P 21/02* (2013.01); *C07K 2319/02* (2013.01)

(58) Field of Classification Search
CPC ..... C12P 21/02; C12N 15/625; C12N 15/1051
See application file for complete search history.

(56) References Cited

U.S. PATENT DOCUMENTS

| | | |
|---|---|---|
| 5,037,760 A | 8/1991 | Smith et al. |
| 5,212,058 A | 5/1993 | Baker et al. |
| 5,362,644 A | 11/1994 | Boquet et al. |
| 5,536,637 A | 7/1996 | Jacobs |
| 5,547,871 A | 8/1996 | Black et al. |
| 5,563,046 A | 10/1996 | Mascarenhas et al. |
| 5,712,113 A | 1/1998 | Chung et al. |
| 5,952,171 A | 9/1999 | McCarthy et al. |
| 6,136,569 A | 10/2000 | Baker et al. |
| 6,150,098 A | 11/2000 | Zhang et al. |
| 6,228,590 B1 | 5/2001 | Baker |
| 6,548,633 B1 | 4/2003 | Edwards et al. |
| 7,029,842 B2 | 4/2006 | Duffner et al. |
| 2002/0127557 A1 | 9/2002 | Tan et al. |
| 2002/0160482 A1 | 10/2002 | Abrahmsen et al. |
| 2004/0110939 A1 | 6/2004 | Dumas Milne Edwards et al. |
| 2007/0275385 A1 | 11/2007 | Sohn et al. |
| 2009/0181425 A1 | 7/2009 | Sohn et al. |

FOREIGN PATENT DOCUMENTS

| | | |
|---|---|---|
| EP | 1 170 366 A1 | 1/2002 |
| EP | 0 907 727 B1 | 10/2002 |
| EP | 1 790 661 A2 | 5/2007 |
| JP | 2003-530106 A | 10/2003 |
| JP | 2008-521869 A | 6/2008 |
| WO | WO 97/40146 A1 | 10/1997 |
| WO | WO 99/49028 A1 | 9/1999 |
| WO | WO 01/00806 A2 | 1/2001 |
| WO | WO 01/77315 A1 | 10/2001 |
| WO | WO 02/057423 A2 | 7/2002 |
| WO | WO 02/072821 A2 | 9/2002 |
| WO | WO 2005/038024 A1 | 4/2005 |
| WO | WO 2005/068658 A1 | 7/2005 |
| WO | WO 2006/059106 A2 | 6/2006 |
| WO | WO 2007/012188 A1 | 2/2007 |
| WO | WO 2007/015178 A2 | 2/2007 |
| WO | WO 2007/035930 A2 | 3/2007 |

OTHER PUBLICATIONS

Baldari, C., et al., "Differential stability of human interleukin 1 beta fragments expressed in yeast," Protein Eng. 1:433-437, JRL Press Limited, England (1987).

Broekhuijsen, M.P., et al., "Secretion of heterologous proteins by *Aspergillus niger*: Production of active human interleukin-6 in a protease-deficient mutant by KEX2-like processing of a glucoamylase-hIL6 fusion protein," *J Biotechnol.* 31:135-145, Elsevier Science Publishers B.V., Netherlands (Nov. 1993).

Contreras, R., et al., "Efficient KEX2-like Processing of a Glucoamylase-Interleukin-6 Fusion Protein by *Aspergillus Nidulans* and Secretion of Mature Interleukin-6," *Bio/Technology (N.Y.)* 9:378-381, Nature Pub. Co., United States (Apr. 1991).

Crosier, P.S., et al., "In Situ Hybridization Screen in Zebrafish for the Selection of Genes Encoding Secreted Proteins," *Developmental Dynamics* 222:637-644, Wiley-Liss, Inc., United States (2001).

Dorner, A.J., et al., "Overexpression of GRP78 mitigates stress induction of glucose regulated proteins and blocks secretion of selective proteins in Chinese hamster ovary cells," *The EMBO Journal* 11:1563-1571, Oxford University Press, England (1992).

Dorner, A.J., et al., "Reduction of Endogenous GRP78 Levels Improves Secretion of a Heterologous Protein in CHO Cells," *Molecular and Cellular Biology* 8:4063-4070, American Society for Microbiology, United States (1988).

Downing, K.J., et al., *Staphylococcus aureus* nuclease is a useful secretion reporter for mycobacteria, *Gene* 239:293-299, Elscience Science B.V., Netherlands (1999).

Eckart, M.R. and Bussineau, C.M., "Quality and authenticity of heterologous proteins synthesized in yeast," *Curr. Opin. Biotechnol.* 7:525-530, Current Biology Ltd., England (Oct. 1996).

Ferguson, D.A., et al., "Selective Identification of Secreted and Transmembrane Breast Cancer Markers using *Escherichia coli* Ampicillin Secretion Trap," *Cancer Res* 65:8209-8217, American Association for Cancer Research, United States (2005).

Galliciotti, G., et al., "Signal-sequence Trap in Mammalian and Yeast Cells: A Comparison," *J. Membrane Biol.* 183:175-182, Springer-Verlag, United States (2001).

(Continued)

*Primary Examiner* — Nancy Treptow
(74) *Attorney, Agent, or Firm* — Sterne, Kessler, Goldstein & Fox P.L.L.C.

(57) ABSTRACT

The present invention relates techniques for identifying suitable secretion fusion partner (SFP) for hyper-secretory production of recombinant proteins. The SFPs can be obtained from secretome analyzes. Recombinant proteins are produced in a fusion form with a secretion fusion partner (SFP) and can be separated from the SFP by in vitro protease treatment. SFPs of this invention greatly improve the secretion level of target proteins and peptides which are valuable for bio-pharmaceuticals and the bio-industry.

12 Claims, 29 Drawing Sheets

(56) References Cited

OTHER PUBLICATIONS

Goo, J.H., et al., "Selection of Arabidopsis genes encoding secreted and plasma membrane proteins," *Plant Molecular Biology* 41:415-423, Kluwer Academic Publishers, Netherlands (1999).
Gouka, R.J., et al., "Efficient production of secreted proteins by Aspergillus: progress, limitations and prospects," *Appl. Microbiol. Biotechnol.* 47:1-11, Springer-Verlag, Germany (Jan. 1997).
Harmsen, M.M., et al., "Overexpression of binding protein and disruption of the PMR1 gene synergistically stimulate secretion of bovine prochymosin but not plant Thaumatin in yeast," *Appl Microbiol Biotechnol.* 46:365-370, Springer-Verlag, Germany (Nov. 1996).
Hayano, T., et al., "Protein disulfide isomerase mutant lacking its isomerase activity accelerates protein folding in the cell," *FEBS Lett.* 377:505-511, Federation of European Biochemical Societies, Netherlands (Dec. 1995).
Hsu, T.-A., et al., "Effects of Co-expressing Chaperone BiP on Functional Antibody Production in the Baculovirus System," *Protein Expr Purif.* 5:595-603, Academic Press, Inc., United States (Dec. 1994).
Jacobs, K.A., et al., "A genetic selection for isolating cDNAs encoding secreted proteins," *Gene* 198:289-296, Elsevier Science B.V., Netherlands (1997).
Jeenes, D.J., et al., "A truncated glucoamylase gene fusion for heterologous protein secretion from *Aspergillus niger*," *FEMS Microbiol Lett.* 107:267-272, Federation of European Microbiological Societies, Netherlands (Mar. 1993).
Kjeldsen, T., et al., "Prepro-Leaders Lacking N-linked Glycosylation for Secretory Expression in the Yeast *Saccharomyces cerevisiae*," *Protein Expr Purif.* 14:309-316, Academic Press, United States (Dec. 1998).
Kjeldsen, T., et al., "Synthetic Leaders with Potential BiP Binding Mediate High-Yield Secretion of Correctly Folded Insulin Precursors from *Saccharomyces cerevisiae*," *Protein Expr Purif.* 9:331-336, Academic Press, United States (Apr. 1997).
Klein, R.D., et al., "Selection for genes encoding secreted proteins and receptors," *Proc. Natl. Acad. Sci. USA* 93:7108-7113, National Academy of Sciences, United States (Jul. 1996).
Lee, J., et al., "Novel Secretion System of a Recombinant *Saccharomyces cerevisiae* Using an N-terminus Residue of Human IL-1β as Secretion Enhancer," *Biotechnol. Prog.* 15:884-890, American Chemical Society and American Institute of Chemical Engineers, United States (1999).
Lim, E.M., et al., "Identification of *Mycobacterium tuberculosis* DNA Sequences Encoding Exported Proteins by Using phoA Gene Fusions," *J. Bacteriol.* 177:59-65, American Society for Microbiology, United States (Jan. 1995).
MacConaill, L.E., et al., Investigation of Protein Export in *Bifidobacterium breve* UCC2003, *Appl. Environ. Microbiol.* 69:6994-7001, American Society for Microbiology, United States (Dec. 2003).
Makrides, S.C., "Strategies for Achieving High-Level Expression of Genes in *Escherichia coli*," *Microbiological Reviews* 60:512-538, American Society for Microbiology, United States (1996).
Monteoliva, L., et al., "Large-Scale Identification of Putative Exported Proteins in *Candida albicans* by Genetic Selection," *Eukaryotic Cell* 1:514-525, American Society for Microbiology, United States (Aug. 2002).
Muesch, A., et al., "A novel pathway for secretory proteins?" *TIBS* 15:86-88, Elsevier Science Publishers Ltd., United Kingdom (Mar. 1990).
Roberts, I.N., et al., "Heterologous gene expression in *Aspergillus niger*: a glucoamylase-porcine pancreatic prophospholipase $A_2$ fusion protein is secreted and processed to yield mature enzyme," *Gene* 122:155-161, Elsevier Science Publishers B.V., Netherlands (Dec. 1992).

Robinson, A.S., et al., "Protein Disulfide Isomerase Overexpression Increases Secretion of Foreign Proteins in *Saccharomyces cerevisiae*," *Bio/Technology* (NY) 12:381-384, Nature Pub. Co., United States (Apr. 1994).
Robinson, A.S., et al., "Reduction of BiP Levels Decreases Heterologous Protein Secretion in *Saccharomyces cerevisiae*," *J. Biol. Chem.* 271:10017-10022, American Society for Biochemistry and Molecular Biology, United States (1996).
Sagt, C.M.J., et al., "Introduction of an N-Glycosylation Site Increases Secretion of Heterologous Proteins in Yeasts," *Applied and Environmental Microbiology* 66:4940-4944, American Society for Microbiology, United States (2000).
Schultz, L.D., et al., "Using Molecular Genetics to Improve the Production of Recombinant Proteins by the Yeast *Saccharomyces cerevisiae*," *Ann NY Acad Sci.* 721:148-157, New York Academy of Sciences, United States (May 1994).
Surpili, M.J., et al., "A yeast-based model system for cloning secreted and membrane proteins," *An Acad Bras Cienc* 74:599-608, Academia Brasileira De Ciencias, Brasil (2002).
Takahashi, S., et al., "Function of the prosequence for in vivo folding and secretion of active *Rhizopus otyzae* lipase in *Saccharomyces cerevisiae*," *Appl Microbiol Biotechnol.* 55:454-462, Springer Verlag, Germany (May 2001).
Tan, N. S., et al., "Engineering a novel secretion signal for cross-host recombinant protein expression," *Protein Eng.* 15:337-345, Oxford University Press, England (2002).
Wang, H. and Ward, M., "Molecular characterization of a PDI-related gene prpA in *Aspergillus niger* var. *awamori*," *Curr Genet* 37:57-64, Springer-Verlag, Germany (Jan. 2000).
Ward, P.P., et al., "A system for production of commercial quantities of human lactoferrin: a broad spectrum natural antibiotic," *Bio/Technology* (NY). 13:498-503, Nature Pub. Co., United States (May 1995).
Ward, M., et al.,"Improved Production of Chymosin in Aspergillus by Expression as a Glucoamylase-Chymosin Fusion," *Bio/Technology* 8:435-440, Nature Pub. Co., United States (1990).
International Search Report for International Appl. No. PCT/KR2004/003517, Korean Intellectual Property Office, mailed Apr. 7, 2005.
International Search Report for International Appl. No. PCT/IB2006/003102 (listed as FP9), Korean Intellectual Property Office, mailed Mar. 30, 2003.
Supplementary European Search Report for European Application No. 08887601.7, European Patent Office, The Hague, Netherlands, completed Feb. 21, 2012.
English language Abstract of Japanese Patent Application No. JO 2008-263975 A, Japanese Patent Office, Patent & Utility Gazette DB, Patent Abstract of Japan (2010).
Langella, P. and Leloir, Y., "Heterologous protein secretion in *Lactococcus lactis*; a novel antigen delivery system," *Braz. J. Med. Biol. Res.* 32:191-198, Associação Brasileira de Divulgação Cientifica, Brazil (1999).
Sohn, J., et al., "Human IL-2 secretion, TFP SEQ ID No. 29," in WO 2007/015178 A2, Accession No. AEX30558 (2007).
Sohn, J., et al., "Human IL-2 secretion, TFP SEQ ID No. 175," in WO 2007/015178 A2, Accession No. AEX30704 (2007).
Sahara, T., et al., "Secretory signal peptide, TFP SEQ ID No. 777," in US 2007/117186 A1, Accession No. ANN52858 (2007).
Nakajima, H., et al., "Expression of an 87-kD-β-1, 3-Glucanase of *Bacillus circulans* IAM1165 in *Saccharomyces cerevisiae* by Low-temperature Incubation," *Biosci. Biotech. Biochem.* 57:2039-2042, Japan Society for Bioscience, Biotechnology, and Agrochemistry, Japan (1993).
Extended European Search Report for European Application No. 12187155.2, European Patent Office, The Hague, Netherlands, completed May 14, 2013.
Unverified Machine Translation of Japanese Patent Application No. JP 2003-530106 A, Japanese Patent Office, Patent & Utility Model Gazette DB (listed as document FP15 on the accompanying form PTO/SB/08A).
VOA1_Yeast, Accession number: P53262, UniProtKB/Swiss-Prot, last updated Oct. 1, 1996 (10 pages), accessed on Sep. 14, 2015.

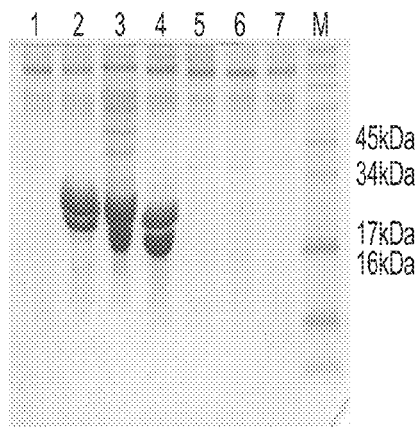

SCREENING OF ABUNDANTLY SECRETED PROTEINS AND THEIR USE AS FUSION PARTNERS FOR THE PRODUCTION OF RECOMBINANT PROTEINS

This application claims priority to U.S. Provisional Appl. No. 61/119,972, filed on Dec. 4, 2008, the entire contents of which are hereby incorporated by reference in their entirety.

REFERENCE TO A SEQUENCE LISTING SUBMITTED ELECTRONICALLY VIA EFS-WEB

The content of the electronically submitted sequence listing (Name: 2472_0030001_SubstituteSequenceListing_ascii.txt, Size: 91,872 bytes; and Date of Creation: Oct. 18, 2012) filed herewith with the application is incorporated by reference in its entirety.

BACKGROUND OF THE INVENTION

Field of the Invention

This invention is in the field of recombinant protein expression. In particular, the invention relates to secretion fusion partners (SFPs) and techniques for screening for suitable SFPs. Optimized SFPs for accomplishing high level secretion of target polypeptides are described. The SFPs of the invention are capable of inducing hyper-secretory production of recombinant proteins.

Related Art

The recombinant expression of proteins of interest is a widely used procedure to produce large quantities of proteins for research purposes or for therapeutic and other commercial uses. A variety of recombinant expression systems are known in the art, including bacterial, yeast, and mammalian host cell systems, and many different proteins have been successfully produced in these systems. However, there are also many proteins that are not easily produced using available expression systems, resulting in little or no protein expression and secretion. Methods for improving the secretion of recombinantly expressed proteins, such as overexpression of molecular chaperones and foldase (Hackel et al., *Pharm Res* 23:790 (2006); Poewer and Robinson, *Biotechnol Prog* 23: 364 (2007); Shusta et al., *Nat Biotechnol* 16: 773 (1998)), over-expression of genes related to the secretory pathway ((Carla Fama et al., *Biochim Biophys Acta* 1773: 232 (2007); Wentz and Shusta et al., *Appl Environ Microbiol* 73: 1189 (1998)), engineering of the leader sequence (Clements et al., *Gene* 106: 267 (1991); Kjaerulff and Jensen, *Biochem Biophys Res Commun* 336: 974 (2005); Sagiya et al., *Microbiol. Biotechnol* 42: 358 (1994); Li et al., *Bitechnol Prog* 18: 831 (2002)) have had some success with particular proteins of interest.

Another way of increasing protein productivity is to link the protein of interest to a fusion partner. Secretory proteins used as a fusion partners, including, human serum albumin (Kang et al., *Protein Expr Purif* 53: 331 (2007); Huang et al., *J. Pept. Sci* 14: 588 (2008)), alpha-lactalbumin (WO1995027782A1), rubredoxin (WO2000039310A1), human glucagon (WO2000053777A1), cathelicidin-related peptide derived from the hagfish (WO2005019242A2), phosphoribulokinase (US6500647B1), protein disulfide isomerase (Kajino et al., *Appl Environ Microbiol* 66: 638 (2000), Staphylococcal Protein A (Moreno et al., *Protein Expr Purif* 18: 242 (2000), Hsp150 protein (Sievi et al., *Biotechnol. Prog.* 19: 1368 (2003), cellulose-binding domain (Ahn et al., *Appl Microbiol Biotechnol.* 64: 833 (2004)) and gold binding peptide (US20050106625A1) have had some success with particular proteins of interest.

In an effort to identify secreted proteins and novel signal sequences, several signal sequence trap systems have been developed. U.S. Pat. No. 6,228,590 describes a technique for screening for mammalian signal sequences by transforming reporter protein-deficient yeast with nucleic acids comprising mammalian coding sequences fused to a reporter protein and detecting cells that secrete the reporter protein. A similar system using invertase-deficient yeast and an invertase reporter protein is disclosed in EP0907727. Yeast-based signal sequence traps have been used to identify secreted proteins from human DNA (Klein et al., *Proc. Natl. Acad. Sci. USA* 93:7108 (1996); Jacobs et al., *Gene* 198:289 (1997)), mouse DNA (Gallicioti et al., *J. Membrane Biol.* 183:175 (2001)), zebrafish DNA (Crosier et al., *Dev. Dynamics* 222:637 (2001)), *Arabidopsis* DNA (Goo et al., *Plant Mol. Biol.* 41:415 (1999)), potato DNA (Surpili et al., *Anais de Academia Brasileira de Ciencias* 74:599 (2002)), and *Candida albicans* DNA (Monteoliva et al., *Eukaryotic Cell* 1:514 (2002)). Similar trap systems have been developed using mammalian host cells (Gallicioti et al., *J. Membrane Biol.* 183:175 (2001)) and bacterial host cells (Ferguson et al., *Cancer Res.* 65:8209 (2000). Reporter proteins that have been used in signal sequence traps include invertase (Klein et al., *Proc. Natl. Acad. Sci. USA* 93:7108 (1996)), alpha amylase (U.S. Pat. No. 6,228,590), acid phosphatase (PHO5) (Surpili et al., *Anais de Academia Brasileira de Ciencias* 74:599 (2002)), and β-lactamase Ferguson et al., *Cancer Res.* 65:8209 (2000).

A method for identifying translational fusion partners (TFPs) useful for secretion of a target protein is disclosed in WO 2005/068658. The method comprises (i) obtaining a plurality of host cells transformed with a variety of vectors comprising a library of nucleic acid fragments and a target protein-encoding nucleotide sequence fused with a reporter protein-encoding nucleotide sequence, wherein the host cells are deficient in the reporter protein, and (ii) identifying a TFP library from the host cells, wherein the TFP library comprises nucleic acid fragments which individually induce the secretion of the target protein.

Translational fusion partner (TFP) technology for secretory production of rarely secretable proteins in yeast was described in WO 2007/015178. In the course of TFP screening from the yeast genome, the YGR106C (Voa1p) gene was discovered. The cellular location of Voa1p protein was recently identified in the ER membrane (Ryan et al., Mol. Biol. Cell, Epub ahead of print, Sep. 17, 2008). Voa1p was proposed to be one of five V0 assembly factors for vacuolar ATPase.

There remains a need in the art for additional sequences that enhance expression of proteins, and methods for identifying such sequences.

SUMMARY OF THE INVENTION

The present invention relates to hyper-secretory production and efficient purification of various recombinant proteins using secretion fusion partners (SFPs), which can be obtained by secretome analysis. Recombinant proteins are extracellularly produced in a fusion form with a secretion fusion partner and can be separated from the SFP by in vitro protease treatment. SFPs described in this invention greatly improve the secretion level of target proteins and polypeptides which are valuable for bio-pharmaceuticals and the bio-industry. Methods for selection/screening of SFPs are also described. Although it is possible to determine or even predict whether a particular protein is secreted, it is not possible to predict whether a secreted protein will act as a SFP. The selection/screening method of the invention allows the selection of proteins, and fragments and derivatives of such proteins, that act as SFPs. The SFPs selected by the present method of screening/selection enhance the recombinant production of proteins that are useful in bio-pharmaceuticals and the bio-industry. Also included in the invention are SFPs and fragments and derivatives thereof that have been identified.

BRIEF DESCRIPTION OF THE DRAWINGS/FIGURES

The above and other objects, features and advantages of the present invention will be more clearly understood from the following detailed description taken in conjunction with the accompanying drawings.

FIG. 1 shows (A) the predicted amino sequence and domain of SFP1 protein (SEQ ID NO:1), (B) a schematic diagram of vectors expressing serially deleted SFP1 genes, (C) SDS-PAGE analysis of relative SFP1 protein expression levels. 10% Tris-Tricine SDS-PAGE analysis of 0.6 ml of each culture broth concentrated with 0.4 ml of acetone. Lane 1: Culture broth of 2805 strain transformed with YGaT91 vector; Lane 2: Culture broth of 2805 strain transformed with YGaT92 vector; Lane 3: Culture broth of 2805 strain transformed with YGaT93 vector; Lane 4: Culture broth of 2805 strain transformed with YGaT94 vector; Lane 5: Culture broth of 2805 strain transformed with YGaT95 vector; Lane 6: Culture broth of 2805 strain transformed with YGaT96 vector; Lane 7: Culture broth of 2805 strain transformed with YGaT97 vector; Lane M: Pre-stained protein size marker (Invitrogen).

FIG. 2 shows (A) a schematic diagram of vectors expressing SFP1-IL2 fusion proteins, (B) SDS-PAGE analysis of SFP1-IL2 fusion protein expression levels. 10% Tris-Tricine SDS-PAGE analysis of 0.6 ml of each culture broth concentrated with 0.4 ml of acetone. Lane 1: Culture broth of 2805 strain transformed with YGaT92-IL2 vector; Lane 2: Culture broth of 2805 strain transformed with YGaT93-IL2 vector; Lane 3: Culture broth of 2805 strain transformed with YGaT94-IL2 vector; Lane M: Pre-stained protein size marker (Invitrogen).

FIG. 3 illustrates (A) a profile for fed-batch fermentation of a recombinant yeast strain containing YGaT92-EXD4 and (B) the results of SDS-PAGE for analyzing proteins secreted into the medium according to fermentation time.

FIG. 4 shows SDS-PAGE analysis of purified SFP1-EXD4 fusion protein digested with different concentrations of enterokinase (Invitrogen, USA). Lane 1: Purified SFP1-EXD4 fusion protein; Lane 2: Purified SFP1-EXD4 fusion protein digested with 0.1 µl of enterokinase for 1 hr at 37° C.; Lane 3: Purified SFP1-EXD4 fusion protein digested with 0.2 µl of enterokinase for 1 hr at 37° C.; Lane 4: Purified SFP1-EXD4 fusion protein digested with 0.3 µl of enterokinase for 1 hr at 37° C.; Lane M: Pre-stained protein size marker (Invitrogen).

FIG. 7 shows (A) a schematic diagram of vectors expressing SFP1 variants-EXD4 fusion proteins, (B) SDS-PAGE analysis of SFP1 variants—EXD4 fusion protein expression levels. 10% Tris-Tricine SDS-PAGE analysis of 0.6 ml of each culture broth concentrated with 0.4 ml of acetone. Lane 1: Culture broth of 2805 strain transformed with YGaT92-EXD4 vector; Lane 2: Culture broth of 2805 strain transformed with YGaT921-EXD4 vector; Lane 3: Culture broth of 2805 strain transformed with YGaT922-EXD4 vector; Lane 4: Culture broth of 2805 strain transformed with YGaT923-EXD4 vector; Lane M: Pre-stained protein size marker (Invitrogen).

Figure 8:
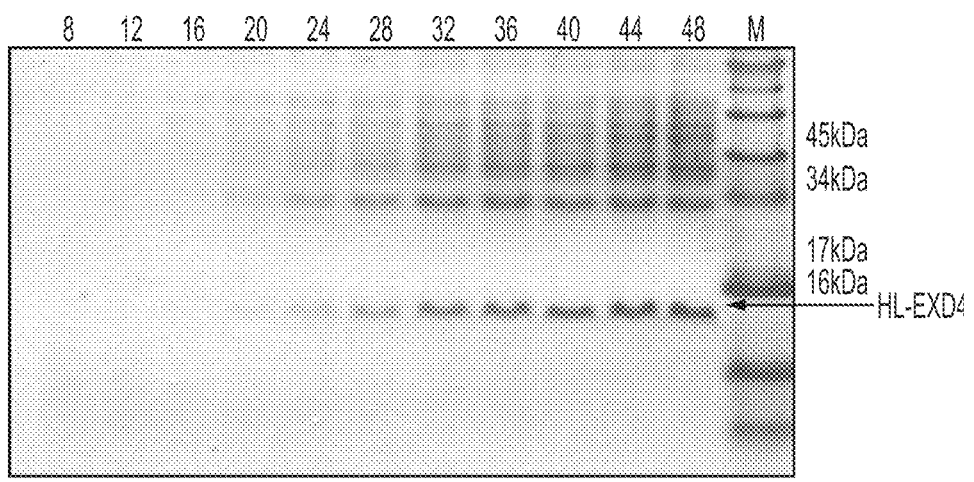

FIG. 8 shows SDS-PAGE analysis of fed-batch fermentation of a recombinant yeast strain containing YGaMKH-EXD4 at the indicated fermentation time.

Figure 9A:
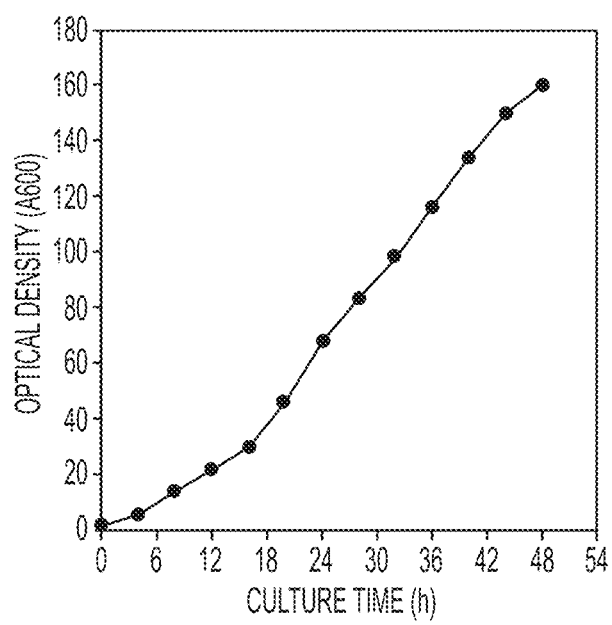
Figure 9B:
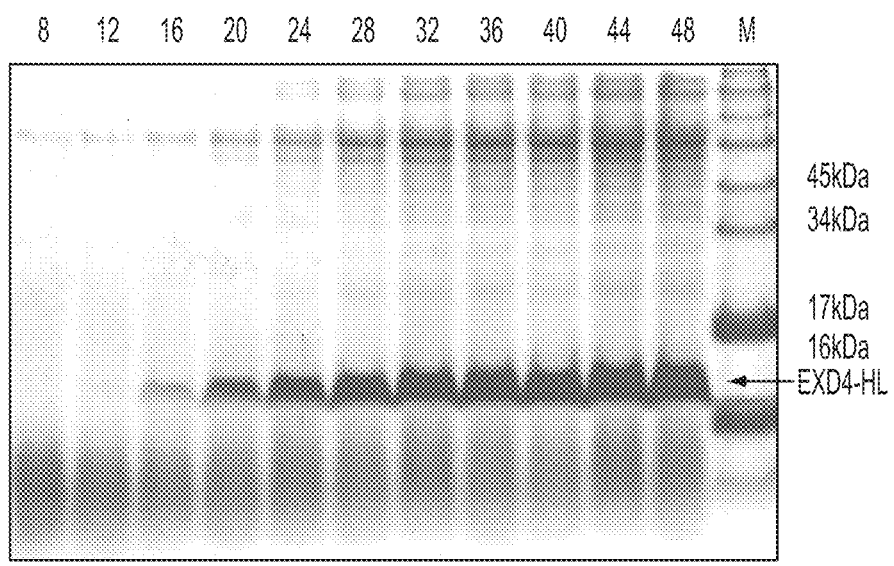

FIG. 9 illustrates (A) a profile for fed-batch fermentation of a recombinant yeast strain containing YGaST6-EXD4-HL and (B) the results of SDS-PAGE for analyzing proteins secreted into the medium according to fermentation time.

Figure 10A:
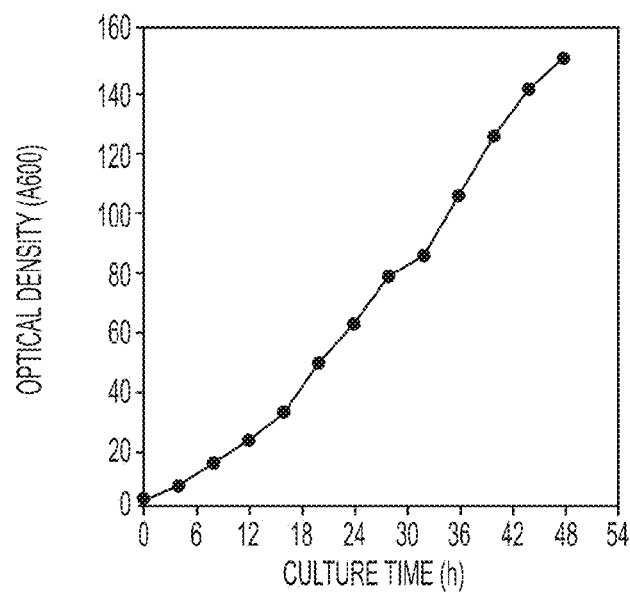
Figure 10B:
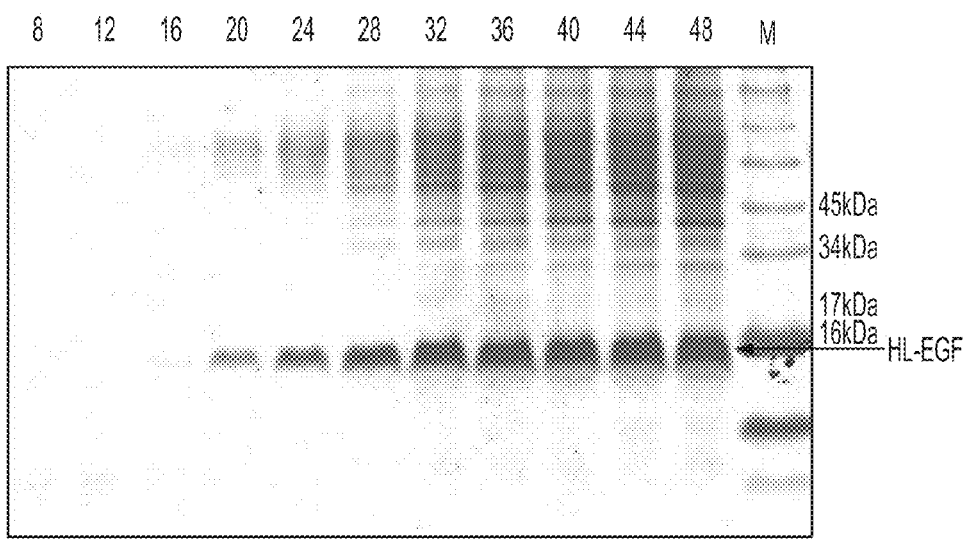

FIG. 10 shows (A) a profile for fed-batch fermentation of a recombinant yeast strain containing YGaMKH-EGF and (B) the results of SDS-PAGE for analyzing proteins secreted into the medium according to fermentation time.

FIG. 11 shows (A) the result of Ni-NTA affinity chromatography of HL-EGF fusion protein. The patched drawing is the SDS-PAGE analysis of indicated fractions and (B) the result of Ni-NTA affinity chromatography of HL-EGF fusion protein after digestion with enterokinase. The patched drawing is the SDS-PAGE analysis of indicated fractions.

Figure 12A:
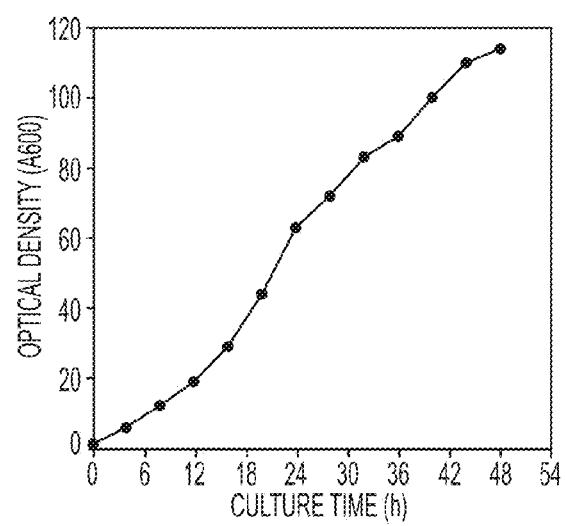
Figure 12B:
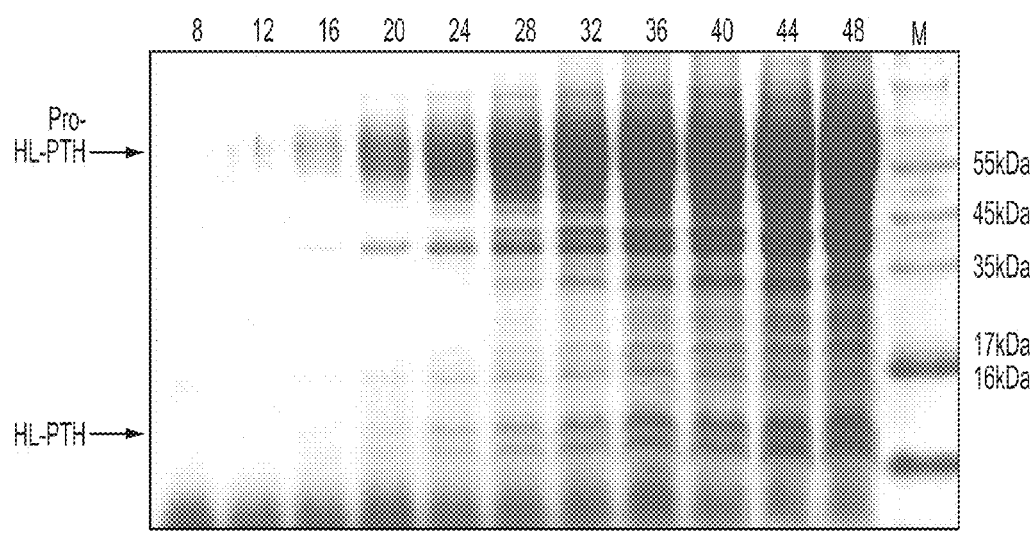

FIG. 12 illustrates (A) a profile for fed-batch fermentation of a recombinant yeast strain containing YGaMKH-PTH and (B) the results of SDS-PAGE for analyzing proteins secreted into the medium according to fermentation time.

Figure 13:
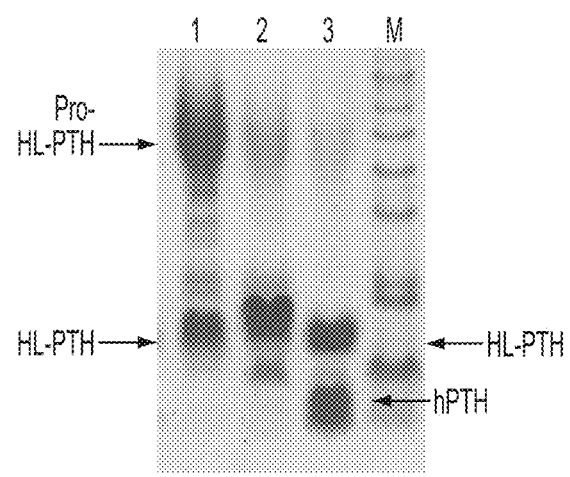

FIG. 13 shows SDS-PAGE analysis of purified HL-PTH fusion protein digested with secretion form of recombinant Kex2p (J H Sohn, KRIBB) and enterokinase (Invitrogen, USA). Lane 1: Purified HL-PTH fusion protein; Lane 2: Purified HL-PTH fusion protein digested with Kex2p for 1 hr at 37° C.; Lane 3: Purified HL-PTH fusion protein digested with enterokinase for 1 hr at 37° C.; Lane M: Pre-stained protein size marker (Invitrogen).

Figure 14A:
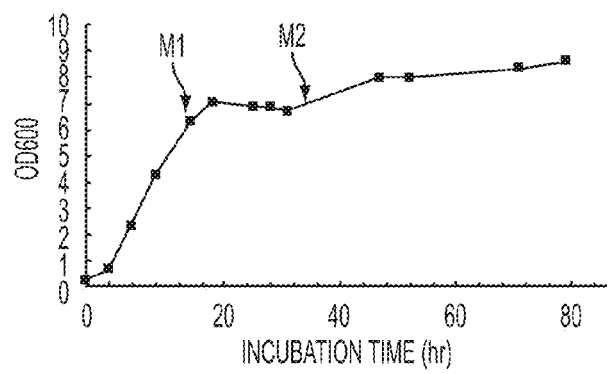
Figure 14B:
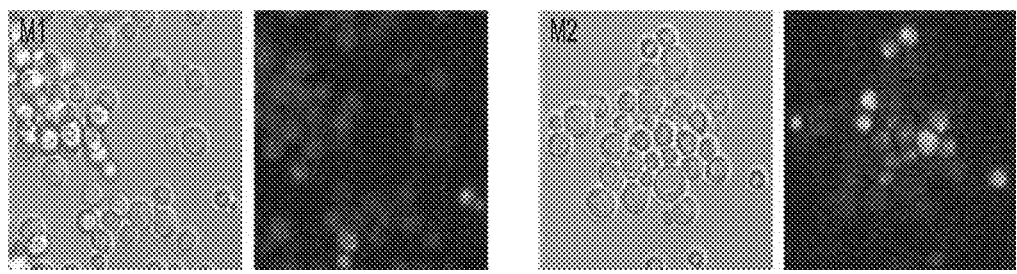

FIG. 14 shows (A) the growth curve of 2805 strain and arrows indicate the sampling points, (B) the confocal laser scanning microscope of sampled cells after staining with a fluorescent dye hochest.

Figure 15:
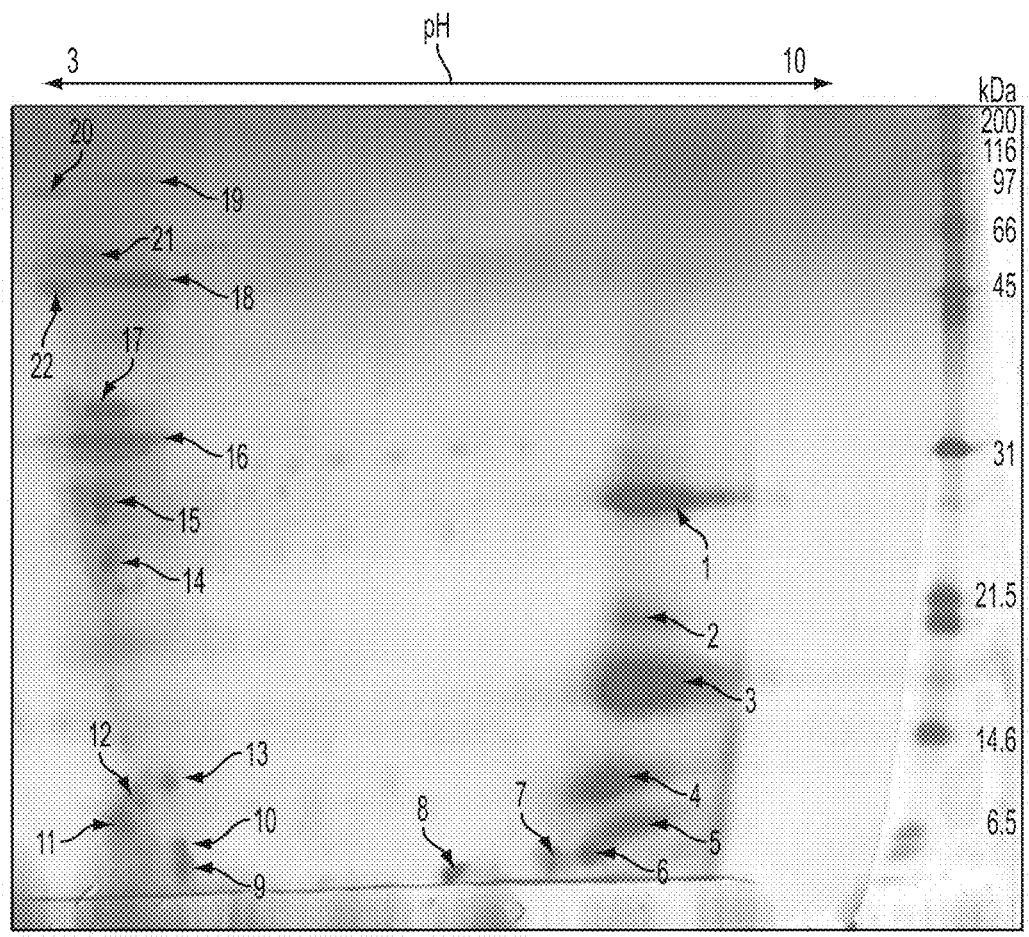

FIG. 15 shows the results of 2D gel electrophoresis of M2 sample.

Figure 16:
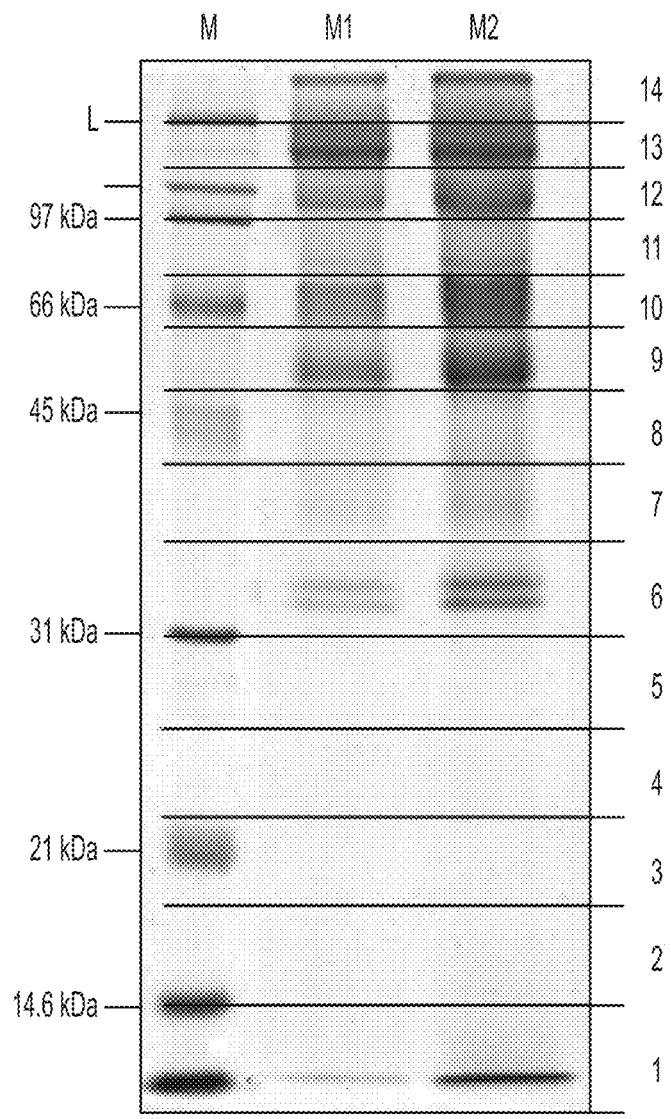

FIG. 16 shows SDS-PAGE analysis for 1-DE/MudPIT (Multidimensional Protein Identification Technology).

FIG. 17 shows (A) SDS-PAGE analysis of culture supernatant of Y2805 transformants expressing 19 genes selected from secretome analyses. 10% Tris-Glycine SDS-PAGE analysis of 0.6 ml of each culture broth concentrated with 0.4 ml of acetone. Lane 1: Culture broth of 2805 strain over-expressing BGL2 gene; Lane 2: Culture broth of 2805 strain over-expressing CIS3; Lane 3: Culture broth of 2805 strain over-expressing CRH1; Lane 4: Culture broth of 2805 strain over-expressing CWP1; Lane 5: Culture broth of 2805 strain over-expressing DSE4; Lane 7: Culture broth of 2805 strain over-expressing EGT2; Lane 8: Culture broth of 2805 strain over-expressing EXG1; Lane 9: Culture broth of 2805 strain over-expressing GAS1; Lane 10: Culture broth of 2805 strain over-expressing GAS3; Lane 11: Culture broth of 2805 strain over-expressing GAS5; Lane 12: Culture broth of 2805 strain over-expressing PST1; Lane 13: Culture broth of 2805 strain over-expressing SCW4; Lane 15: Culture broth of 2805 strain over-expressing SIM1; Lane 16: Culture broth of 2805 strain over-expressing TOS1; Lane 17: Culture broth of 2805 strain over-expressing UTH1; Lane 18: Culture broth of 2805 strain over-expressing YGP1; Lane 19: Culture broth of 2805 strain over-expressing YPS1; Lane 20: Culture broth of 2805 strain over-expressing ZPS1; Lane M: Pre-stained protein size marker (Invitrogen). (B) SDS-PAGE analysis of culture supernatant after Endo-H treatment.

Figure 18:
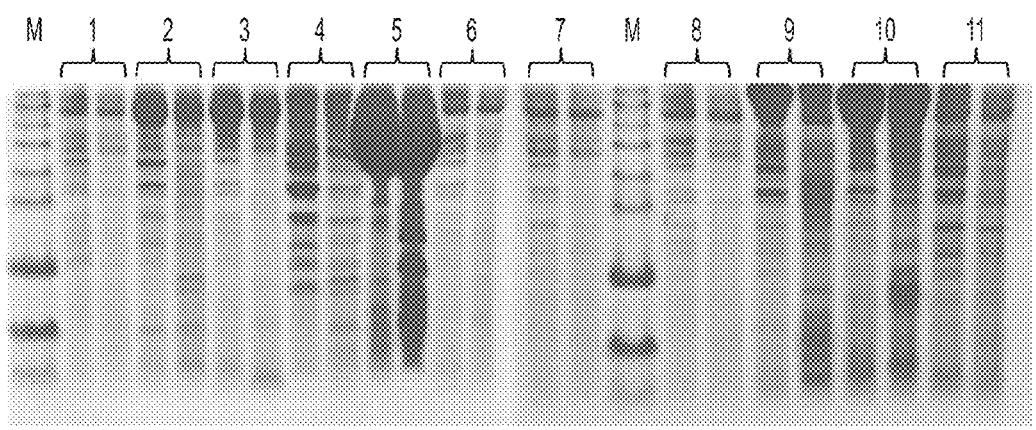

FIG. 18 shows SDS-PAGE analysis of culture supernatant of Y2805 transformants expressing 11 genes fused with EXD4 gene, respectively. 10% Tris-Tricine SDS-PAGE analysis of 0.6 ml of each culture broth concentrated with 0.4 ml of acetone. Lane 1: Culture broth of 2805 strain over-expressing BGL2-EXD4 gene; Lane 2: Culture broth of 2805 strain over-expressing GAS3-EXD4; Lane 3: Culture broth of 2805 strain over-expressing GAS5-EXD4; Lane 4: Culture broth of 2805 strain over-expressing PST1-EXD4; Lane 5: Culture broth of 2805 strain over-expressing SCW4-EXD4; Lane 6: Culture broth of 2805 strain over-expressing SCW10-EXD4; Lane 7: Culture broth of 2805 strain over-expressing SIM1-EXD4; Lane 8: Culture broth of 2805 strain over-expressing UTH1-EXD4; Lane 9: Culture broth of 2805 strain over-expressing YGP1-EXD4; Lane 10: Culture broth of 2805 strain over-expressing YPS1-EXD4; Lane 11: Culture broth of 2805 strain over-expressing ZPS1-EXD4; Lane M: Pre-stained protein size marker (Invitrogen).

FIG. 19 shows (A) Kyte-Doolittle hydropathy analysis and schematic drawing for the deletion fragments of SCW4 and EXD4 fusion, (B) SDS-PAGE analysis of culture supernatants of each transformant containing gradually deleted SCW4-EXD4 fusion fragments.

Figure 20A:
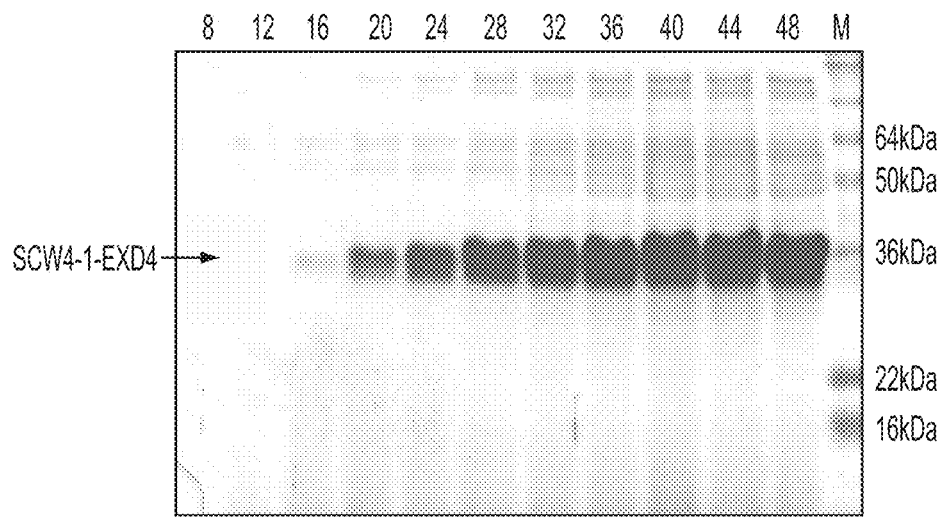
Figure 20B:
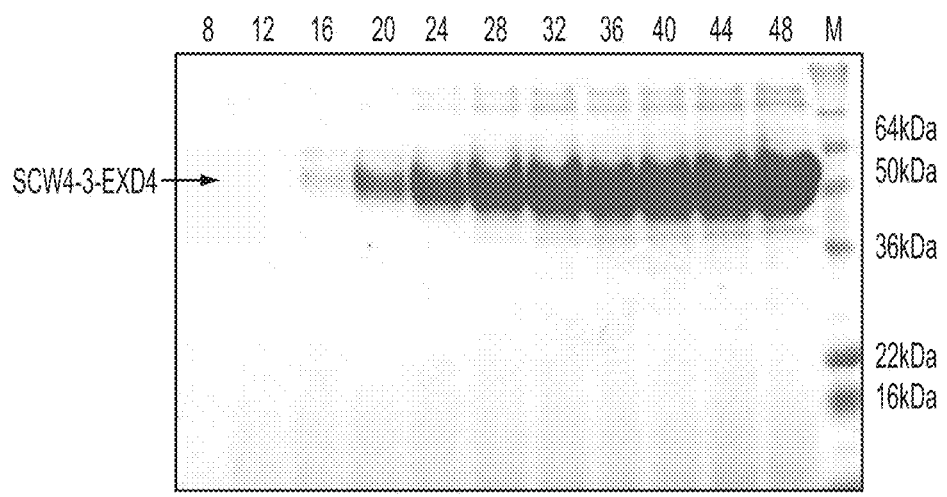

FIG. 20 shows the results of SDS-PAGE for analyzing proteins secreted into the medium during fed-batch fermentation of a recombinant 2805 yeast strain containing YGa-SCW4-1-EXD4 and YGa-SCW4-3-EXD4, respectively.

Figure 21:
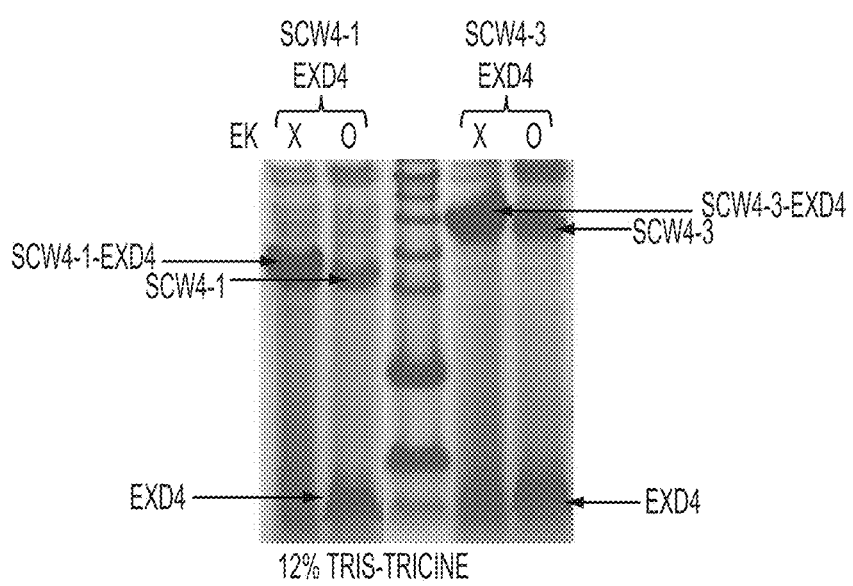

FIG. 21 shows the results of SDS-PAGE for analyzing the secreted fusion proteins, SCW4-1-EXD4 and SCW4-3-EXD4 before and after treatment of enterokinase.

FIG. 22 shows the results of SDS-PAGE of secreted SCW4-hGH into the medium (A) culture broth 10 microliter of cells containing each vector, (B) samples before and after treatment of enterokinase.

Figure 23:
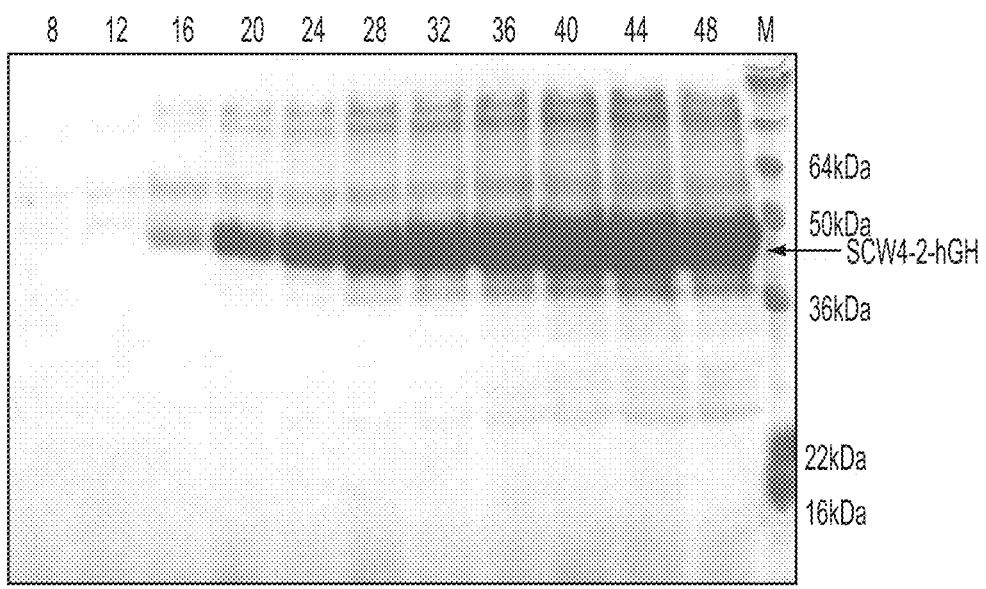

FIG. 23 shows the results of SDS-PAGE for analyzing proteins secreted into the medium during fed-batch fermentation of a recombinant yeast strain containing YGa-SCW4-2-hGH according to fermentation time.

Figure 24:
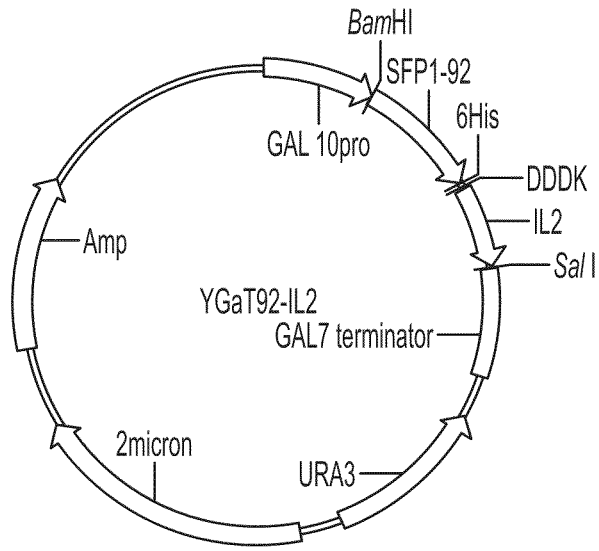

FIG. 24 shows a map of IL-2 expression vector pYGaT92-IL2.

Figure 25:
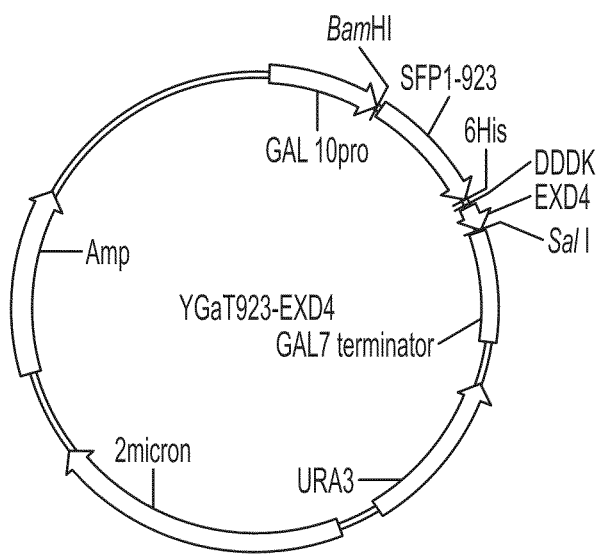

FIG. 25 shows a map of exendin-4 expression vector pYGaT923-EXD4.

Figure 26:
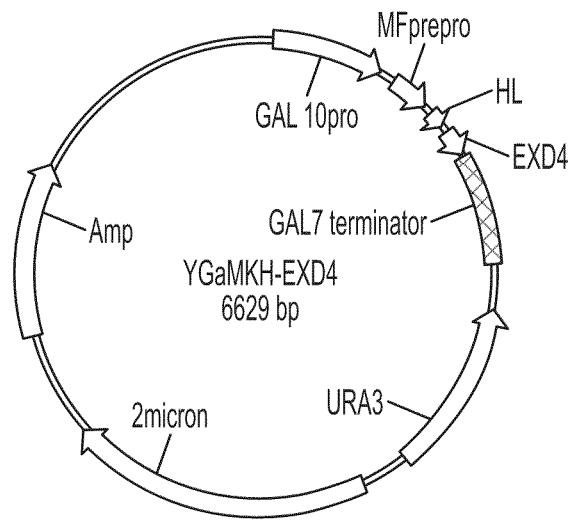

FIG. 26 shows a map of exendin-4 expression vector pYGaMKH-EXD4.

Figure 27:
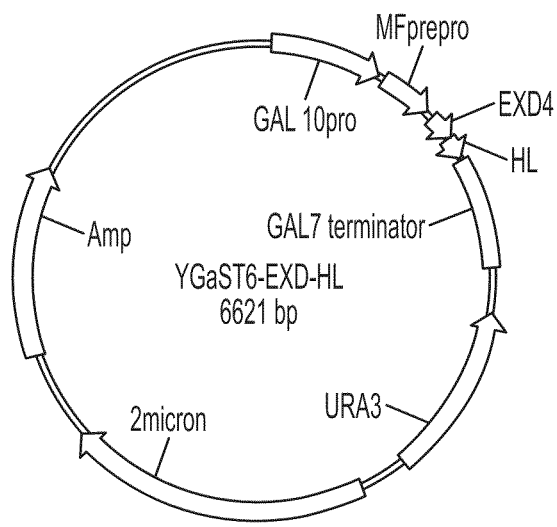

FIG. 27 shows a map of exendin-4 expression vector pYGaST6-EXD-HL.

Figure 28:
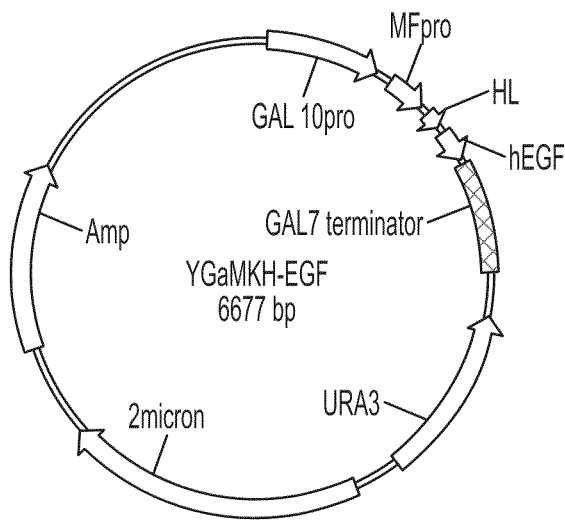

FIG. 28 shows a map of EGF expression vector pYGaMKH-EGF.

Figure 29:
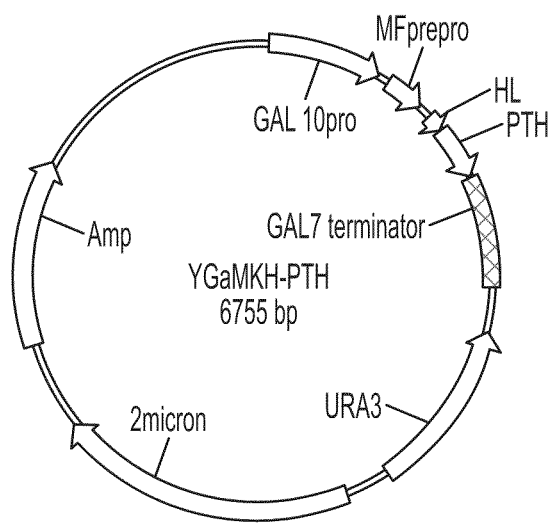

FIG. 29 shows a map of PTH expression vector pYGaMKH-PTH.

Figure 30:
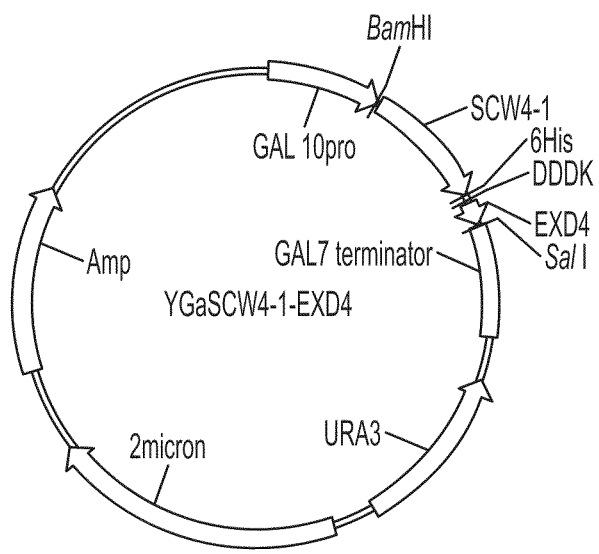

FIG. 30 shows a map of exendin-4 expression vector pYGaSCW4-1-EXD4.

Figure 31:
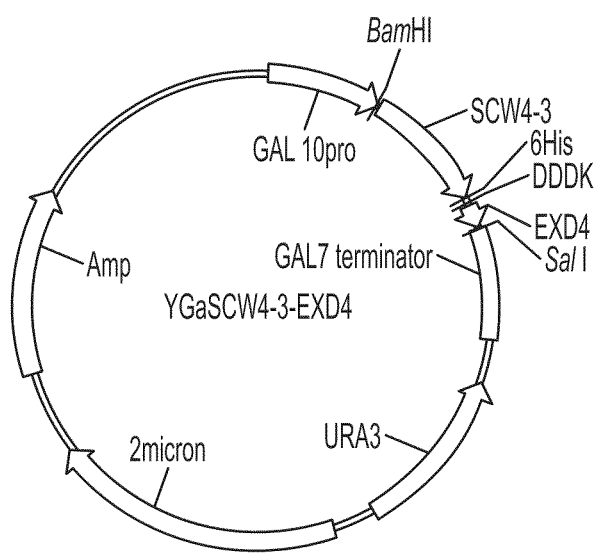

FIG. 31 shows a map of exendin-4 expression vector pYGaSCW4-3-EXD4.

Figure 32:
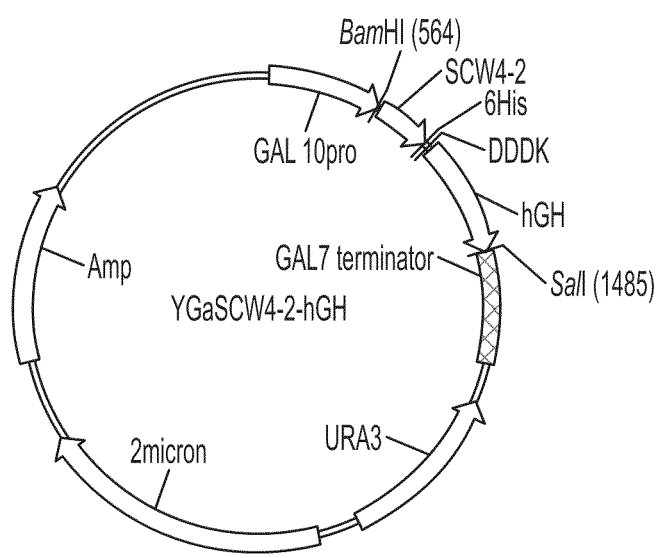

FIG. 32 shows a map of hGH expression vector pYGaSCW4-2-hGH.

DETAILED DESCRIPTION OF THE INVENTION

The present invention addresses the need for high level secretion of target polypeptides and for rapid and efficient screening technique for identification of SFPs applicable for achieving high level secretion of target polypeptides. While the invention is useful to optimize the recombinant expression of any protein, it is particularly useful to enable the production of proteins that cannot be produced on a large scale and/or at low cost due to their low level of expression in known expression systems. Optimized SFPs for accomplishing high level secretion of target polypeptides are described.

DEFINITIONS

It is to be noted that the term "a" or "an" entity refers to one or more of that entity; for example, "a vector" is understood to represent one or more vectors. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

By an "isolated polypeptide" or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

Also included as polypeptides of the present invention are fragments, derivatives, analogs, or variants of the foregoing polypeptides, and any combination thereof. The terms "fragment," "variant," "derivative" and "analog" when referring to polypeptides of the present invention include polypeptides that retain at least some of the biological, antigenic, or immunogenic properties of the corresponding native polypeptide. Fragments of polypeptides of the present invention include proteolytic fragments, as well as deletion fragments, in addition to other specific fragments discussed elsewhere herein. Variants of polypeptides of the present invention include fragments as described above, and also polypeptides with altered amino acid sequences due to amino acid substitutions, deletions, or insertions. Variants may occur naturally or be non-naturally occurring. Non-naturally occurring variants may be produced using art-known mutagenesis techniques. Variant polypeptides may comprise conservative or non-conservative amino acid substitutions, deletions or additions. Derivatives of polypeptides of the present invention, include polypeptides which have been altered so as to exhibit additional features not found on the native polypeptide. Variant polypeptides may also be referred to herein as "polypeptide analogs." As used herein a "derivative" of a polypeptide refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

By "a reference amino acid sequence" is meant the specified sequence without the introduction of any amino acid substitutions. As one of ordinary skill in the art would understand, if there are no substitutions, the "isolated polypeptide" of the invention comprises an amino acid sequence which is identical to the reference amino acid sequence.

Polypeptides described herein may have various alterations such as substitutions, insertions or deletions. Exemplary amino acids that can be substituted in the polypeptide include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Corresponding fragments of polypeptides at least 70%, 75%, 80%, 85%, 86%, 87%, 88%, 89%, 90%, 91%, 92%, 93%, 94%, 95%, 96%, 97%, 98%, or 99% identical to the polypeptides and reference polypeptides described herein are also contemplated.

Sequence identity is calculated by comparing two optimally aligned sequences over that region of comparison, determining the number of positions at which the identical amino acid residue or nucleotide occurs in both sequences to yield the number of matched positions, dividing the number of matched positions by the total number of positions in the region of comparison (i.e., the window size), and multiplying the result by 100 to yield the percentage of sequence identity. In one aspect, percent identity is calculated as the percentage of amino acid residues or nucleotides in the smaller of two sequences which align with an identical amino acid residue or nucleotide in the sequence being compared, when four gaps in a length of 100 amino acids or nucleotides may be introduced to maximize alignment (Dayhoff, in Atlas of Protein Sequence and Structure, Vol. 5, p. 124, National Biochemical Research Foundation, Washington, D.C. (1972), incorporated herein by reference). A determination of identity is typically made by a computer homology program known in the art. An exemplary program is the Gap program (Wisconsin Sequence Analysis Package, Version 8 for UNIX, Genetics Computer Group, University Research Park, Madison, Wis.) using the default settings, which uses the algorithm of Smith and Waterman (Adv. Appl. Math., 1981, 2: 482-489, which in incorporated herein by reference in its entirety).

In certain embodiments, substitutions are conservative amino acid substitutions. A "conservative amino acid substitution" is one in which the amino acid residue is replaced with an amino acid residue having a similar side chain. Families of amino acid residues having similar side chains have been defined within the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In one embodiment, the invention relates to a method of identifying a secretion fusion partner (SFP), said method comprising: (i) transforming a first host cell with a heterologous promoter operably linked to a polynucleotide encoding a secreted polypeptide; (ii) determining whether said secreted polypeptide is over-secreted from said first host cells as compared to the secretion level of said polypeptide if assayed when said polypeptide's natural promoter is linked to said polynucleotide encoding said secreted polypeptide; (iii) transforming a second host cell with a polynucleotide construct comprising a polynucleotide encoding a target polypeptide and a polynucleotide encoding a polypeptide determined to be over-secreted in step (ii), wherein said target polypeptide and said over-secreted polypeptide are fused in any order; (iv) culturing said second host cell under conditions where said polynucleotide construct expresses a fusion polypeptide; and (v) determining whether said fusion polypeptide is secreted into the extracellular culture medium; thereby identifying whether said over-secreted polypeptide is a secretion fusion partner.

In the methods of the present invention, SFPs may be identified from a "secretome" or "total secreted polypeptides." The secretome includes polypeptides secreted into and collected from the extracellular culture medium. Secretome are encoded by the DNA of any eukaryotic or prokaryotic organism, including bacteria, fungi (e.g., yeast), plants, and animals (e.g., mammals). Suitable bacteria include, but are not limited to *Escherichia* and *Bacillus* species. Suitable yeasts include, but are not limited to *Candida*, *Debaryomyces*, *Hansenula*, *Kluyveromyces*, *Pichia*, *Schizosaccharomyces*, *Yarrowia*, *Saccharomyces*, *Schwanniomyces*, and *Arxula* species. Examples of specific species include *Candida utilis*, *Candida boidinii*, *Candida albicans*, *Kluyveromyces lactis*, *Pichia pastoris*, *Pichia stipitis*, *Schizosaccharomyces pombe*, *Saccharomyces cerevisiae*, *Hansenula polymorpha*, *Yarrowia lipolytica*, *Schwanniomyces occidentalis*, and *Arxula adeninivorans*. Other fungi that may serve as a source of DNA include, but are not limited to *Aspergillus*, *Penicillium*, *Rhizopus*, and *Trichoderma* species. Plants that may serve as a source of DNA include, but are not limited to *Arabidopsis*, maize, tobacco, and potato. Suitable animals include, but are not limited to humans, mice, rats, rabbits, dogs, cats, and monkeys. In one embodiment, secretome can be derived from yeast, bacteria, plants or animals.

Secretome analysis for selecting abundantly secreted polypeptides can be accomplished using the techniques available in the art. For example, total secreted polypeptides isolated by concentrating culture supernatant can be analyzed using 2-D gel electrophoresis and/or Multidimensional Protein Identification Technology (1-DE/MudPIT). Polypeptides from the secretome can be analyzed by any kinds of protein purification columns, such as ion exchange columns, hydrophobic interaction columns, gel filtration columns, affinity columns, and reverse phase columns.

In one embodiment, yeast total secreted polypeptides (yeast secretome) produced during normal yeast cell growth are analyzed. Normal cell growth means cells that were cultured in minimal media (e.g., 0.67% yeast nitrogen base without amino acids, 0.5% casamino acid, 2% glucose and 0.002% uracil). Altered conditions could be used, which may include different carbon sources instead of glucose, e.g., galactose, xylose, fructose, mannose, sucrose, raffinose, and cellobiose. The altered conditions can also include limiting the level of any component of the media, e.g., nitrogen or phosphate.

The term "abundantly secreted" refers to polypeptides that are at least in the top 40%, 45%, 50%, 55%, 60%, 65%, or 70% in level of the secreted polypeptides from the secretome. Abundantly secreted polypeptides can be determined by PAI (protein abundance index) (Rappsilber et al., Genome Res. 12:1231-45 (2002)) which may be proportional to the number of proteins secreted. Examples of abundantly secreted proteins are shown in Table 1.

The term "over-secreted" is defined as the secretion of a polypeptide from a host cell at a level of at least 5×, 6×, 7×, 8×, 9× or 10× over the level of secretion of the polypeptide when expressed from the polypeptide's natural promoter. Over-secretion can also be assayed by comparing the secretion level of the abundantly secreted polypeptides compared to wild-type protein secretion levels. For example, wild-type yeast secreted proteins do not exceed secretion levels of about 20 mg/L during normal cell growth, however, when linked with a strong heterologous promoter, some of these proteins are over-secreted and exceed the secretion level of 20 mg/L.

In one embodiment, the methods of the invention further comprise determining an optimal size of a SFP for secretion of a fusion polypeptide. The optimal size of an SFP can be determined by deletion analysis of said SFP, wherein the level of secretion of fusion polypeptides, each containing different deletion constructs of the SFP, are compared. Some SFPs may have an optimal size that allows for even higher expression of fusion polypeptides than the expression obtained with the initially identified SFP. The optimal size of a SFP may allow for increased secretion level of a target polypeptide compared to the secretion level of the target polypeptide when fused to a sub-optimal SFP. The optimal size of an SFP may vary between target polypeptides, and can be determined using the methods disclosed herein or known in the art once the SFP has first been identified.

In one embodiment, SFP deletion fragments ending with hydrophilic sequences are selected. The hydrophilic domain of a protein is usually located near the surface of protein. Thus, the junction of the SFP and target polypeptide can be easily exposed between two polypeptides, which may make it easier for a protease to cleave the junction to release target polypeptides in vitro.

The term "fragment thereof," as applied to a SFP, refers to a polypeptide comprising any portion of the amino acid sequence of the SFP, wherein the fragment substantially retains the ability to induce the secretion of a target polypeptide to which it is fused.

The term "substantially retains the ability to induce the secretion of a target polypeptide to which it is fused," as used herein, refers to a fragment or derivative of a SFP which retains at least 50% of the ability of the parent SFP to induce secretion of a target polypeptide to which it is fused. In some embodiments, at least 60, 65, 70, 75, 80, 85, 90, or 95% of the ability to induce the secretion of a target polypeptide to which it is fused is retained. The ability to induce the secretion of a target polypeptide may be determined by routine techniques well known in the art and described above.

The term "derivative thereof," as applied to a SFP, refers to a polypeptide consisting of an amino acid sequence that is at least 70% identical to the amino acid sequence of the SFP, wherein the polypeptide substantially retains the ability to induce the secretion of a target polypeptide to which it is fused. In some embodiments, the derivative comprises an amino acid sequence that is at least 75%, 80%, 85%, 86%, 87%, 88%, 89%, 90%, 91%, 92%, 93%, 94%, 95%, 96%, 97%, 98%, or 99% identical to the amino acid sequence of the SFP. The derivative may comprise additions, deletions, substitutions, or a combination thereof to the amino acid sequence of the SFP. A derivative may include a mutant polypeptide with 1, 2, 3, 4, 5, 6, 7, 8, 9, 10, 11-15, 16-20, 21-25, or 26-30 additions, substitutions, or deletions. Additions or substitutions also include the use of non-naturally occurring amino acids.

Examples of derivatives of SFPs include, but are not limited to, deletion mutants (e.g., unidirectional deletion), addition of functional sequences (e.g., glycosylation sites, restriction enzyme sites), and deletion or addition (e.g., swapping) of pro-sequences or pre-sequences identified within SFPs. One of skill in the art can prepare derivatives of SFPs or nucleic acids encoding SFPs using routine mutagenesis techniques, such as those described in the references cited above, and identify derivatives that substantially retain the ability to induce the secretion of a target polypeptide to which it is fused.

In one embodiment, the SFP or a derivative or a fragment thereof is identified by the methods of the invention. In another embodiment, the nucleotide sequence encoding a SFP is selected from BGL2 (SEQ ID NO: 62), GAS3 (SEQ ID NO: 63), GAS5 (SEQ ID NO: 64), PST1 (SEQ ID NO: 65), SCW4 (SEQ ID NO: 66), SCW10 (SEQ ID NO: 67), SIMI (SEQ ID NO: 68), UTH1 (SEQ ID NO: 69), YGP1 (SEQ ID NO: 70), YPS1 (SEQ ID NO: 71), and ZPS1 (SEQ ID NO: 72). In another embodiment, a SFP is selected from BGL2 (SEQ ID NO: 80), GAS3 (SEQ ID NO: 81), GAS5 (SEQ ID NO: 82), PST1 (SEQ ID NO: 83), SCW4 (SEQ ID NO: 84), SCW10 (SEQ ID NO: 85), SIMI (SEQ ID NO: 86), UTH1 (SEQ ID NO: 87), YGP1 (SEQ ID NO: 88), YPS1 (SEQ ID NO: 89), and ZPS1 (SEQ ID NO: 90).

The methods of the present invention may be used with a "target polypeptide" or derivative thereof which is a polypeptide for which there is a desire for high level recombinant expression. The term "derivative thereof," as applied to a target polypeptides, refers to a polypeptide consisting of an amino acid sequence that is at least 70% identical to the amino acid sequence of the target polypeptide, wherein the polypeptide substantially retains its biological activity. In some embodiments, the derivative comprises an amino acid sequence that is at least 75%, 80%, 85%, 86%, 87%, 88%, 89%, 90%, 91%, 92%, 93%, 94%, 95%, 96%, 97%, 98%, or 99% identical to the amino acid sequence of the target polypeptide. The derivative may comprise additions, deletions, substitutions, or a combination thereof to the amino acid sequence of the target polypeptide. A derivative may include a mutant polypeptide with 1, 2, 3, 4, 5, 6, 7, 8, 9, 10, 11-15, 16-20, 21-25, or 26-30 additions, substitutions, or deletions. Additions or substitutions also include the use of non-naturally occurring amino acids.

Examples of derivatives of target proteins or polypeptides include, but are not limited to deletion mutants (e.g., unidirectional deletion), addition of functional sequences (e.g., glycosylation sites, restriction enzyme sites), and deletion or addition (e.g., swapping) of pro-sequences or pre-sequences identified within the target polypeptide. One of skill in the art can prepare derivatives of target polypeptides or nucleic acids encoding target polypeptides using routine mutagenesis techniques, such as those described in the references cited above, and identify derivatives that substantially retain biological activity of the target polypeptide.

Where the target polypeptide is fused to a SFP, the target polypeptide and the SFP are not polypeptides of the same naturally occurring protein. The target polypeptide may be one that is being studied for research purposes or one that is being produced for commercial purposes, e.g., therapeutic or industrial use. The target polypeptide may be from any plant, animal, or microorganism, and may be naturally occurring or modified, as long as it can be encoded by a nucleic acid. In one embodiment the target polypeptide is a human protein. In another embodiment, the target polypeptide is a cytokine, serum protein, colony stimulating factor, growth factor, hormone, or enzyme.

For example, the target polypeptide may be selected from an interleukin, coagulation factor, interferon-α, -β or -γ, granulocyte-colony stimulating factor, granulocyte macrophage-colony stimulating factor, tissue growth factor, epithelial growth factor, TGFα, TGFβ, epidermal growth factor, platelet-derived growth factor, fibroblast growth factor, follicle stimulating hormone, thyroid stimulating hormone, antidiuretic hormone, pigmentary hormone, parathyroid hormone, luteinizing hormone-releasing hormone, carbohydrate-specific enzymes, proteolytic enzymes, lipases, oxidoreductases, transferases, hydrolases, lyases, isomerases, ligases, immunoglobulins, cytokine receptors, lactoferrin, phospholipase A2-activating protein, insulin, tumor necrosis factor, calcitonin, calcitonin gene related peptide, enkephalin, somatomedin, erythropoietin, hypothalamic releasing factor, prolactin, chorionic gonadotropin, tissue plasminogen activator, growth hormone releasing peptide, thymic humoral factor, anticancer peptides, or antibiotic peptides. Specific examples include, but are not limited to human interleukin-2 (hIL-2), exendin-3, exendin-4 (EXD4), glucagon-like-peptide-1 (GLP-1), parathyroid hormone (PTH), human interleukin-1β, human interleukin-6, human interleukin-32α, -32β or -32γ, Factor VII, Factor VIII, Factor IX, human serum albumin, human interferon-α, -β or -γ, human granulocyte-colony stimulating factor, human granulocyte macrophage-colony stimulating factor, human growth hormone (hGH), human platelet-derived growth factor, human basic fibroblast growth factor, human epidermal growth factor (EGF), human insulin-like growth factor, human nerve growth factor, human transforming growth factor β-1, human follicle stimulating hormone, glucose oxidase, glucodase, galactosidase, glucocerebrosidase, glucuronidase, asparaginase, arginase, arginine deaminase, peroxide dismutase, endotoxinase, catalase, chymotrypsin, uricase, adenosine diphosphatase, tyrosinase, bilirubin oxidase, bovine galactose-1-phosphate uridyltransferase, jellyfish green fluorescent protein, Candida antarctica lipase B, Candida rugosa lipase, fungal chloroperoxidase, β-galactosidase, resolvase, α-galactosidase, β-glucosidase, trehalose synthase, cyclodextrin glycosyl transferase, xylanase, phytase, human lactoferrin, human erythropoietin, human paraoxonase, human growth differentiation factor 15, human galectin-3 binding protein, human serine protease inhibitor, Kunitz type 2, human Janus kinase 2, human fms-like tyrosine kinase 3 ligand, human YM1 & 2, human CEMI, human diacylglycerol acyltransferase, human leptin, human mL259, human proteinase 3, human lysozyme, human DEAD box protein 41, human etoposide induced protein 24, mouse caspase1, bovine angiogenin, and earthworm lumbrokinase.

In one embodiment, the target polypeptide is a polypeptide that is difficult to produce using conventional recombinant production methods, that is, a polypeptide that is not produced at all or is only produced at low levels. In another embodiment, the target polypeptide is one that is readily produced using known expression systems, but for which there is a desire to achieve higher levels of expression.

In one embodiment, a fusion polypeptide of the invention refers to a polypeptide comprising a secreted polypeptide fused to a target polypeptide in any order. In another embodiment, the invention relates to an isolated fusion polypeptide comprising a SFP of the invention fused to a target polypeptide.

As used herein the term "fused" refers to a fusion polypeptide produced recombinantly. In one embodiment, the fusion polypeptide comprises a secreted polypeptide fused to a target polypeptide, wherein the secreted polypeptide and target polypeptide are fused in any order. In another embodiment, the SFP is fused at the N-terminus or C-terminus of the target polypeptide. The SFP and target polypeptide can be fused with or without intervening amino acids, such as those encoded by linker DNA. In some embodiments, the distance between the SFP and target polypeptide can be 0 to 10; 0 to 20; 0 to 30; 0 to 40; or more amino acids. In some embodiments, the fusion polypeptide comprises a protease recognition sequence and/or an affinity tag.

In one embodiment, the isolated fusion polypeptide comprises a SFP or a derivative thereof comprising a hydrophilic (HL) domain comprising amino acids 176-213 of SEQ ID NO: 1, and a target polypeptide. In one embodiment, a modified HL domain is encoded by SEQ ID NO: 45.

The present invention further relates to methods of recombinantly producing a target polypeptide using the SFPs of the invention. In one embodiment, the method comprises preparing a construct comprising a nucleotide sequence encoding a target polypeptide operably linked to a nucleotide sequence encoding a SFP or a derivative or fragment thereof, transforming a host cell with the construct, culturing the host cell under conditions in which a fusion polypeptide is produced and secreted from the host cell, and separating said SFP from said target polypeptide.

The target polypeptide may be recombinantly produced using any expression system known in the art. Preferably, the target polypeptide is recombinantly expressed, e.g., in bacterial, yeast, or mammalian cell cultures. Recombinant expression may involve preparing a vector comprising a polynucleotide encoding the target polypeptide, delivering the vector into a host cell, culturing the host cell under conditions in which the target polypeptide is expressed, and separating the target polypeptide. Methods and materials for preparing recombinant vectors and transforming host cells using the same, replicating the vectors in host cells and expressing biologically active foreign polypeptides and proteins are discussed herein and described in Sambrook et al., Molecular Cloning, 3rd edition, Cold Spring Harbor Laboratory, 2001 and Ausubel et al., Current Protocols in Molecular Biology, John Wiley & Sons, New York 3rd edition, (2000), each incorporated herein by reference.

The target polypeptide may be isolated from the medium in which the host cells are grown, by purification methods known in the art, e.g., precipitation from the media, conventional chromatographic methods including immunoaffinity chromatography, receptor affinity chromatography, hydrophobic interaction chromatography, lectin affinity chromatography, size exclusion filtration, cation or anion exchange chromatography, high pressure liquid chromatography (HPLC), reverse phase HPLC, and the like. Still other methods of purification include those methods wherein the desired polypeptide is expressed and purified as a fusion polypeptide having a specific affinity peptide, tag, label, or chelating moiety that is recognized by a specific binding partner or agent. The purified polypeptide can be cleaved to yield the desired polypeptide, or can be left as an intact fusion polypeptide. Cleavage of the affinity tag component may produce a form of the desired polypeptide having additional amino acid residues as a result of the cleavage process. In one embodiment, the affinity tag is GST, MBP, NusA, thioredoxin, ubiquitin, FLAG, BAP, 6HIS, STREP, CBP, CBD, S-tag, or any combination thereof.

The target polypeptides of the invention may be extracellularly produced in a fusion form with a secretion fusion partner and can be separated from the SFP by in vitro protease treatment. If the isolated target polypeptide is not biologically active following the isolation procedure employed, various methods for "refolding" or converting the polypeptide to its tertiary structure and generating disulfide linkages, can be used to restore biological activity. Methods known to one of ordinary skill in the art include adjusting the pH of the solubilized polypeptide to a pH usually above 7 and in the presence of a particular concentration of a chaotrope. The selection of chaotrope is very similar to the choices used for inclusion body solubilization but usually at a lower concentration and is not necessarily the same chaotrope as used for the solubilization. It may be required to employ a reducing agent or the reducing agent plus its oxidized form in a specific ratio, to generate a particular redox potential allowing for disulfide shuffling to occur in the formation of the protein's cysteine bridge(s). Some of the commonly used redox couples include cysteine/cystamine, glutathione (GSH)/dithiobis GSH, cupric chloride, dithiothreitol (DTT)/dithiane DTT, 2-mercaptoethanol (bME)/dithio-b(ME). To increase the efficiency of the refolding, it may be necessary to employ a cosolvent, such as glycerol, polyethylene glycol of various molecular weights, and arginine.

The term "polynucleotide" is intended to encompass a singular nucleic acid as well as plural nucleic acids, and refers to an isolated nucleic acid molecule or construct, e.g., messenger RNA (mRNA), virally-derived RNA, or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding a therapeutic polypeptide contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of the present invention, as well as positive and negative strand forms, and double-stranded forms, of pestivirus vectors disclosed herein.

Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' non-translated regions, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a vector of the present invention may encode one or more polypolypeptides, which are post- or co-translationally separated into the final polypeptides via proteolytic cleavage. In addition, a vector, polynucleotide, or nucleic acid of the invention may encode heterologous coding regions, either fused or unfused to a first or second nucleic acid encoding of the invention, or variant or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid, which encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (e.g., a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions, which function in vertebrate cells, such as, but not limited to, promoter and enhancer segments from cytomegaloviruses (e.g., the immediate early promoter, in conjunction with intron-A), simian virus 40 (e.g., the early promoter), and retroviruses (such as, e.g., Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence).

A polynucleotide of the present invention may include RNA, for example, in the form of messenger RNA (mRNA). RNA of the present invention may be single stranded or double stranded.

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

The term "construct" refers to a non-naturally occurring nucleic acid molecule. A construct is a polynucleotide that encodes a fusion polypeptide. In one embodiment, the construct encodes a fusion polypeptide comprising a SFP or a candidate SFP and a target polypeptide. A construct can further comprise a circular or linear vector and can be combined with other polynucleotides, for example by homologous recombination.

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. The vectors of the present invention are capable of directing the expression of genes encoding target polypeptides to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), that serve equivalent functions.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In some embodiments, in order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding the target polypeptide or can be introduced on a separate vector. Cells stably transfected with the introduced nucleic acid can be identified by drug selection, auxotrophic marker selection, media composition, carbon source selection, or other methods known in the art (e.g., cells that have incorporated the selectable marker gene will survive, while the other cells die).

In one embodiment, a nucleotide sequence encoding a polypeptide or a fragment or a derivative thereof used in the methods of the present invention may further comprises at the 5' end and 3' end, DNA that is used for in vivo homologous recombination with a linear vector of the invention. The 5' end and 3' end DNA provides sufficient homologous sequence to allow in vivo recombination between the nucleotide sequence encoding a polypeptide or a fragment or a derivative thereof and the linear vector when they are co-transformed into the host cell. In one embodiment, the 5' end and 3' end DNA each comprise at least 20 base pairs that overlap with sequence of the linear vector, e.g., at least 30 or 40 base pairs. The addition of the 5' and 3' DNA may be carried out using routine recombinant DNA techniques, e.g., PCR and/or restriction enzyme cleavage and ligation.

The polynucleotide of the present invention may further encode an affinity tag, e.g., GST, MBP, NusA, thioredoxin, ubiquitin, FLAG, BAP, 6HIS, STREP, CBP, CBD, or S-tag. In some embodiments, the affinity tag may be encoded by a linker DNA or may be encoded by another portion of the polynucleotide of the invention such as the portion 5' or 3' to the region encoding the fusion protein.

The polynucleotide of the present invention may further include a linker DNA. In one embodiment the linker DNA encodes a linker peptide.

The linker DNA of the invention may be of sufficient length and have sufficient sequence identity to a portion of the nucleotide sequence of a linear vector to allow in vivo recombination between a polypeptide-encoding nucleotide sequence and the linear vector when they are co-transformed into a host cell. In one embodiment, the linker DNA is more than 20 base pairs in length, e.g., more than 30 or 40 base pairs in length. In a further embodiment, the linker DNA is at least 80% identical to the corresponding sequence on the linear vector, e.g., at least 85%, 90%, 95%, or 99% identical.

In one embodiment, the linker DNA encodes a protease recognition sequence thereby allowing cleavage at the junction of the SFP and the target polypeptide. For example, the linker DNA may encode a yeast kex2p or Kex2-like protease recognition sequence (e.g., an amino acid sequence comprising Lys-Arg, Arg-Arg, or Leu-Asp-Lys-Arg (SEQ ID NO: 74)), a mammalian furin-recognition sequence (e.g., an amino acid sequence comprising Arg-X-X-Arg), a factor Xa-recognition sequence (e.g., an amino acid sequence comprising Ile-Glu-Gly-Arg (SEQ ID NO: 75)), an enterokinase-recognition sequence (e.g., an amino acid sequence comprising Asp-Asp-Lys), a subtilisin-recognition sequence (e.g., an amino acid sequence comprising Ala-Ala-His-Tyr (SEQ ID NO: 76)), a tobacco etch virus protease-recognition sequence (e.g., an amino acid sequence comprising Glu-Asn-Leu-Tyr-Phe-Gln-Gly (SEQ ID NO: 77)), a ubiquitin hydrolase-recognition sequence (e.g., an amino acid sequence comprising Arg-Gly-Gly) or a thrombin-recognition sequence (e.g., an amino acid sequence comprising Arg-Gly-Pro-Arg (SEQ ID NO: 78)).

It is a preference to avoid unwanted cleavage of the fusion polypeptide by endogenous host proteases, either within the protease site in the linker or within the secreted polypeptide or the target polypeptide. Likewise, it is preferred to avoid cleavage within the target polypeptide or secreted polypeptide or SFP or fragment or derivative thereof by the protease used to cleave the secreted polypeptide from the target polypeptide. Thus, where a linker DNA encoding a protease recognition sequence is transformed into a host cell as part of a polynucleotide encoding a fusion polypeptide, the host cell preferably does not express the protease that recognizes the protease sequence in the linker. The host cell can either naturally not express the protease or the host cell can be modified to not express the protease (e.g., kex2 mutant host cells, kex2-like proteases mutant host cell, and furin mutant host cell). In certain embodiments, where the fusion polypeptide comprises a secreted polypeptide and a target polypeptide, the secreted polypeptide or SFP or fragment or derivative thereof and/or the target polypeptide can either naturally not comprise the host protease recognition sequence or the secreted polypeptide or SFP or fragment or derivative thereof and/or target polypeptide can be modified so that they do not contain sequences that are recognized by the host protease. Where the fusion polypeptide comprises a secreted polypeptide or SFP or fragment or derivative thereof, a target polypeptide, and a peptide linker comprising a protease recognition sequence, the secreted polypeptide or SFP or fragment or derivative thereof and/or the target polypeptide can either naturally not comprise the protease recognition sequence or the secreted polypeptide or SFP or fragment or derivative thereof and/or the target polypeptide can be modified so that they do not contain sequences that are recognized by the protease that recognizes the protease recognition sequence of the peptide linker.

In another embodiment, the linker DNA encodes an affinity tag, e.g., GST, MBP, NusA, thioredoxin, ubiquitin, FLAG, BAP, 6HIS, STREP, CBP, CBD, or S-tag.

In a further embodiment, the linker DNA encodes a restriction enzyme recognition site and a protease recognition sequence (e.g., kex2p-like protease- or kex-2p-recognition sequence).

Expression of polypeptides in prokaryotes may be carried out with vectors containing constitutive or inducible promoters directing the expression of the target polypeptide-reporter polypeptide fusion. Examples of suitable *E. coli* expression vectors include pTrc (Amrann et al., *Gene* 69:301-315 (1988)) and pET (Studier et al., GENE EXPRESSION TECHNOLOGY: METHODS IN ENZYMOLOGY 185, Academic Press, San Diego, Calif. (1990) 60-89).

For expression in yeast cells, suitable yeast expression vectors include, but are not limited to pYepSec1 (Baldari et al., *EMBO J.* 6:229-234 (1987)), pMFa (Kurjan et al., *Cell* 30:933-943 (1982)), pJRY88 (Schultz et al., *Gene* 54:113-123 (1987)), pYES2 (Invitrogen Corporation, San Diego, Calif.), and picZ (Invitrogen Corp, San Diego, Cal.).

For expression in insect cells, baculovirus expression vectors may be used. Examples of baculovirus vectors available for expression of polypeptides in cultured insect cells (e.g., SF9 cells) include the pAc series (Smith et al., *Mol. Cell. Biol.* 3:2156-2165 (1983)) and the pVL series (Lucklow et al., *Virology* 170:31-39 (1989)).

In another embodiment, the host cells are mammalian cells and the vector is a mammalian expression vector. Examples of mammalian expression vectors include, but are not limited to, pCDM8 (Seed, *Nature* 329:840 (1987)) and pMT2PC (Kaufman et al., *EMBO J.* 6: 187-195 (1987)). When used in mammalian cells, the expression vector's control functions are often provided by viral regulatory elements. For example, commonly used promoters are derived from polyoma, adenovirus 2, cytomegalovirus and Simian Virus 40. For other suitable expression systems for both prokaryotic and eukaryotic cells, see, e.g., Chapters 16 and 17 of Sambrook et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

Preferred vectors include, but are not limited to, plasmids, phages, cosmids, episomes, viral particles or viruses, and integratable DNA fragments (i.e., fragments integratable into the host genome by homologous recombination). Preferred viral particles include, but are not limited to, adenoviruses, baculoviruses, parvoviruses, herpesviruses, poxviruses, adenoassociated viruses, Semliki Forest viruses, vaccinia viruses, and retroviruses. Preferred expression vectors include, but are not limited to, pcDNA3 (Invitrogen) and pSVL (Pharmacia Biotech). Other expression vectors include, but are not limited to, pSPORT™ vectors, pGEM™ vectors (Promega), pPROEXvectors™ (LTI, Bethesda, Md.), Bluescript™ vectors (Stratagene), pQE™ vectors (Qiagen), pSE420™ (Invitrogen), and pYES2™ (Invitrogen).

In one embodiment, expression vectors are replicable DNA constructs in which a DNA sequence encoding the target polypeptide is operably linked or connected to suitable control sequences capable of effecting the expression of the target polypeptide in a suitable host. DNA regions are operably linked or connected when they are functionally related to each other. For example, a promoter is operably linked or connected to a coding sequence if it controls the transcription of the sequence. Amplification vectors do not require expression control domains, but rather need only the ability to replicate in a host, usually conferred by an origin of replication, and a selection gene to facilitate recognition of transformants. The need for control sequences in the expression vector will vary depending upon the host selected and the transformation method chosen. Generally, control sequences include, but are not limited to a transcriptional promoter, enhancers, an optional operator sequence to control transcription, polyadenylation signals, a sequence encoding suitable mRNA ribosomal binding and sequences which control the termination of transcription and translation. Such regulatory sequences are described, for example, in Goeddel; GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of polypeptide desired, etc.

The expression vectors of the invention can be introduced into host cells to thereby produce proteins or peptides, e.g., fusion proteins or peptides, encoded by nucleic acids as described herein. Preferred vectors contain a promoter that is recognized by the host organism.

In one embodiment, the promoter of the present invention is a strong heterologous promoter which is used for the recombinant production of foreign polypeptides. The heterologous promoter may be inducible or may be constitutive. Preferred heterologous promoters are those used for commercial production of proteins, such as those described below. The heterologous promoter of the invention is distinguishable from the natural or wild-type SFP promoter.

In certain embodiments, the promoter sequences of the present invention may be prokaryotic, eukaryotic or viral. Examples of suitable prokaryotic sequences include the PR and PL promoters of bacteriophage lambda (The bacteriophage Lambda, Hershey, A. D., Ed., Cold Spring Harbor Press, Cold Spring Harbor, N.Y. (1973), which is incorporated herein by reference in its entirety; Lambda II, Hendrix, R. W., Ed., Cold Spring Harbor Press, Cold Spring Harbor, N.Y. (1980), which is incorporated herein by reference in its entirety); the trp, recA, heat shock, and lacZ promoters of *E. coli* and the SV40 early promoter (Benoist et al., *Nature*, 290:304-310 (1981)), which is incorporated herein by reference in its entirety). For yeast, examples of suitable promoters include, but are not limited to GAPDH, PGK, ADH, PHO5, TEF, GAL1, and GAL10. Additional promoters include, but are not limited to, mouse mammary tumor virus, long terminal repeat of human immunodeficiency virus, maloney virus, cytomegalovirus immediate early promoter, Epstein Barr virus, Rous sarcoma virus, human actin, human myosin, human hemoglobin, human muscle creatine, and human metallothionein.

Additional regulatory sequences can also be included in preferred vectors. Examples of suitable regulatory sequences are represented by the Shine-Dalgarno sequence of the replicase gene of the phage MS-2 and of the gene cII of bacteriophage lambda.

Moreover, suitable expression vectors can include an appropriate marker that allows the screening of the transformed host cells. The transformation of the selected host is carried out using any one of the various techniques well known to the expert in the art and described in Sambrook et al., supra.

An origin of replication can also be provided either by construction of the vector to include an exogenous origin or may be provided by the host cell chromosomal replication mechanism. If the vector is integrated into the host cell chromosome, the latter may be sufficient. Alternatively, rather than using vectors which contain viral origins of replication, one skilled in the art can transform mammalian cells by the method of co-transformation with a selectable marker and target polypeptide DNA. An example of a suitable marker is dihydrofolate reductase (DHFR) or thymidine kinase (see, U.S. Pat. No. 4,399,216).

Nucleotide sequences encoding the target polypeptide may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulation are disclosed by Sambrook et al., supra and are well known in the art. Methods for construction of mammalian expression vectors are disclosed in, for example, Okayama et al., *Mol. Cell. Biol.* 3:280 (1983), Cosman et al., *Mol. Immunol.* 23:935 (1986), Cosman et al., *Nature* 312:768 (1984), EP-A-0367566, and WO 91/18982, each of which is incorporated herein by reference in its entirety.

The host cells used in the present invention may be any host cells known to those of skill in the art. In certain embodiments, suitable host cells include bacterial, fungal, (e.g., yeast), plant, or animal (e.g., mammalian or insect) cells. In some embodiments, suitable yeast cells include *Candida, Debaryomyces, Hansenula, Kluyveromyces, Pichia, Schizosaccharomyces, Yarrowia, Saccharomyces, Schwanniomyces*, and *Arxula* species. Specific examples include *Candida utilis, Candida boidinii, Candida albicans, Kluyveromyces lactis, Pichia pastoris, Pichia stipitis, Schizosaccharomyces pombe, Saccharomyces cerevisiae, Hansenula polymorphs, Yarrowia lipolytica, Schwanniomyces occidentalis*, and *Arxula adeninivorans*. Other suitable fungi include *Aspergillus, Penicillium, Rhizopus*, and *Trichoderma* species. In some embodiments, bacteria that may be used as host cells include *Escherichia, Pseudomonas*, and *Bacillus* species. In some embodiments, suitable plant host cells include *Arabidopsis*, maize, tobacco, and potato. In some embodiments, animal cells include cells from humans, mice, rats, rabbits, dogs, cats, monkeys, and insects. Examples include CHO, COS 1, COS 7, BSC 1, BSC 40, BMT 10, and Sf9 cells. In a particular embodiment, the host cells are yeast cells.

Polynucleotides of the invention may be introduced into the host cell as part of a circular plasmid, or as linear DNA comprising an isolated polypeptide coding region or a viral vector. Methods for introducing DNA into the host cell that are well known and routinely practiced in the art include transformation, transfection, electroporation, nuclear injection, or fusion with carriers such as liposomes, micelles, ghost cells, and protoplasts.

A reporter protein that is rapidly and efficiently detectable may be used in the present invention. In one embodiment, the reporter protein has an activity that can be positively selected for in order to automate the screening process. In an additional embodiment, the reporter protein is a protein that is secreted into the extracellular space, e.g., invertase, sucrase, cellulase, xylanase, maltase, amylase, glucoamylase, galactosidase (e.g., alpha-galactosidase beta-galactosidase, melibiase), phosphatase (e.g., PHO5), beta-lactamase, lipase or protease. In a particular embodiment, the secreted protein permits a cell to grow on a particular substrate. As an example of reporter system in mammalian cell, CD2/neomycin-phosphotransferase (Ceo) gene can be used as a secretion reporter in the media containing antibiotics G418 to trap the secretion pathway genes in mouse embryonic stem cells (De-Zolt et al., Nucleic Acid Res. 34:e25 (2006)).

In one embodiment, the host cells are yeast, the reporter protein is invertase and the transformed yeast cells are selected for their ability to grow on sucrose or raffinose. In another embodiment, the host cells are yeast, the reporter protein is melibiase and the transformed yeast cells are selected for their ability to grow on melibiose. In a further embodiment, the host cells are yeast, the reporter protein is amylase (e.g., an endoamylase, exoamylase, β-amylase, or glucoamylase), the yeast cells are non-amylolytic, and the transformed cells are screened for their ability to degrade starch. In an additional embodiment, the step of identifying cells showing an activity of the reporter protein occurs by using a reporter protein which provides resistance to a growth inhibitor, e.g., an antibiotic. In another embodiment, the reporter protein is a protein that can be detected visually, e.g., green fluorescent protein or luciferase. In one embodiment, the step of identifying cells showing an activity of the reporter protein occurs by using two or more reporter proteins, e.g., lipase and invertase.

The host cells of the present invention do not exhibit reporter protein activity. In one embodiment, the host cells naturally do not express the reporter protein. In other embodiments, the gene(s) encoding the reporter protein have been deleted in whole or in part or have been mutated such that the reporter protein is not expressed or is expressed in an inactive form. Methods for rendering a cell deficient in a particular protein are well known in the art and any such method may be used to prepare the host cells of the present invention (Sambrook et al., supra). For yeast, a reporter gene deficiency can be introduced using well known gene replacement techniques (Rothstein, *Meth. Enzymol.* 194:281 (1991)).

Nucleic acids encoding a target polypeptide may be obtained from any source using routine techniques well known in the art, including isolation from a genomic or cDNA library, amplification by PCR, or chemical synthesis.

A library of nucleic acids or fragments thereof may be obtained from DNA of any type, including genomic DNA, cDNA, synthetic DNA, and recombinant DNA. Nucleic acids other than DNA may also be used, including RNA and non-naturally occurring nucleic acids. A library of pre-selected nucleic acid fragments may be obtained by diversifying previously identified nucleic acid fragments, e.g., by unidirectional deletion, mutation, addition of functional sequences (e.g., glycosylation sites) or swapping of pre- and pro-signal sequences between nucleic acid fragments. In one embodiment, the nucleic acid fragments have a size of less than 1000 base pairs, e.g., less than 700, 500, or 300 base pairs. A library of nucleic acid fragments may be constructed by enzymatic cleavage of the DNA, by cDNA synthesis, or by recombinant DNA technology (e.g., unidirectional deletion, mutagenesis).

The nucleic acid fragments may be derived from the entire genome of an organism, e.g., an entire genomic or cDNA library. The fragments may also be derived from any subset of the entire genome, e.g., a subtracted library or a sized library.

The following examples are illustrative, but not limiting, of the methods and compositions of the present invention. Other suitable modifications and adaptations of the variety of conditions and parameters normally encountered and which are obvious to those skilled in the art are within the spirit and scope of the invention.

EXAMPLES

Example 1

Determination of Optimal Size of YGR106C Gene for Extracellular Secretion

This example demonstrates the optimal regions of YGR106 that are needed for extracellular secretion. As shown in FIG. 1A, the YGR106C (hereafter Secretion Fusion Partner1, SFP1) protein (SEQ ID NO: 1) consists of 265 amino acid residues containing signal peptide, three glycosylation sites, one hydrophilic domain (HL) and one trans-membrane domain (TM).

Over-expression of intact YGR106C gene under the control of GAL10 promoter produced no YGR106C protein in culture medium. However, a truncated SFP1 (amino acids 1-213 of SEQ ID NO: 1) was highly secreted into the culture medium using a C-terminally truncated form of YGR106C under the control of yeast GAL10 promoter.

Further identification of the optimal domains of the SFP1 gene were determined for secretion. Several functional domains of SFP1 protein such as secretion signal (amino acids 1-19 of SEQ ID NO: 1), hydrophilic domain (HL) (amino acids 176-213 of SEQ ID NO: 1) and transmembrane domain (TM) (amino acids 220-247 of SEQ ID NO: 1) were determined by Kyte-Doolittle hydropathy analysis (FIG. 1A).

Recombinant yeast *Saccharomyces cerevisiae* 2805 (Mat a ura3 INV2 pep4::HIS3 can1) strains containing different vectors with serially deleted SFP1 genes were constructed and the secretion of SFP1 related proteins from each vector was compared (FIG. 1B). Initially, to express the intact SFP1 protein, the open reading frame (ORF) of SFP1 was amplified from *S. cerevisiae* 2805 genomic DNA with PCR primers, a sense primer T9F (SEQ ID NO: 2) containing BamHI site and an anti-sense primer H159 (SEQ ID NO: 3) containing SalI site. PCR was carried out with Pfu polymerase (Stratagene, USA) or Ex-Taq DNA polymerase (TaKaRa Korea Biomedical Inc., Seoul, Korea). PCR conditions included one denaturing step of 94° C. for 5 min, and 25 amplification cycles of 94° C. for 30 sec, 55° C. for 30 sec and 72° C. for 1 min, followed by a final extension of 72° C. for 7 min. The amplified SFP1 ORF was digested with BamHI-SalI and subcloned into BamHI-SalI sites of YEGα-HIR525 (Sohn et al., *Process Biochem.* 30:653 (1995)), and the resulting plasmid was named YGaT91.

In order to express a truncated SFP1 protein which deleted C-terminus to TM domain, a partial SFP1 gene was amplified from YGaT91 vector with a sense primer T9F (SEQ ID NO: 2) and an anti-sense primer H160 (SEQ ID NO: 4). The amplified partial SFP1 gene was cloned into the YEGα-HIR525 by using the same method of YGaT91 construction and the resulting plasmid was named YGaT92.

To express another truncated SFP1 protein which deleted from C-terminus to half of HL domain, a partial SFP1 gene was amplified from YGaT91 vector with a sense primer T9F (SEQ ID NO: 2) and an anti-sense primer H161 (SEQ ID NO: 5). The amplified partial SFP1 gene was cloned into the YEGα-HIR525 by using the same method of YGaT91 construction and the resulting plasmid was named YGaT93.

To express another truncated SFP1 protein which deleted from C-terminus to HL domain, a partial SFP1 gene was amplified from YGaT91 vector with a sense primer T9F (SEQ ID NO: 2) and an anti-sense primer H162 (SEQ ID NO: 6). The amplified partial SFP1 gene was cloned into the YEGα-HIR525 by using the same method of YGaT91 construction and the resulting plasmid was named YGaT94.

To express another truncated SFP1 protein which deleted from C-terminus to the $3^{rd}$ glycosylation site, a partial SFP1 gene was amplified from YGaT91 vector with a sense primer T9F (SEQ ID NO: 2) and an anti-sense primer H205 (SEQ ID NO: 7). The amplified partial SFP1 gene was cloned into the YEGα-HIR525 by using the same method of YGaT91 construction and the resulting plasmid was named YGaT95.

To express another truncated SFP1 protein which deleted from C-terminus to the 2$^{nd}$ glycosylation site, a partial SFP1 gene was amplified from YGaT91 vector with a sense primer T9F (SEQ ID NO: 2) and an anti-sense primer H204 (SEQ ID NO: 8). The amplified partial SFP1 gene was cloned into the YEGα-HIR525 by using the same method of YGaT91 construction and the resulting plasmid was named YGaT96.

To express another truncated SFP1 gene which deleted from C-terminus to the 1$^{st}$ glycosylation site, a partial SFP1 gene was amplified from YGaT91 vector with a sense primer T9F (SEQ ID NO: 2) and an anti-sense primer H203 (SEQ ID NO: 9). The amplified partial SFP1 gene was cloned into the YEGα-HIR525 by using the same method of YGaT91 construction and the resulting plasmid was named YGaT97.

Yeast *S. cerevisiae* 2805 strain (Mat a ura3 INV2 pep4:: HIS3 can1) was transformed with the constructed vectors (YGaT91, YGaT92, YGaT93, YGaT94, YGaT95, YGaT96, and YGaT97). Single colonies selected from UD plates (0.67% yeast nitrogen base without amino acids, 0.77 g/l amino acid mixture, 2% glucose and 2% agar) of different transformations were cultured in YPDG broth media (1% yeast extract, 2% Bacto-peptone, 1% glucose, 1% galactose) for 40 hours at 30° C. Secreted proteins in the 0.6 ml of each culture broth were concentrated with 0.4 ml of acetone and separated by SDS-PAGE. As shown in FIG. 1C, SFP1 related proteins were detected only in cells harboring YGaT92, YGaT93 and YGaT94 (lanes 2, 3, and 4, respectively). Two bands, one glycosylated form and the other non-glycosylated, were detected in all three positive strains. But the other cells, YGaT91, YGaT95, YGaT96, and YGaT97, showed no such bands (lane 1, 5, 6, and 7, respectively). These results show that removal of the TM domain and retension of the domain containing all three glycosylation sites allows for SFP1 extracellular secretion.

Example 2

Figure 2A:
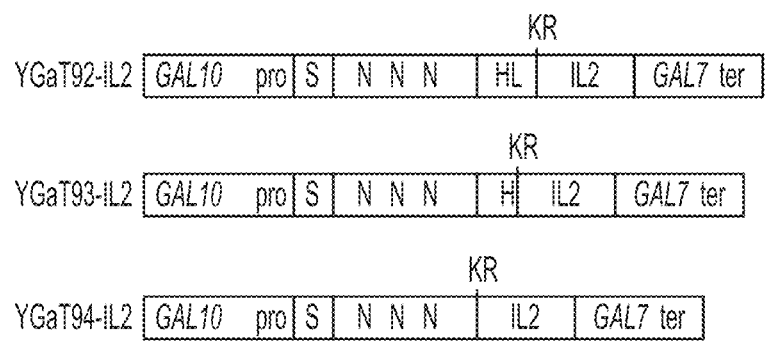

Determination of Optimal Size of SFP1 Gene as a Fusion Partner for Secretion of a Target Protein This example demonstrates the use of SPF1 derivatives as fusion partners. In order to test SFP1 derivatives as fusion partners for the secretion of an exemplary target protein, human interleukin-2 (hIL-2), three vectors were constructed to express hIL-2 as fusion proteins with three SFP1 derivatives (SFP1-92 (SEQ ID NO: 39), SFP1-93 (SEQ ID NO: 40), and SFP1-94 (SEQ ID NO: 41)) of YGaT92, YGaT93 and YGaT94, respectively (FIG. 2A). A hIL-2 fusion with YGaT91 was also generated, SFP1-91 (SEQ ID NO: 38), data not shown. To fuse hIL2 gene with SFP1-92 of YGaT92, a partial SFP1 gene was amplified with a sense primer GAL100 (SEQ ID NO: 10) which recognize GAL10 promoter and an anti-sense primer H121 (SEQ ID NO: 11) from YGaT92 vector. To facilitate the fusion with hIL2 gene and to induce in vivo cleavage of the hIL2 fusion proteins by yeast dipeptidyl protease Kex2p (Mizuno K et al., *Biochem. Biophys. Res. Commun.* 156:246 (1988)), H121 primer (SEQ ID NO: 11) was designed to contain Kex2p cleavage sequence and N-terminal hIL2 sequence. Human IL-2 gene was amplified with a sense primer IL2F (SEQ ID NO: 12) which contains a part of SFP1 sequence complementary to H121 primer (SEQ ID NO: 11) and an anti-sense primer IL2R (SEQ ID NO: 13). IL2R primer contains a part of GAL7 terminator sequence. The amplified PCR fragment containing a SFP1-92 and hIL-2 gene was fused by overlap-extension PCR with GAL100 and GT50R (SEQ ID NO: 14) primer. GT50R primer is an anti-sense primer recognizing GAL7 terminator. The resulting PCR product was flanked with 100 bp of GAL10 promoter sequence and 50 by of GAL7 terminator sequence. One of the merits of *S. cerevisiae* as an expression host is the possibility to use an efficient and correct homologous recombination strategy. It is well known in the art that a linearized vector and a DNA fragment that shares DNA sequence overlap on either side of the fragment ends can undergo recombination that restores circular topology of plasmid (Kunes et al., *Genetics.* 115: 73 (1987)). This feature of *S. cerevisiae* was used for the construction of an expression host system.

To use YGaT92 vector for in vivo recombination backbone, YGaT92 vector was digested with BamHI/SalI. The linearized vector fragment was isolated from agarose gel using a gel extraction kit (Bioneer, Korea). The PCR product amplified with GAL100/GT50R primer set shared more than 50 nucleotides with the linearized vector. The minimum requirement for in vivo recombination is about a 30 nucleotide overlap (Oldenberg et al., *Nucleic Acids Res.* 25: 451 (1997). A fifty nucleotide overlap is sufficient for plasmid re-construction in *S. cerevisiae*. Recombinant *S. cerevisiae* 2805 strain was directly constructed by co-transformation with the above-described PCR product and vector fragment. The resulting plasmid constructed by recombination was named YGaT92-IL2 (FIG. 2A). For the construction of *S. cerevisiae* 2805 strain transformed with YGaT93-IL2 vector, we used the same procedure as used for YGaT92-IL2 plasmid construction except a H120 primer (SEQ ID NO: 15) was used instead of H121 primer (SEQ ID NO: 11). The H120 primer was an antisense primer recognizing the 3' terminus of SFP1 gene of the YGaT93 vector and containing a Kex2p cleavage sequence and a N-terminal hIL2 sequence. To transform the *S. cerevisiae* 2805 strain with YGaT94-IL2 vector, the H119 primer (SEQ ID NO: 16) was used instead of the H121 primer (SEQ ID NO: 11) and otherwise, the same procedure as described for the YGaT92-IL2 plasmid construction was used. The H119 primer is an antisense primer recognizing 3' terminus of SFP1 gene of YGaT94 vector and contains Kex2p cleavage sequence and N-terminal hIL2 sequence.

Figure 2B:
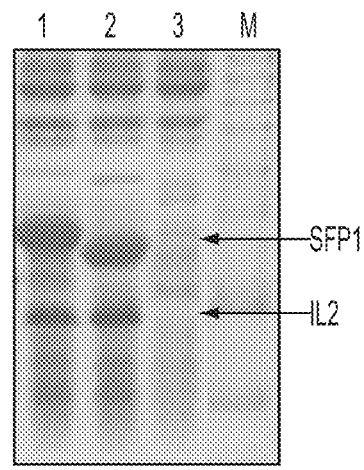

Single colonies selected from UD plate (0.67% yeast nitrogen base without amino acids, 0.77 g/l amino acid mixture, 2% glucose and 2% agar) were cultured in YPDG broth media (1% yeast extract, 2% Bacto-peptone, 1% glucose, 1% galactose) for 40 hours at 30° C. Secreted proteins in the 0.6 ml of each culture broth were concentrated with 0.4 ml of acetone and separated by SDS-PAGE. As shown in FIG. 2B, the SFP1 derivative protein and hIL2 was secreted from the *S. cerevisiae* cells harboring YGaT92-IL2 (SEQ ID NO: 58) and YGaT93-IL2 (lane 1 and 2, respectively) but not for YGaT94-IL2 cells (lane 3). This result show that the HL domain is important for the secretion of SPF1 derivative proteins when expressed in a fusion form.

Example 3

Expression of Target Protein Fused with SFP1 Derivatives

The SFP1-92 (SEQ ID NO: 39) constructed in Example 2 from YGaT92 was used for the secretory production of Exendin-4 (EXD4), a 39 amino acids peptide analogue of glucagons-like peptide-1 (GLP1). For simple and efficient purification of intact EXD4 proteins, 6-Histidine tag and enterokinase cleavage site (DDDDK (SEQ ID NO: 79), D: aspartic acid, K: Lysine) were added to the C-terminus of SFP1. Therefore the fusion protein from N-terminus to C-terminus included a SFP1 fragment, a 6-Histidine tag, an enterokinase cleavage site and an EXD4 sequence. To construct YGaT92-EXD4 vector that expressed SFP1-92 EXD4 fusion protein, the SFP1-92 gene was amplified from YGaT92 vector with GAL100 primer (SEQ ID NO: 10) and anti-sense primer HDK-R (SEQ ID NO: 17) that recognize the HL sequence and contains 6 Histidine codons. The EXD4 gene was amplified with sense primer HDK-F (SEQ ID NO: 18) that contains 18 nucleotides complementary to HDK-R primer and DDDDK codons and anti-sense primer EXD-R (SEQ ID NO: 19) which contains 18 nucleotide of GT50R (SEQ ID NO: 14) primer sequence. The amplified SFP1-92 and EXD4 gene was fused by overlap-extension PCR with the GAL100/GT50R primer set. The recombinant S. cerevisiae 2805 strain harboring YGaT92-EXD4 vector was directly constructed by in vivo recombination through the co-transformation of the fused fragment and BamHI/SalI digested YGaT92 vector fragment as described in Example 2.

Figure 3A:
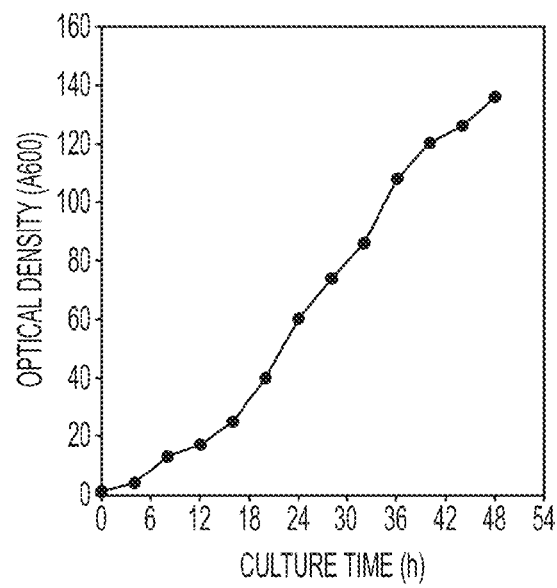
Figure 3B:
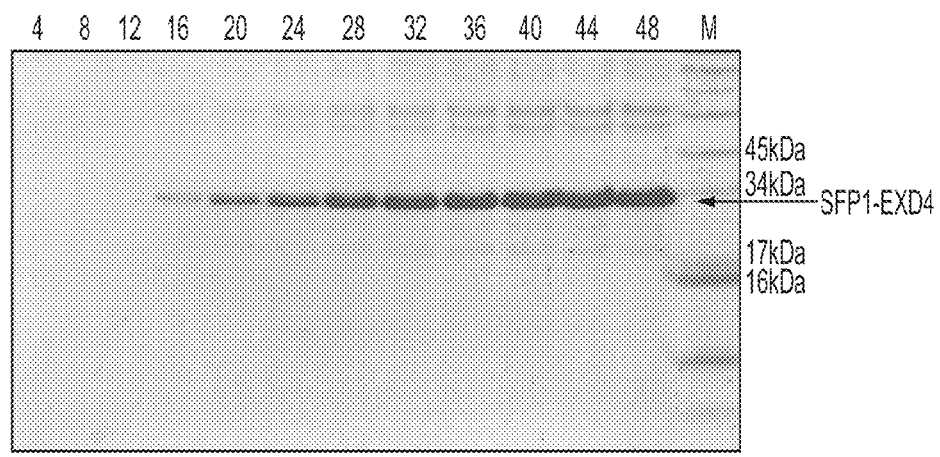

A recombinant yeast strain transformed with the YGaT92-EXD4 was cultured in a 5-L jar fermentor by fed-batch culture to be evaluated for its ability to induce the secretory production of SFP1-92-EXD4 fusion protein. A seed culture to be inoculated in the fermentor was cultured in a flask using a seed culture medium (6.7% yeast nitrogen base without amino acids, 0.5% casamino acids and 2% glucose). When the culture using a fermentation culture medium (4% yeast extract, 1% peptone, 2% glucose) as an initial fermentation medium reached an OD600 of about 15, a fed-batch medium (15% yeast extract, 30% glucose, 30% galactose) was supplied with various amounts according to cell growth rates. After a culture period of about 48 hrs, the culture reached an OD600 of about 160. 10 µl of the medium was collected at the given time points and assessed for secreted proteins by SDS-PAGE (FIG. 3A-B). Compared to a standard protein bands, the secreted SFP1-EXD4 was estimated to be about 500 mg/L. Supernatant was recovered by centrifugation to remove yeast cells, and concentrated and desalted by ultrafiltration (Quickstand, Amersham).

Figure 4:
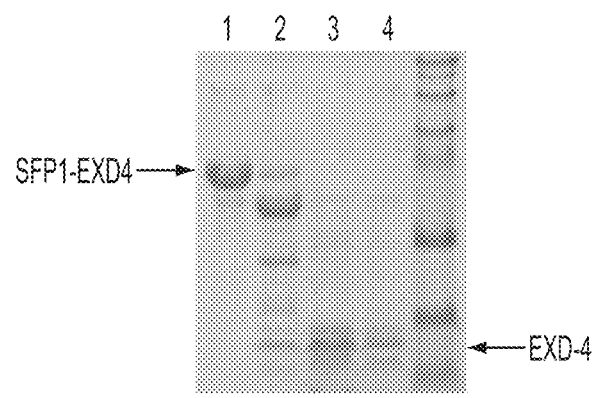

The fusion protein, SFP1-92-EXD4 was purified with Ni-NTA affinity column (QIAGEN, USA) (FIG. 4, lane 1). To recover EXD-4 from SFP1-92 fusion protein, the purified fusion protein was digested with different concentrations of enterokinase (Invitrogen, USA). The samples were dissolved in enterokinase buffer [20 mM Tris-HCl (pH8.0), 50 mM NaCl, 2 mM $CaCl_2$]. Equal amount of protein samples were digested with 0.1, 0.2 and 0.3 µl of enterokinase for 1 hr at 37° C. The resulting proteins were analyzed by SDS-PAGE (FIG. 4, lanes 2, 3, and 4, respectively).

Several small protein bands were generated rater than two bands. Those small fragments were likely the result of non-specific digestion of SFP1 by enterokinase. SFP1 protein contains DDK (137th amino acid) and EDK (168th amino acid) residues, which are possible substrate of enterokinase.

Figure 5A:
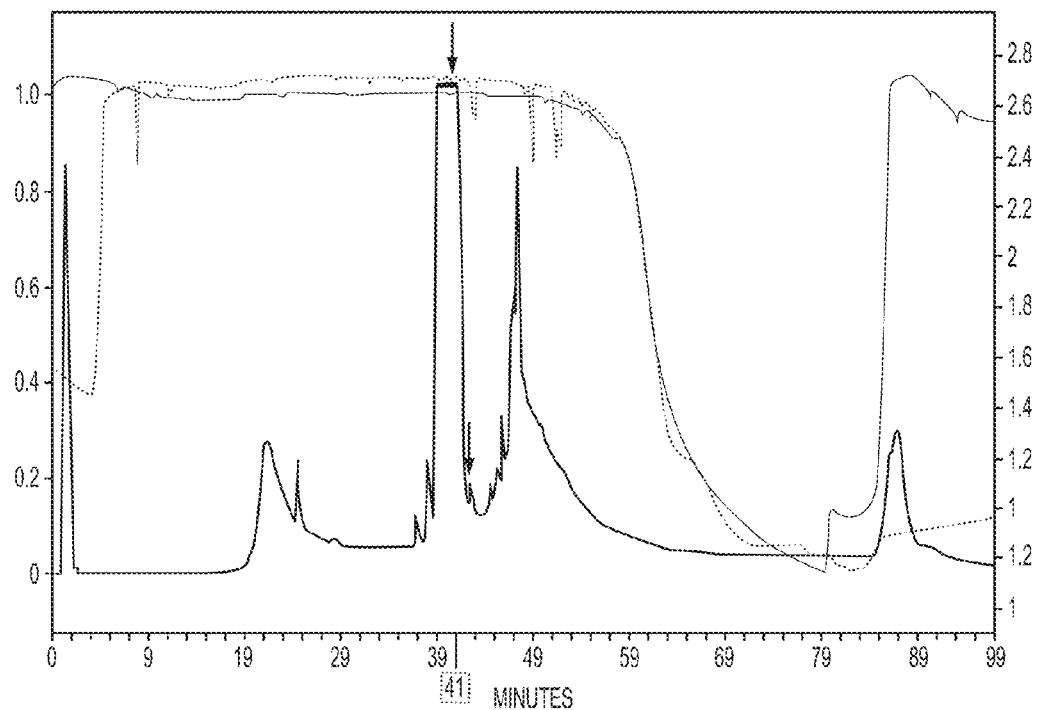
FIG. 5 shows (A) a HPLC analysis of enterokinase digested SFP1-EXD4 fusion protein, (B) SDS-PAGE analysis of HPLC fractions. The numbers above the gel indicate HPLC fraction number.
Figure 5B:
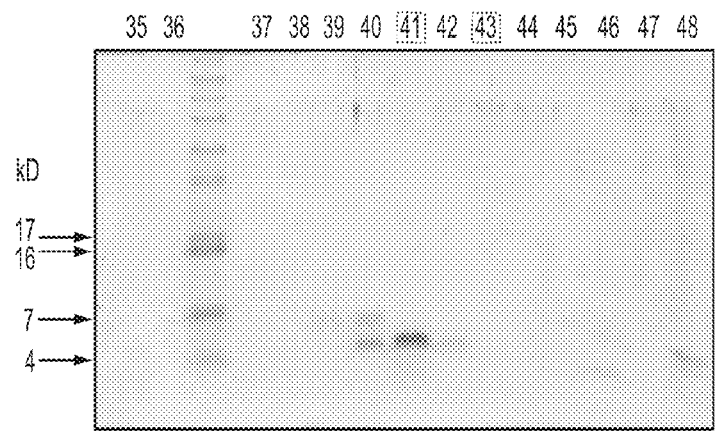
Figure 6:
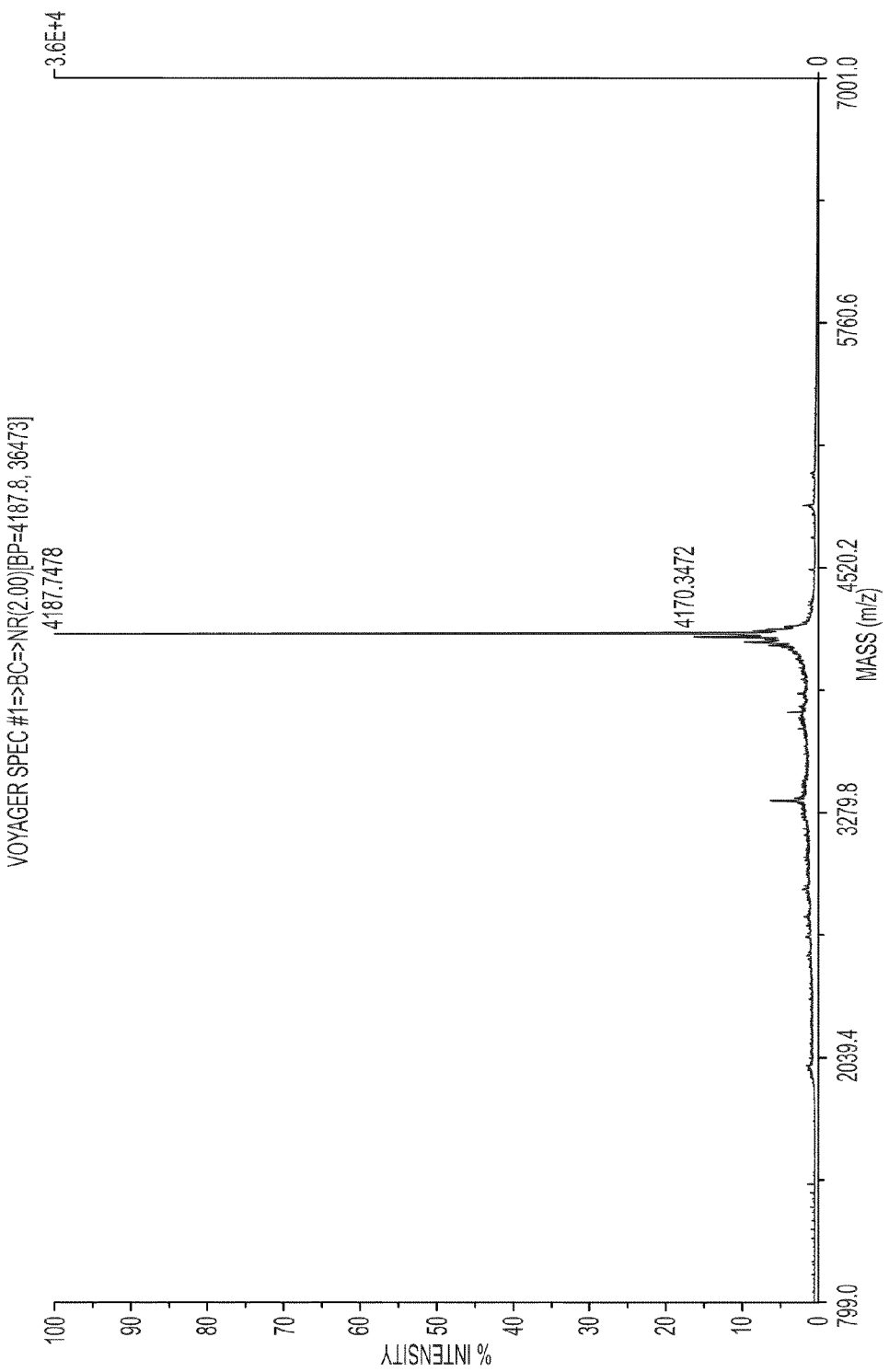
FIG. 6 is a MALDI-TOF analysis of purified EXD4 protein.

For the further analyses of EXD-4 recovered from SFP1-92-EXD4, enterokinase treated sample (FIG. 4, lane 3) was fractionated by HPLC (FIG. 5A). Proteins detected as peaks in HPLC chromatogram were analyzed by SDS-PAGE (FIG. 5B). HPLC fraction number 41 showed as a single band expected to be EXD-4. The protein was further analyzed to determine its molecular weight (MW) by MALDI-TOF (Korea Basic Science Institute, Daejeon, Korea) (FIG. 6). The MW of EXD-4 produced from the SFP1-92 fusion was 4187.8 Da which is was matched with the MW calculated by its amino acid sequence.

Figures 7A, 7B:
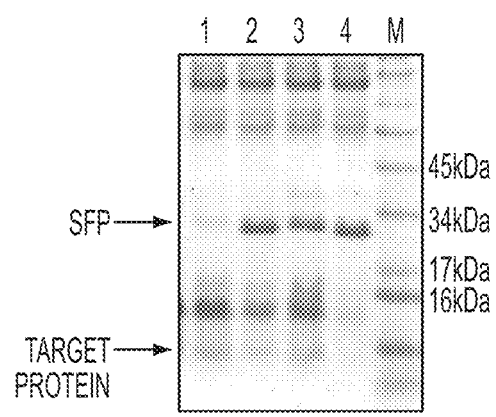

To construct robust SFP1-92 fusion partner that is resistant to enterokinase, DDK and EDK residue were changed to DGK and EGK residue, respectively (FIG. 7A). To change DDK residue to DGK residue, the 5' SFP1-92 fragment was amplified from YGaT92-EXD4 with GAL100 primer (SEQ ID NO: 8) and anti-sense mutagenic primer H307 (SEQ ID NO: 20) that contains a glycine codon rather than an aspartic acid codon of the DDK residue. The 3' SFP1-92-EXD4 fragment was also amplified with sense primer H306 (SEQ ID NO: 21) that is complementary to H307 (SEQ ID NO: 20) and GT50R primer (SEQ ID NO: 14) from the YGaT92-EXD4 vector. These fragments were fused by overlap extension PCR with the GAL100/GT50R primer set. After digestion with BamHI/SalI, the fused fragment was cloned into the BamHI/SalI site of the YGaT92-EXD4 vector. The nucleotide sequence of the resulting plasmid was confirmed and named YGaT921-EXD4 containing SFP1-921 (SEQ ID NO: 42).

In order to change EDK residue to EGK residue, the 5' SFP1 fragment was amplified from YGaT92-EXD4 with GAL100 primer (SEQ ID NO: 10) and anti-sense mutagenic primer H309 (SEQ ID NO: 22) that contains a glycine codon rather than an aspartic acid codon of the EDK residue. The 3' SFP1-92-EXD4 fragment was also amplified with sense primer H308 (SEQ ID NO: 23) that is complementary to H309 (SEQ ID NO: 22) and GT50R primer (SEQ ID NO: 14) from the YGaT92-EXD4 vector. These fragments were fused by overlap extension PCR with the GAL100/GT50R primer set. After digestion with BamHI/SalI, the fused fragment was cloned into the BamHI/SalI site of the YGaT92-EXD4 vector. The nucleotide sequence of the resulting plasmid was confirmed and named YGaT922-EXD4 containing SFP1-922 (SEQ ID NO: 43).

In order to change both DDK and EDK residues to DGK and EGK, respectively, the 5' SFP1 fragment was amplified from YGaT921-EXD4 with GAL100 primer (SEQ ID NO: 10) and anti-sense mutagenic primer H309 (SEQ ID NO: 22) that contains a glycine codon rather than an aspartic acid codon of the EDK residue. The 3' SFP1-EXD4 fragment was also amplified with sense primer H308 (SEQ ID NO: 23) that is complementary to H309 (SEQ ID NO: 22) and GT50R primer (SEQ ID NO: 14) from YGaT92-EXD4 vector. These fragments were fused by overlap extension PCR with the GAL100/GT50R primer set. After digestion with BamHI/SalI, the fused fragment was cloned into BamHI/SalI site of YGaT92-EXD4 vector. The nucleotide sequence of the resulting plasmid was confirmed and named YGaT923-EXD4 (FIG. 25) containing SFP1-923 (SEQ ID NO: 44).

The S. cerevisiae 2805 strain was transformed with the vectors: YGaT92-EXD4, YGaT921-EXD4, YGaT922-EXD4, and YGaT923-EXD4. Single colonies selected from UD plate (0.67% yeast nitrogen base without amino acids, 0.77 g/l amino acid mixture, 2% glucose and 2% agar) were cultured in YPDG broth media (1% yeast extract, 2% Bacto-peptone, 1% glucose, 1% galactose) for 40 hours at 30° C. Proteins contained in the 0.6 ml of culture supernatants were precipitated with 0.4 ml of acetone and dissolved in enterokinase buffer [20 mM Tris-HCl (pH8.0), 50 mM NaCl, 2 mM $CaCl_2$]. Equal amount of protein samples were digested with 0.1 µl of enterokinase for 1 hr at 37° C. and separated by SDS-PAGE.

As shown in FIG. 7B, SFP1 produced from the YGaT92-EXD4 transformant was digested to around 15 kDa fragments (FIG. 7B, lane 1) but SFP1 produced from YGaT921-EXD4 and YGaT922-EXD4 transformants (FIG. 7B, lanes 2 and 3, respectively) were more resistant to internal SFP1 enterokinase digestion than SFP1 from YGaT92-EXD4. Finally, most of the SFP1 fragment produced from the YGaT923-EXD4 (SEQ ID NO: 59) transformant was intact (FIG. 7B, lane 4). Therefore, the results show that the SFP1 variant from YGaT923-EXD4 was successfully applied for expression and purification of target protein.

Example 4

Secretion of Target Proteins Fused with the HL Domain of SFP1

As shown in Example 2, the HL domain plays an important role for the secretion of target protein. The function of HL in secretion of target proteins may be due to the acidic charged amino acids within the HL domain because the solubility of protein is closely related to the net charge of protein. To investigate the function of the HL domain as a fusion partner, we used the HL domain for the secretion of EXD4.

The HL domain was fused to the N-terminus of the target protein. The HL-EXD4 gene was amplified from YGaT923-EXD4 vector with the H221 (SEQ ID NO: 24)/GT50R (SEQ ID NO: 14) primer set and the pre-pro leader peptide of mating factor α(MFα) was amplified with GAL100/LNK-R (SEQ ID NO: 25) primer set. Because H221 and LNK-R primer (SEQ ID NO: 25) contains complementary linker sequence, these two fragments were fused with GAL100 (SEQ H) NO: 8)/GT50R (SEQ ID NO: 14) primer set by overlap-extension PCR. The YGaMKH-EXD4 (FIG. 26) transformant was directly constructed by co-transformation with the fused fragment and BamHI/SalI digested YGaT92 vector fragment as described in Example 2. The YGaMKH-EXD4 plasmid contains a linker peptide (AASASAGLA-LDKR) (SEQ ID NO:91) between the pre-pro leader peptide of MFα and peptide for in vivo processing by Kex2p, A recombinant yeast strain transformed with the YGaMKH-EXD4 was cultured in a 5-L jar fermentor by fed-batch culture to be evaluated for its ability to induce the secretory production of HL-EXD4. A seed culture to be inoculated in the fermentor was cultured in a flask using a seed culture medium (6.7% yeast nitrogen base without amino acids, 0.5% casamino acids and 2% glucose). When the culture using a fermentation culture medium (4% yeast extract, 1% peptone, 2% glucose) as an initial fermentation medium reached an OD600 of about 15, a fed-batch medium (15% yeast extract, 30% glucose, 30% galactose) was supplied with various amounts according to cell growth rates. After a culture period of about 48 hrs, the culture reached an OD600 of about 150. 10 □l of the medium was collected at the given time points and assessed for secreted proteins by SDS-PAGE (FIG. 8). When compared to standard protein bands, the secreted HL-EXD4 was estimated to be about 200 mg/L.

To test the effect of C-terminal fusion of HL peptide to the target protein, a plasmid, YGaST6-EXD-HL (FIG. 27) was constructed. The EXD4 gene was amplified with sense primer H412 (SEQ ID NO: 26) and anti-sense primer H413 (SEQ ID NO: 27) from YGaMKH-EXD4 and HL peptide was amplified with HL-F (SEQ ID NO: 28) and HL-GT50R (SEQ ID NO: 29) from YGaMKH-EXD4. Because the H413 primer (SEQ ID NO: 27) contains a complementary sequence to HL-F primer, these two fragments were fused with H412 (SEQ ID NO: 26)/GT50R (SEQ ID NO: 14) primer set by overlap-extension PCR. The H412 primer (SEQ ID NO: 26) contains linker sequence and can fuse to pre-pro leader of MFα amplified with GAL100 (SEQ ID NO: 10)/LNK-R (SEQ ID NO: 25) primer set. Each of amplified fragments was fused by overlap-extension PCR with GAL100/GT50R primer set in order of pre-pro leader of MFα, EXD4 and HL domain gene. YGaST6-EXD-HL transformant was directly constructed by co-transformation with the fused fragment and BamHI/SalI digested YGaT92 vector fragment as described in Example 2. A recombinant yeast strain transformed with the YGaST6-EXD4-HL was cultured in a 5-L jar fermentor by fed-batch culture to be evaluated for its ability to induce the secretory production of EXD4-HL. After a culture period of about 48 hrs, the culture reached an OD600 of about 160. 10 μl of the medium was collected at the given time points and assessed for secreted proteins by SDS-PAGE (FIGS. 9A and B). Compared to standard protein bands, the secreted EXD4-HL was estimated to be about 500 mg/L. In the case of HL fusion to EXD4, the C-terminal fusion showed much higher secretion level of EXD4 than N-terminal fusion. Thus, the results show that the HL domain is useful for the secretion of proteins in fusion form at both the N-terminus and C-terminus of the target protein. However, C-terminal fusion showed increased secretion of target protein.

To further test the HL domain as a fusion partner, the HL domain was used for expression of human epidermal growth factor (hEGF). The YGaMKH-EGF plasmid (FIG. 28) was constructed. In YGaMKH-EGF, the HL domain is fused to the N-terminus of hEGF, the MFα pre-pro peptide-HL fusion peptide gene was amplified from the YGaMKH-EXD4 vector with the GAL100 (SEQ ID NO: 10)/DDK-R (SEQ ID NO: 30) primer set and the hEGF gene was amplified with sense primer H410 (SEQ ID NO: 31) which contains complementary sequence to DDK-R primer and anti-sense primer H411 (SEQ ID NO: 32) which contains the same sequence as GT50R (SEQ ID NO: 14). Each of the amplified fragments was fused by overlap-extension PCR with the GAL100/GT50R primer set. The YGaMKH-EGF transformant was co-transformed with the fused fragment and the BamHI/SalI digested YGaT92 vector fragment as described in Example 2.

A recombinant yeast strain transformed with the YGaMKH-EGF was cultured in a 5-L jar fermentor by fed-batch culture to be evaluated for its ability to induce the secretory production of HL-EGF. After a culture period of about 48 hrs, the culture reached an OD600 of about 155. 10 μl of the medium was collected at the given time points and assessed for secreted proteins by SDS-PAGE (FIGS. 10A and B). Compared to standard protein bands, the secreted HL-EGF was estimated to be about 400 mg/L.

Figure 11A:
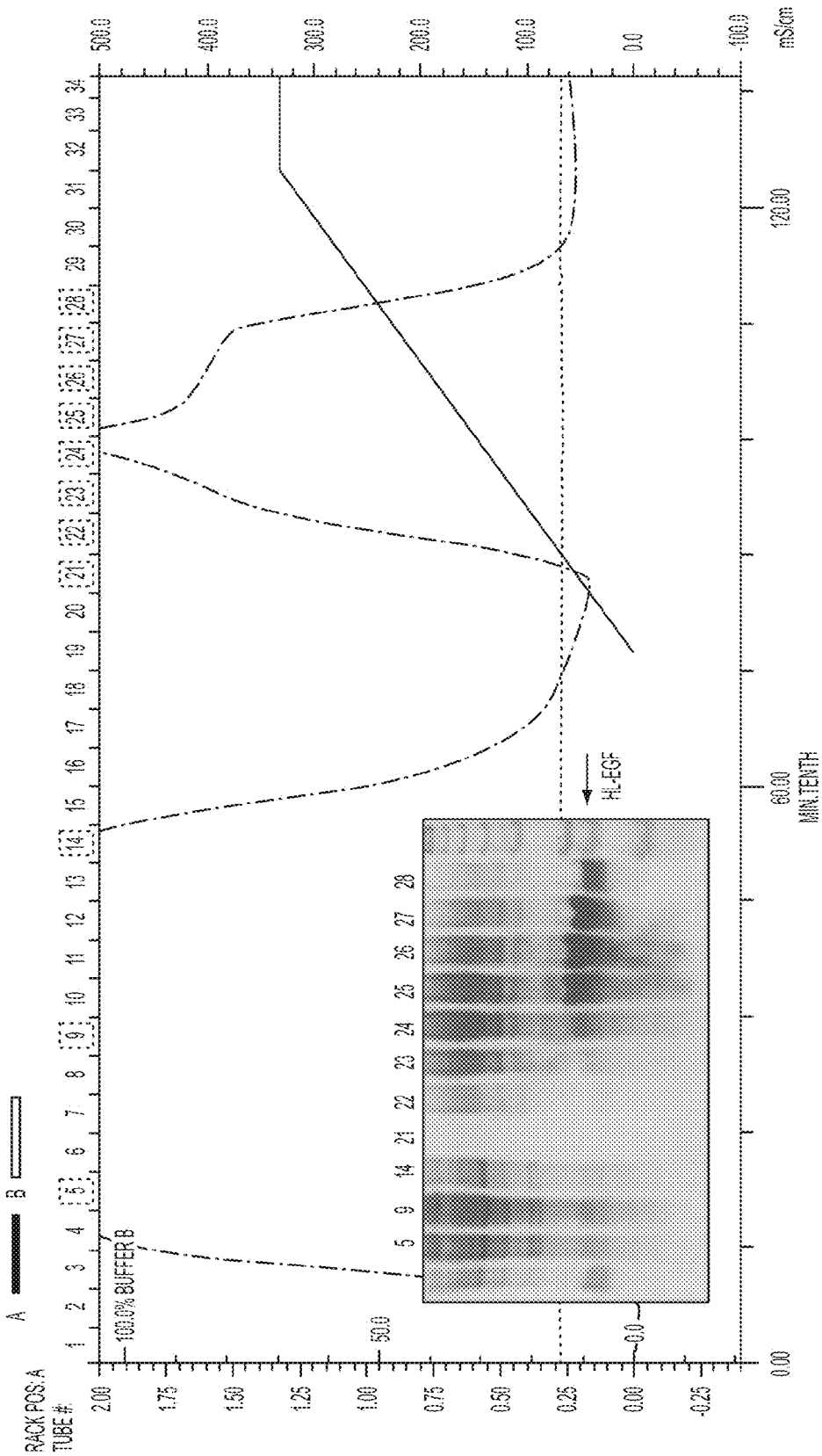
Figure 11B:
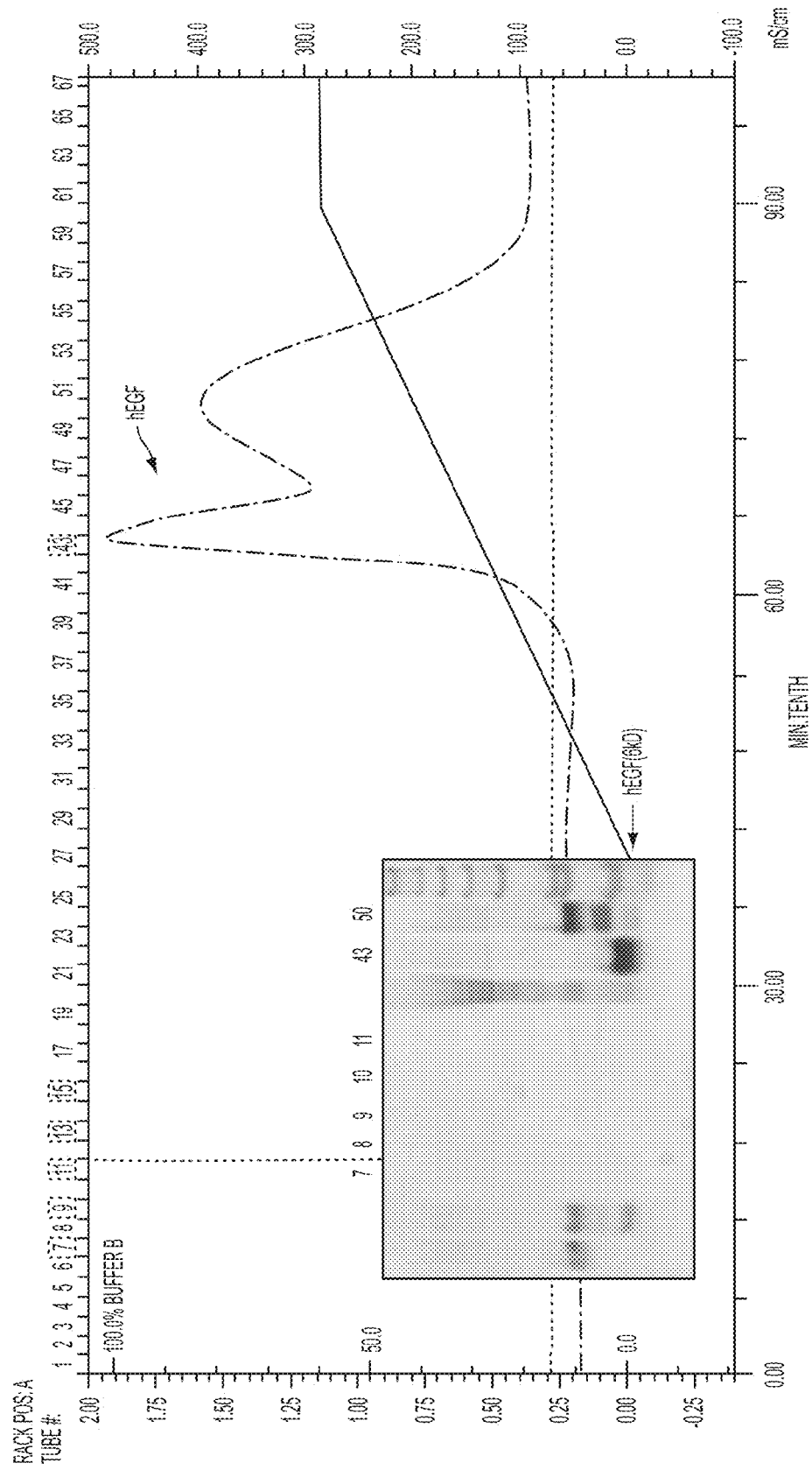

The HL-hEGF fusion protein was directly purified by Ni-NTA affinity chromatography (FIG. 11A). To separate hEGF and HL peptide, the purified fusion protein was digested with enterokinase and the resulting fragments were fractionated by Ni-NTA affinity chromatography again. As shown in FIG. 11B, intact and pure hEGF (6 kD) was efficiently purified.

The HL domain was also applied for the secretory production of human parathyroid hormone (hPTH). The YGaMKH-PTH (FIG. 29) vector was constructed by fusing the HL domain to N-terminus of hPTH. The hPTH gene was amplified with sense primer H310 (SEQ ID NO: 33) which contains complementary sequence to DDK-R primer (SEQ ID NO: 30) and anti-sense primer H311 (SEQ ID NO: 34) which contains the same sequence as GT50R (SEQ ID NO: 14). This fragment was fused with the MFα pre-pro peptide-HL fusion peptide gene by overlap-extension PCR with GAL100 (SEQ ID NO: 10)/GT50R (SEQ ID NO: 14) primer set. The YGaMKH-PTH transformant was directly constructed by co-transformation with the fused fragment and the BamHI/SalI digested YGaT92 vector fragment as described in Example 2. A recombinant yeast strain transformed with the YGaMKH-PTH was cultured in a 5-L jar fermentor by fed-batch culture to be evaluated for its ability to induce the secretory production of HL-PTH. After a culture period of about 48 hrs, the culture reached an OD600 of about 120. 10 µl of the medium was collected at the given time points and assessed for secreted proteins by SDS-PAGE (FIGS. 12A and B). Two major bands related to HL-PTH were detected. The majority of hPTH was detected in the fusion form of MFα pro-HL-PTH at 60 kD due to noncomplete in vivo cleavage by Kex2p. The band showing Kex2p cleavage of HL-PTH was also detected. Overall the secreted proteins related to PTH were estimated to be more than 500 mg/L. The His tagged proteins in the fermentation supernatant were directly purified by Ni-NTA affinity chromatography. The purified proteins were separated into two kinds of band in SDS-PAGE as expected (FIG. 13, lane 1). The larger band (Pro-HL-PTH) was disappeared after in vitro processing with Kex2p (FIG. 13, lane 2). The fusion protein (HL-PTH) was correctly separated to HL peptide and hPTH peptide (lane 3) by enterokinase digestion.

Examples 1-4 show that identification and modification of optimal regions of the YGR106C gene resulted in construction of efficient multi-functional fusion partners derived from SFP1 for the secretory production and isolation of recombinant proteins.

Example 5

Selection of Secretion Fusion Partners from the Yeast Secretome

This example demonstrates a technique for identifying abundantly secreted proteins useful as fusion partners.

First, yeast total secreted proteins (yeast secretome) produced during normal yeast cell growth were analyzed. For yeast secretome isolation, yeast *S. cerevisiae* 2805 strain was cultivated in minimal media (0.67% yeast nitrogen base without amino acids, 0.5% casamino acid, 2% glucose and 0.002% uracil) for 20 hours (M1) and 40 hours (M2). Five hundred milliliter of culture supernatant was concentrated using membrane filtration and the total secreted proteins were recovered. Yeast cells were confirmed to be intact using a confocal laser scanning microscope after staining the cells with a fluorescent dye hochest (FIGS. 14A and B).

The M2 secretome sample was analyzed by 2-D gel electrophoresis (FIG. 15). Most of the secretome proteins were identified in acidic regions, except the RNase A which was added to remove the ribonucleic acid contamination in the total protein samples. As shown in FIG. 15, the 2-D gel electrophoresis was not enough to identify all secreted proteins present in sample M2. Accordingly, 1-DE/MudPIT (Multidimensional Protein Identification Technology) method was also applied for a more complete identification of the yeast secretome (FIG. 16). As a result, 57 and 83 proteins were identified from M1 and M2, respectively. Taken together, 98 unique proteins were identified. Among them, 42 proteins were commonly detected in M1 and M2 samples. To confirm the proteins that were most likely secreted proteins, two programs, WoLF PSORT and pTARGET, for predicting protein localization and for signal prediction were used. Among the 42 proteins, 35 proteins (representing 80%) were predicted as secreted proteins (Table 1).

TABLE 1

Thirty five genes identified by yeast secretome analysis and their protein abundance index (PAI) determined by MASS analysis.

|    | Gi Number | Standard Name | Systematic Name | PAI |
|----|-----------|---------------|-----------------|------|
| 1  | 6320260   | PST1          | YDR055W         | 15.4 |
| 2  | 6323331   | EXG1          | YLR300W         | 9.9  |
| 3  | 6321718   | SCW4          | YGR279C         | 9.1  |
| 4  | 6324169   | YGP1          | YNL160W         | 7.2  |
| 5  | 6321721   | BGL2          | YGR282C         | 5.8  |
| 6  | 6324419   | ZPS1          | YOL154W         | 5.1  |
| 7  | 6319552   | ECM33         | YBR078W         | 4.2  |
| 8  | 6323964   | SCW10         | YMR305C         | 3.4  |
| 9  | 6323871   | GAS3          | YMR215W         | 3.4  |
| 10 | 6323967   | GAS1          | YMR307W         | 2.8  |
| 11 | 6322895   | UTH1          | YKR042W         | 2.5  |
| 12 | 6323150   | YPS3          | YLR121C         | 2.2  |
| 13 | 6319638   | TOS1          | YBR162C         | 2.2  |
| 14 | 6321628   | CRH1          | YGR189C         | 2.2  |
| 15 | 6322754   | CWP1          | YKL096W         | 1.5  |
| 16 | 6324002   | EGT2          | YNL327W         | 1.5  |
| 17 | 6324395   | DSE4          | YNR067C         | 1.5  |
| 18 | 6322303   | CIS3          | YJL158C         | 1.5  |
| 19 | 6322068   | SIM1          | YIL123W         | 1.2  |
| 20 | 6324543   | GAS5          | YOL030W         | 1.0  |
| 21 | 6323014   | BPT1          | YLL015W         | 1.0  |
| 22 | 6322864   | PRY2          | YKR013W         | 0.7  |
| 23 | 6319568   | PHO3          | YBR092C         | 0.7  |
| 24 | 6321906   | BZZ1          | YHR114W         | 0.7  |
| 25 | 6323288   | HSP60         | YLR259C         | 0.7  |
| 26 | 6323139   | CCW12         | YLR110C         | 0.6  |
| 27 | 6323423   | CCW14         | YLR390W-A       | 0.6  |
| 28 | 6323009   | KNS1          | YLL019C         | 0.6  |
| 29 | 6321410   | SCW11         | YGL028C         | 0.5  |
| 30 | 6322290   | N/A           | YJL171C         | 0.5  |
| 31 | 6322287   | KRE9          | YJL174W         | 0.3  |
| 32 | 6322684   | PIR1          | YKL164C         | 0.3  |
| 33 | 6324263   | SUN4          | YNL066W         | 0.2  |
| 34 | 6321496   | SPR3          | YGR059W         | 0.2  |
| 35 | 6322753   | CWP2          | YKL096W-A       | 0.2  |

Many of the secreted proteins were identified as cell wall proteins and proteins with GPI (glycosylphosphatidyl inositol) anchor. Abundantly secreted proteins were determined by PAI (protein abundance index) (Rappsilber et al., *Genome Res.* 12:1231-45 (2002)) which could be proportional to the number of proteins secreted. Based on this analysis, twenty of the abundantly secreted proteins were selected.

Figure 17A:
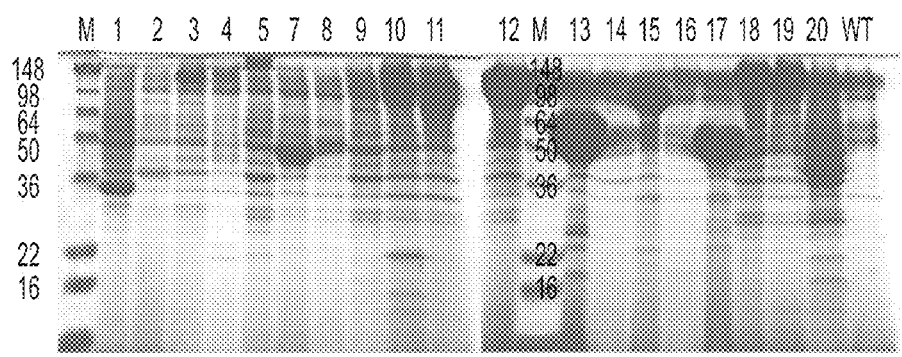
Figure 17B:
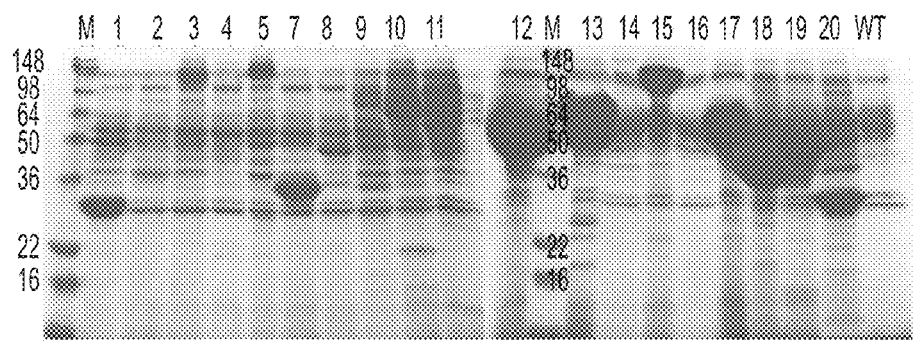

The genes of the 19 abundantly secreted proteins were amplified from genomic DNA using 19 different sense primers (SEQ ID NO: 35) and antisense primers (SEQ ID NO: 36). 5' and 3' ends of the amplified DNA fragments contained a stretch of homologous sequence with a part of the GAL10 promoter and the GALT terminator, respectively, for in vivo recombination with a EcoRI-SalI digested YEGα-HIR525, as described above. Yeast transformants were easily obtained by the transformation of both linearized vector and PCR fragment through in vivo recombination. Twenty different transformants obtained from 19 different PCR fragments were cultivated in YPDG (1% yeast extract, 2% peptone, 1% glucose, and 1% galactose) media. Three hundred microliters of each culture supernatant was concentrated with acetone. Each acetone-concentrated culture supernatant was analyzed in SDS-PAGE as shown in FIG. 17A.

To distinguish poor candidates from good candidate SFPs, the secretion level of the abundantly secreted proteins from a strong promoter was determined compared to wild-type protein secretion levels. Compared to the wild-type protein secretion levels shown in lane WT of FIG. 17A, a subset (eleven) of the tested proteins, expressed using the strong GAL10 promoter, showed extraordinary strong bands, suggesting over-secretion into the culture supernatant. Glycosidase, Endo-H treatment of each sample resulted in the correct protein sizes expected from the amino acid sequence of each protein (FIG. 17B) demonstrating that most of the over-secreted proteins were glycosylated. Eleven (11) of the 19 selected abundantly secreted proteins BGL2 (SEQ ID NO: 80), GAS3 (SEQ ID NO: 81), GAS5 (SEQ ID NO: 82), PST1 (SEQ ID NO: 83), SCW4 (SEQ ID NO: 84), SCW10 (SEQ ID NO: 85), SIMI (SEQ ID NO: 86), UTH1 (SEQ ID NO: 87), YGP1 (SEQ ID NO: 88), YPS1 (SEQ ID NO: 89), and ZPS1 (SEQ ID NO: 90) were tested as candidate SFPs for the secretion of heterologous proteins. The 11 proteins were encoded by the following polynucleotides: BGL2 (SEQ ID NO: 62), GAS3 (SEQ ID NO: 63), GAS5 (SEQ ID NO: 64), PST1 (SEQ ID NO: 65), SCW4 (SEQ ID NO: 66), SCW10 (SEQ ID NO: 67), SIM1 (SEQ ID NO: 68), UTH1 (SEQ ID NO: 69), YGP1 (SEQ ID NO: 70), YPS1 (SEQ ID NO: 71) and ZPS1 (SEQ ID NO: 72).

Vectors for expression of fusion proteins were constructed using open reading frames (OFRs) of polynucleotides encoding the 11 over-secreted proteins each fused to EXD4. Eleven fusion proteins were tested for their level of secretion into the culture supernatant. YGa-ORF vectors were recovered from each transformant producing the respective proteins in FIG. 17. For the construction of each fusion protein expression vector, 11 PCR fragments were amplified from eleven YGa-ORF vectors containing different ORFs using primer GAL100 (SEQ ID NO: 10) and 11 different antisense primers (SEQ ID NO: 37). The 5' and 3' ends of amplified DNA fragments contained a stretch of homologous sequence with the GAL10 promoter and exendin-4, respectively. The eleven PCR fragments and the exendin-4 amplified from YGaT92-EXD4 with primers EXD-F (SEQ ID NO: 46) and GT50R (SEQ ID NO: 14) were used as templates for the 11 different overlap extension PCRs using primers, GAL100 (SEQ ID NO: 10) and GT50R (SEQ ID NO: 14), respectively. Each extended PCR fragment was transformed with an EcoRI-SalI digested YEGα-HIR525, as described above. Two transformants from each transformation were cultivated in YPDG (1% yeast extract, 2% peptone, 1% glucose and 1% galactose) for 40 hours. A 0.6 ml sample from supernatant was concentrated using 0.4 ml of acetone and analyzed by SDS-PAGE, as shown in FIG. 18. Six fusion proteins (GAS3-EXD4, GAS5-EXD4, PST1-EXD4, SCW4-EXD4, YGP1-EXD4, and YPS1-EXD4) were found to be efficiently secreted into extracellular medium.

Example 5 showed that abundantly secreted proteins selected from yeast secretome were effective as secretion fusion partners for the secretory production of recombinant proteins. Although Example 5 used yeast secreted proteins, the secreted polypeptides of any organism, such as those described throughout the specification, may be used. As shown in this example, the screening method of the invention is an efficient way to identify SFPs, as it narrowed the possible candidate SFPs from 35 secreted proteins to 11, six of which proved to be effective SFPs Example 6

Determination of the Optimal Size of SCW4 Gene as a Fusion Partner

Figure 19A:
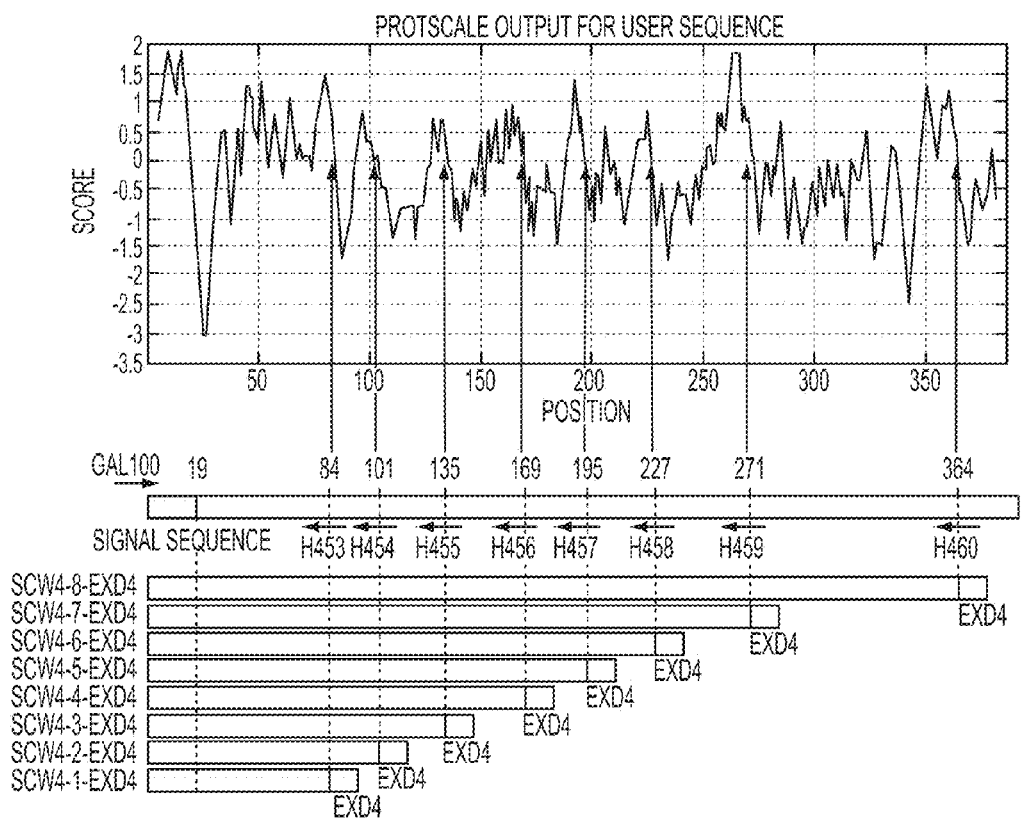
Figure 19B:
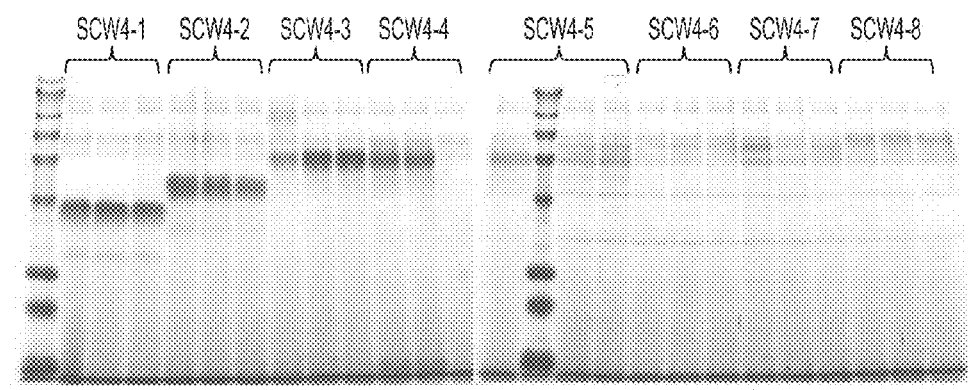

This example demonstrates the determination of the optimal size of SCW4 as a fusion partner for the secretion of a target proteins, e.g., exendin-4. Eight SCW4 deletion clones were constructed based on Kyte-Doolittle hydropathy analysis (FIG. 19A). The eight SCW4 fragments were amplified with GAL100 (SEQ ID NO: 10) and eight different antisense primers H453-H460 (SEQ ID NOs: 47-54) which each contained a 6 Histidine sequence. The amplified fragments were fused with EXD4 gene amplified from YGaT92-EXD4 with sense primer (SEQ ID NO: 55) and GT50R (SEQ ID NO: 14) by overlap extension PCRs using primers, GAL100 (SEQ ID NO: 10) and GT50R (SEQ ID NO: 14), respectively. Each extended PCR fragment was transformed with an EcoRI-SalI digested YEGα-HIR525 as described in the previous examples. Three colonies of 8 different transformants were cultivated in YPDG (1% yeast extract, 2% peptone, 1% glucose, and 1% galactose) media. Ten (10) microliter of culture broth for each sample was directly analyzed in SDS-PAGE (without concentration). As shown in FIG. 19B, SCW4-1, SCW4-2, SCW4-3 and SCW4-4 containing different C-terminal fragments of SCW4 showed strong activities as fusion partners for the secretion of EXD4. The optimal size of SCW4 as a fusion partner for EXD4 was shown to be less than 169 amino acids of the whole SCW4 protein (380 amino acids).

A recombinant yeast strain transformed with the YGaSCW4-1-EXD4 (FIG. 30) and YGaSCW4-3-EXD4 (FIG. 31) were cultured in a 5-L jar fermentor by fed-batch culture to be evaluated for the ability to induce the secretory production of fusion proteins. After a culture period of about 48 hrs, the culture reached an OD600 of about 130. 10 µl of the medium was collected at the given time points and assessed for secreted proteins by SDS-PAGE (FIG. 20). Compared to standard protein bands, the secreted SCW4-1-EXD4 (SEQ ID NO: 60) and SCW4-3-EXD4 (SEQ ID NO: 61) were estimated to be over 3 grams per liter.

To test the robustness of SCW4 protein against enterokinase, the fermentation broths were digested with enterokinase for 1 hr at 37° C. without purification. Fusion proteins were correctly divided into SCW4 protein and exendin-4 peptide, as shown in FIG. 21. Therefore, these results show that the modified SCW4 fusion partners considerably increased the yield of exendin-4 protein and simplified the purification process.

Figure 22A:
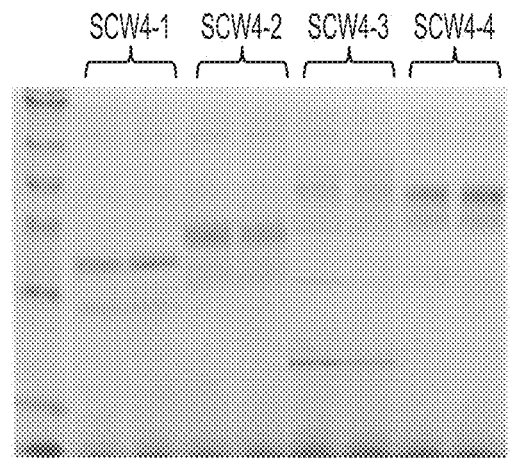
Figure 22B:
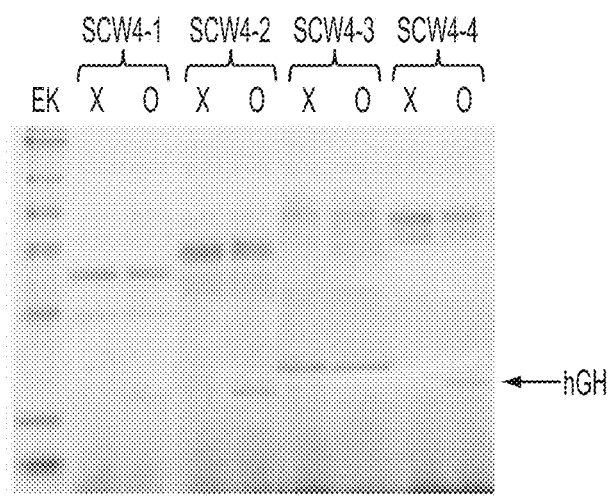

The effectiveness of SCW4 as a general fusion partner for other proteins was tested. SCW4-1, SCW4-2, SCW4-3 and SCW4-4 were applied for secretory production of human growth hormone (hGH). The hGH gene was amplified with sense primer (SEQ ID NO: 56) and antisense primer (SEQ ID NO: 57). This fragment was flanked with a stretch of 6 histidine and a GALT terminator sequence. PCR amplified SCW4-1, -2, -3 and -4 fragments were fused with the hGH gene by overlap extension PCRs using primers, GAL100 (SEQ ID NO: 10) and GT50R (SEQ ID NO: 14), respectively. Each extended PCR fragment was transformed with an EcoRI-SalI digested YEGα-HIR525 as described above. Two colonies of 4 different transformations were cultivated in YPDG (1% yeast extract, 2% peptone, 1% glucose, and 1% galactose) media. Ten (10) microliters of culture broth of each sample was directly analyzed in SDS-PAGE (without concentration). As shown in FIG. 22A, different sized SCW4-hGH fusion protein bands were detected for each sample. To confirm the fusion protein, the culture supernatants were incubated with enterokinase for 1 hr at 37° C. to cleave the fusion proteins. The correct size hGH was retrieved from SCW4-1-hGH, SCW4-2-hGH and SCW4-4-hGH (FIG. 22B). Thus, the N-terminal fragments of SCW4 showed strong activities as fusion partners for the secretion of hGH, as well as EXD4.

A recombinant yeast strain transformed with the YGaSCW4-2-hGH (FIG. 32) was cultured in a 5-L jar fermentor by fed-batch culture to be evaluated for its ability to induce the secretory production of fusion proteins. After a culture period of about 48 hrs, 10 μl of the medium was collected at the given time points and assessed for secreted proteins by SDS-PAGE (FIG. 23). Compared to standard protein bands, the secreted SCW4-2-hGH (SEQ ID NO: 73) was estimated to be over 3 grams per liter.

Thus, the results of Example 6 show that SCW4 and fragments thereof are effective as fusion partners for recombinant expression of target proteins, and may be used to produce large quantities of target proteins.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

What is claimed is:

1. A method of identifying a secretion fusion partner (SFP), said method comprising:

(i) transforming a first yeast host cell with a construct comprising a heterologous promoter operably linked to a polynucleotide encoding a secreted polypeptide;

(ii) determining said secreted polypeptide to be over-secreted when the secretion level of said secreted polypeptide linked to the heterologous promoter is higher than that of said secreted polypeptide linked to a natural promoter thereof;

(iii) transforming a second yeast host cell with a construct comprising a first polynucleotide encoding a target polypeptide and a second polynucleotide encoding the polypeptide determined to be over-secreted in step (ii), wherein said first and second polynucleotides are in any order relative to each other and are in the same frame;

(iv) culturing said second yeast host cell under conditions wherein said construct expresses a fusion polypeptide of said target polypeptide and said over-secreted polypeptide; and (v) determining whether said fusion polypeptide is secreted into the culture medium; thereby identifying whether said over-secreted polypeptide is a SFP, wherein the SFP comprises a signal peptide, a hydrophilic domain, or a signal peptide and a hydrophilic domain, and the SFP comprises an amino acid sequence selected from the group consisting of amino acids 1-84 of SEQ ID NO: 84, amino acids 1-101 of SEQ ID NO: 84, amino acids 1-135 of SEQ ID NO: 84, amino acids 1-169 of SEQ ID NO: 84, amino acids 1-195 of SEQ ID NO: 84, amino acids 1-227 of SEQ ID NO: 84, amino acids 1-271 of SEQ ID NO: 84, amino acids 1-364 of SEQ ID NO: 84; or the SFP is selected from the group consisting of BGL2 (SEQ ID NO: 80), GAS3 (SEQ ID NO: 81), GAS5 (SEQ ID NO: 82), PST1 (SEQ ID NO: 83), SCW4 (SEQ ID NO: 84), SCW10 (SEQ ID NO: 85), SIM1 (SEQ ID NO: 86), UTH1 (SEQ ID NO: 87), YGP1 (SEQ ID NO: 88), YPS1 (SEQ ID NO: 89), and ZPS1 (SEQ ID NO: 90); and wherein the target polypeptide is selected from the group consisting of an interleukin, a coagulation factor, an interferon-α, -β or -γ, a granulocyte-colony stimulating factor, a granulocyte macrophage-colony stimulating factor, a tissue growth factor, an epithelial growth factor, a TGFα, a TGFβ, an epidermal growth factor, a platelet-derived growth factor, a fibroblast growth factor, a follicle stimulating hormone, a thyroid stimulating hormone, an antidiuretic hormone, a pigmentary hormone, a parathyroid hormone, a luteinizing hormone-releasing hormone, a carbohydrate-specific enzyme, a proteolytic enzyme, a lipase, an oxidoreductase, a transferase, a hydrolase, a lyase, an isomerase, a ligase, an immunoglobulin, a cytokine receptor, a lactoferrin, a phospholipase A2-activating protein, an insulin, a tumor necrosis factor, a calcitonin, a calcitonin gene related peptide, an enkephalin, a somatomedin, an erythropoietin, a hypothalamic releasing factor, a prolactin, a chorionic gonadotropin, a tissue plasminogen activator, a growth hormone releasing peptide, a thymic humoral factor, an anticancer peptide, and an antibiotic peptide.

2. The method of claim 1, wherein said secreted polypeptide is selected as being abundantly expressed in a secretome.

3. The method of claim 2, wherein said secretome is isolated from yeast, bacteria, plants or animals.

4. The method of claim 1, further comprising determining an optimal size of said SFP for secretion of said fusion polypeptide or a second fusion polypeptide, wherein said optimal size is determined by deletion analysis of said SFP.

5. The method of claim 1, wherein said heterologous promoter is prokaryotic, eukaryotic or viral.

6. The method of claim 5, wherein said heterologous promoter is selected from the group consisting of bacteriophage lambda PR, bacteriophage lambda PL, lambda II, *E. coli* trp, *E. coli* recA, *E. coli* heat shock, *E. coli* lacZ, SV40 early, yeast GAPDH, PGK, ADH, PHO5, TEF, GAL1, GAL10, mouse mammary tumor virus, long terminal repeat of human immunodeficiency virus, maloney virus, cytomegalovirus immediate early, Epstein Barr virus, Rous sarcoma virus, human actin, human myosin, human hemoglobin, human muscle creatine, and human metallothionein.

7. The method of claim 1, wherein said secreted polypeptide is glycosylated.

8. The method of claim 1, wherein said first yeast host cell is a selected from the group consisting of *Candida, Debaryomyces, Hansenula, Kluyveromyces, Pichia, Schizosaccharomyces, Yarrowia, Saccharomyces, Schwanniomyces*, and *Arxula*.

9. The method of claim 8, wherein said first yeast host cell is selected from the group consisting of *Candida utilis, Candida boidinii, Candida albicans, Kluyveromyces lactis, Pichia pastoris, Pichia stipitis, Schizosaccharomyces pombe, Saccharomyces cerevisiae, Hansenula polymorpha, Yarrowia lipolytica, Schwanniomyces occidentalis*, and *Arxula adeninivorans*.

10. The method of claim 1, wherein said second yeast host cell is a selected from the group consisting of *Candida, Debaryomyces, Hansenula, Kluyveromyces, Pichia, Schizosaccharomyces, Yarrowia, Saccharomyces, Schwanniomyces*, and *Arxula*.

11. The method of claim 10, wherein said second yeast host cell is selected from the group consisting of *Candida utilis, Candida boidinii, Candida albicans, Kluyveromyces lactis, Pichia pastoris, Pichia stipitis, Schizosaccharomyces pombe, Saccharomyces cerevisiae, Hansenula polymorpha, Yarrowia lipolytica, Schwanniomyces occidentalis*, and *Arxula adeninivorans*.

12. The method of claim 1, wherein the target polypeptide is selected from the group consisting of human interleukin-2 (hIL-2), exendin-3, exendin-4 (EXD4), glucagon-like-peptide-1 (GLP-1), parathyroid hormone (PTH), human interleukin-1β, human interleukin-6, human interleukin-32α, -32β or -32γ, Factor VII, Factor VIII, Factor IX, human serum albumin, human interferon-α, -β or -γ, human granulocyte-colony stimulating factor, human granulocyte macrophage-colony stimulating factor, human growth hormone (hGH), human platelet-derived growth factor, human basic fibroblast growth factor, human epidermal growth factor (EGF), human insulin-like growth factor, human nerve growth factor, human transforming growth factor β-1, human follicle stimulating hormone, glucose oxidase, glucodase, galactosidase, glucocerebrosidase, glucuronidase, asparaginase, arginase, arginine deaminase, peroxide dismutase, endotoxinase, catalase, chymotrypsin, uricase, adenosine diphosphatase, tyrosinase, bilirubin oxidase, bovine galactose-1-phosphate uridyltransferase, jellyfish green fluorescent protein, *Candida antarctica* lipase B, *Candida rugosa* lipase, fungal chloroperoxidase, β-galactosidase, resolvase, α-galactosidase, β-glucosidase, trehalose synthase, cyclodextrin glycosyl transferase, xylanase, phytase, human lactoferrin, human erythropoietin, human paraoxonase, human growth differentiation factor 15, human galectin-3 binding protein, human serine protease inhibitor, Kunitz type 2, human Janus kinase 2, human fms-like tyrosine kinase 3 ligand, human YM1 & 2, human CEMI, human diacylglycerol acyltransferase, human leptin, human mL259, human proteinase 3, human lysozyme, human DEAD box protein 41, human etoposide induced protein 24, mouse caspase1, bovine angiogenin, and earthworm lumbrokinase.

* * * * *

SEQUENCE LISTING

```
<160> NUMBER OF SEQ ID NOS: 91

<210> SEQ ID NO 1
<211> LENGTH: 265
<212> TYPE: PRT
<213> ORGANISM: Saccharomyces sp.

<400> SEQUENCE: 1

Met Val Phe Gly Gln Leu Tyr Ala Leu Phe Ile Phe Thr Leu Ser Cys
1               5                   10                  15

Cys Ile Ser Lys Thr Val Gln Ala Asp Ser Ser Lys Glu Ser Ser Ser
            20                  25                  30

Phe Ile Ser Phe Asp Lys Glu Ser Asn Trp Asp Thr Ile Ser Thr Ile
        35                  40                  45

Ser Ser Thr Ala Asp Val Ile Ser Ser Val Asp Ser Ala Ile Ala Val
    50                  55                  60

Phe Glu Phe Asp Asn Phe Ser Leu Leu Asp Asn Leu Met Ile Asp Glu
65                  70                  75                  80

Glu Tyr Pro Phe Phe Asn Arg Phe Phe Ala Asn Asp Val Ser Leu Thr
                85                  90                  95

Val His Asp Asp Ser Pro Leu Asn Ile Ser Gln Ser Leu Ser Pro Ile
            100                 105                 110

Met Glu Gln Phe Thr Val Asp Glu Leu Pro Glu Ser Ala Ser Asp Leu
        115                 120                 125

Leu Tyr Glu Tyr Ser Leu Asp Asp Lys Ser Ile Val Leu Phe Lys Phe
    130                 135                 140

Thr Ser Asp Ala Tyr Asp Leu Lys Lys Leu Asp Glu Phe Ile Asp Ser
145                 150                 155                 160

Cys Leu Ser Phe Leu Glu Asp Lys Ser Gly Asp Asn Leu Thr Val Val
                165                 170                 175

Ile Asn Ser Leu Gly Trp Ala Phe Glu Asp Glu Asp Gly Asp Asp Glu
            180                 185                 190

Tyr Ala Thr Glu Glu Thr Leu Ser His His Asp Asn Asn Lys Gly Lys
        195                 200                 205

Glu Gly Asp Asp Asp Ile Leu Ser Ser Ile Trp Thr Glu Gly Leu Leu
    210                 215                 220

Met Cys Leu Ile Val Ser Ala Leu Leu Leu Phe Ile Leu Ile Val Ala
225                 230                 235                 240

Leu Ser Trp Ile Ser Asn Leu Asp Ile Thr Tyr Gly Ala Leu Glu Lys
                245                 250                 255

Ser Thr Asn Pro Ile Lys Lys Asn Asn
            260                 265

<210> SEQ ID NO 2
<211> LENGTH: 24
<212> TYPE: DNA
<213> ORGANISM: Artificial Sequence
<220> FEATURE:
```

<223> OTHER INFORMATION: Synthetic primer T9F

<400> SEQUENCE: 2
ggatccatgg tgttcggtca gctg                                          24

<210> SEQ ID NO 3
<211> LENGTH: 39
<212> TYPE: DNA
<213> ORGANISM: Artificial Sequence
<220> FEATURE:
<223> OTHER INFORMATION: Synthetic primer H159

<400> SEQUENCE: 3
cactccgttc aagtcgactt aattgttttt ttttattgg                          39

<210> SEQ ID NO 4
<211> LENGTH: 41
<212> TYPE: DNA
<213> ORGANISM: Artificial Sequence
<220> FEATURE:
<223> OTHER INFORMATION: Synthetic primer H160

<400> SEQUENCE: 4
cactccgttc aagtcgactt aatcatcgtc gccttcttta c                       41

<210> SEQ ID NO 5
<211> LENGTH: 39
<212> TYPE: DNA
<213> ORGANISM: Artificial Sequence
<220> FEATURE:
<223> OTHER INFORMATION: Synthetic primer H161

<400> SEQUENCE: 5
cactccgttc aagtcgactt actcttctgt tgcatattc                          39

<210> SEQ ID NO 6
<211> LENGTH: 40
<212> TYPE: DNA
<213> ORGANISM: Artificial Sequence
<220> FEATURE:
<223> OTHER INFORMATION: Synthetic primer H162

<400> SEQUENCE: 6
cactccgttc aagtcgactt aaaaagccca accaagagag                         40

<210> SEQ ID NO 7
<211> LENGTH: 32
<212> TYPE: DNA
<213> ORGANISM: Artificial Sequence
<220> FEATURE:
<223> OTHER INFORMATION: Synthetic primer H205

<400> SEQUENCE: 7
atcggtcgac ttagtcgcca gatttatctt cc                                 32

<210> SEQ ID NO 8
<211> LENGTH: 37
<212> TYPE: DNA
<213> ORGANISM: Artificial Sequence
<220> FEATURE:
<223> OTHER INFORMATION: Synthetic primer H204

<400> SEQUENCE: 8
atcggtcgac ttaatcatct aaggagtatt catatag                            37

```
<210> SEQ ID NO 9
<211> LENGTH: 33
<212> TYPE: DNA
<213> ORGANISM: Artificial Sequence
<220> FEATURE:
<223> OTHER INFORMATION: Synthetic primer H203

<400> SEQUENCE: 9
atcggtcgac ttaatcgtca tgaacagtta aac                                    33

<210> SEQ ID NO 10
<211> LENGTH: 21
<212> TYPE: DNA
<213> ORGANISM: Artificial Sequence
<220> FEATURE:
<223> OTHER INFORMATION: Synthetic primer GAL100

<400> SEQUENCE: 10
gtatatggtg gtaatgccat g                                                 21

<210> SEQ ID NO 11
<211> LENGTH: 38
<212> TYPE: DNA
<213> ORGANISM: Artificial Sequence
<220> FEATURE:
<223> OTHER INFORMATION: Synthetic primer H121

<400> SEQUENCE: 11
tcttttatct aaggcgagat catcgtcgcc ttctttac                               38

<210> SEQ ID NO 12
<211> LENGTH: 38
<212> TYPE: DNA
<213> ORGANISM: Artificial Sequence
<220> FEATURE:
<223> OTHER INFORMATION: Synthetic primer IL2F

<400> SEQUENCE: 12
ctcgccttag ataaaagagc acctacttca agttctac                               38

<210> SEQ ID NO 13
<211> LENGTH: 39
<212> TYPE: DNA
<213> ORGANISM: Artificial Sequence
<220> FEATURE:
<223> OTHER INFORMATION: Synthetic primer IL2R

<400> SEQUENCE: 13
gtcactccgt tcaagtcgac ctaagttagt gttgagatg                              39

<210> SEQ ID NO 14
<211> LENGTH: 50
<212> TYPE: DNA
<213> ORGANISM: Artificial Sequence
<220> FEATURE:
<223> OTHER INFORMATION: Synthetic primer GT50R

<400> SEQUENCE: 14
gtcattatta aatatatata tatatatatt gtcactccgt tcaagtcgac                  50

<210> SEQ ID NO 15
<211> LENGTH: 36
<212> TYPE: DNA
<213> ORGANISM: Artificial Sequence
<220> FEATURE:
<223> OTHER INFORMATION: Synthetic primer H120
```

<400> SEQUENCE: 15
tcttttatct aaggcgagct cttctgttgc atattc                          36

<210> SEQ ID NO 16
<211> LENGTH: 37
<212> TYPE: DNA
<213> ORGANISM: Artificial Sequence
<220> FEATURE:
<223> OTHER INFORMATION: Synthetic primer H119

<400> SEQUENCE: 16
tcttttatct aaggcgagaa aagcccaacc aagagag                         37

<210> SEQ ID NO 17
<211> LENGTH: 44
<212> TYPE: DNA
<213> ORGANISM: Artificial Sequence
<220> FEATURE:
<223> OTHER INFORMATION: Synthetic primer HDK-R

<400> SEQUENCE: 17
gtcatcgtca ccgtggtgat ggtgatgatg gctcaaagtc tctt                 44

<210> SEQ ID NO 18
<211> LENGTH: 42
<212> TYPE: DNA
<213> ORGANISM: Artificial Sequence
<220> FEATURE:
<223> OTHER INFORMATION: Synthetic primer HDK-F

<400> SEQUENCE: 18
caccacggtg acgatgacga taaacatggt gaaggtactt tc                   42

<210> SEQ ID NO 19
<211> LENGTH: 37
<212> TYPE: DNA
<213> ORGANISM: Artificial Sequence
<220> FEATURE:
<223> OTHER INFORMATION: Synthetic primer EXD-R

<400> SEQUENCE: 19
gtcactccgt tcaagtcgac ttaagatggt ggtggag                         37

<210> SEQ ID NO 20
<211> LENGTH: 30
<212> TYPE: DNA
<213> ORGANISM: Artificial Sequence
<220> FEATURE:
<223> OTHER INFORMATION: Synthetic primer H307

<400> SEQUENCE: 20
gatgctttta ccatctaagg agtattcata                                 30

<210> SEQ ID NO 21
<211> LENGTH: 30
<212> TYPE: DNA
<213> ORGANISM: Artificial Sequence
<220> FEATURE:
<223> OTHER INFORMATION: Synthetic primer H306

<400> SEQUENCE: 21
tccttagatg gtaaaagcat cgttttgttc                                 30

<210> SEQ ID NO 22
<211> LENGTH: 30

<212> TYPE: DNA
<213> ORGANISM: Artificial Sequence
<220> FEATURE:
<223> OTHER INFORMATION: Synthetic primer H309

<400> SEQUENCE: 22
cgccagattt accttccaaa aacgataagc                               30

<210> SEQ ID NO 23
<211> LENGTH: 30
<212> TYPE: DNA
<213> ORGANISM: Artificial Sequence
<220> FEATURE:
<223> OTHER INFORMATION: Synthetic primer H308

<400> SEQUENCE: 23
tttttggaag gtaaatctgg cgacaatttg                               30

<210> SEQ ID NO 24
<211> LENGTH: 38
<212> TYPE: DNA
<213> ORGANISM: Artificial Sequence
<220> FEATURE:
<223> OTHER INFORMATION: Synthetic primer H221

<400> SEQUENCE: 24
ctcgccttag ataaaagagt tattaactct cttggttg                      38

<210> SEQ ID NO 25
<211> LENGTH: 54
<212> TYPE: DNA
<213> ORGANISM: Artificial Sequence
<220> FEATURE:
<223> OTHER INFORMATION: Synthetic primer LNK-R

<400> SEQUENCE: 25
cttttatcta aggcgaggcc agcagaggcc gaggcggcca cccttcttc ttta    54

<210> SEQ ID NO 26
<211> LENGTH: 36
<212> TYPE: DNA
<213> ORGANISM: Artificial Sequence
<220> FEATURE:
<223> OTHER INFORMATION: Synthetic primer H412

<400> SEQUENCE: 26
ctcgccttag ataaaagaca tggtgaaggt actttc                        36

<210> SEQ ID NO 27
<211> LENGTH: 36
<212> TYPE: DNA
<213> ORGANISM: Artificial Sequence
<220> FEATURE:
<223> OTHER INFORMATION: Synthetic primer H413

<400> SEQUENCE: 27
accaagagag ttaataacag atggtggtgg agcacc                        36

<210> SEQ ID NO 28
<211> LENGTH: 20
<212> TYPE: DNA
<213> ORGANISM: Artificial Sequence
<220> FEATURE:
<223> OTHER INFORMATION: Synthetic primer HL-F

<400> SEQUENCE: 28

-continued gttattaact ctcttggttg                                                    20

<210> SEQ ID NO 29
<211> LENGTH: 40
<212> TYPE: DNA
<213> ORGANISM: Artificial Sequence
<220> FEATURE:
<223> OTHER INFORMATION: Synthetic primer HL-GT50R

<400> SEQUENCE: 29
cactccgttc aagtcgactt agtggtgatg gtgatgatgg                              40

<210> SEQ ID NO 30
<211> LENGTH: 24
<212> TYPE: DNA
<213> ORGANISM: Artificial Sequence
<220> FEATURE:
<223> OTHER INFORMATION: Synthetic primer DDK-R

<400> SEQUENCE: 30
cttatcgtca tcgtcaccgt ggtg                                               24

<210> SEQ ID NO 31
<211> LENGTH: 37
<212> TYPE: DNA
<213> ORGANISM: Artificial Sequence
<220> FEATURE:
<223> OTHER INFORMATION: Synthetic primer H410

<400> SEQUENCE: 31
ggtgacgatg acgataagaa ctccgactcc gagtgtc                                 37

<210> SEQ ID NO 32
<211> LENGTH: 36
<212> TYPE: DNA
<213> ORGANISM: Artificial Sequence
<220> FEATURE:
<223> OTHER INFORMATION: Synthetic primer H411

<400> SEQUENCE: 32
cactccgttc aagtcgactt actatcatct cagctc                                  36

<210> SEQ ID NO 33
<211> LENGTH: 37
<212> TYPE: DNA
<213> ORGANISM: Artificial Sequence
<220> FEATURE:
<223> OTHER INFORMATION: Synthetic primer H310

<400> SEQUENCE: 33
ggtgacgatg acgataagtc tgtgagtgaa atacagc                                 37

<210> SEQ ID NO 34
<211> LENGTH: 38
<212> TYPE: DNA
<213> ORGANISM: Artificial Sequence
<220> FEATURE:
<223> OTHER INFORMATION: Synthetic primer H311

<400> SEQUENCE: 34
cactccgttc aagtcgactt actgggattt agctttag                                38

<210> SEQ ID NO 35
<211> LENGTH: 37
<212> TYPE: DNA
<213> ORGANISM: Artificial Sequence

```
<220> FEATURE:
<223> OTHER INFORMATION: Synthetic primer
<220> FEATURE:
<221> NAME/KEY: misc_feature
<222> LOCATION: (20)..(37)
<223> OTHER INFORMATION: n is a, c, g, or t

<400> SEQUENCE: 35
gaaaattcaa gaattcatgn nnnnnnnnnn nnnnnnn                              37

<210> SEQ ID NO 36
<211> LENGTH: 38
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (21)..(38)
<223> OTHER INFORMATION: n is a, c, g, or t

<400> SEQUENCE: 36
actccgttca agtcgactta nnnnnnnnnn nnnnnnnn                             38

<210> SEQ ID NO 37
<211> LENGTH: 36
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (19)..(36)
<223> OTHER INFORMATION: n is a, c, g, or t

<400> SEQUENCE: 37
gaaagtacct tcaccatgnn nnnnnnnnn nnnnnn                                36

<210> SEQ ID NO 38
<211> LENGTH: 798
<212> TYPE: DNA
<213> ORGANISM: Artificial Sequence
<220> FEATURE:
<223> OTHER INFORMATION: Modified yeast SFP1-91

<400> SEQUENCE: 38
atggtgttcg gtcagctgta tgcccttttc atcttcacgt tatcatgttg tatttccaaa      60
actgtgcaag cagattcatc caaggaaagc tcttccttta tttcgttcga caaagagagt     120
aactgggata ccatcagcac tatatcttca acggcagatg ttatatcatc cgttgacagt     180
gctatcgctg tttttgaatt tgacaatttc tcattattgg acaacttgat gattgacgaa     240
gaatacccat tcttcaatag attctttgcc aatgatgtca gtttaactgt tcatgacgat     300
tcgcctttga acatctctca atcattatct cccattatgg aacaatttac tgtggatgaa     360
ttacctgaaa gtgcctctga cttactatat gaatactcct tagatgataa agcatcgtt      420 tgttcaagt ttacctcgga tgcctacgat ttgaaaaaat tagatgaatt tattgattct     480
tgcttatcgt ttttggaaga taaatctggc gacaatttga ctgtggttat taactctctt     540
ggttgggctt tgaagatga agatggtgac gatgaatatg caacagaaga gactttgagc     600
catcatgata caacaaggg taaagaaggc gacgatgata ttttaagctc catctggact     660
gaaggactac taatgtgttt aatagtttct gcgttgctat tgttcatttt gattgttgca     720
ctttcttgga tatctaattt ggatatcaca tatggtgcgt tggaaaaatc aacaaaccca     780
```
ataaaaaaaa acaattaa 798

<210> SEQ ID NO 39
<211> LENGTH: 639
<212> TYPE: DNA
<213> ORGANISM: Artificial Sequence
<220> FEATURE:
<223> OTHER INFORMATION: Modified yeast SFP1-92

<400> SEQUENCE: 39

| | |
|---|---|
| atggtgttcg gtcagctgta tgcccttttc atcttcacgt tatcatgttg tatttccaaa | 60 |
| actgtgcaag cagattcatc caaggaaagc tcttccttta tttcgttcga caaagagagt | 120 |
| aactgggata ccatcagcac tatatcttca acggcagatg ttatatcatc cgttgacagt | 180 |
| gctatcgctg tttttgaatt tgacaatttc tcattattgg acaacttgat gattgacgaa | 240 |
| gaatacccat tcttcaatag attctttgcc aatgatgtca gtttaactgt tcatgacgat | 300 |
| tcgcctttga acatctctca atcattatct cccattatgg aacaatttac tgtggatgaa | 360 |
| ttacctgaaa gtgcctctga cttactatat gaatactcct tagatgataa aagcatcgtt | 420 |
| ttgttcaagt ttacctcgga tgcctacgat ttgaaaaaat tagatgaatt tattgattct | 480 |
| tgcttatcgt ttttggaaga taaatctggc gacaatttga ctgtggttat taactctctt | 540 |
| ggttgggctt tgaagatga agatggtgac gatgaatatg caacagaaga gactttgagc | 600 |
| catcatgata caacaaggg taaagaaggc gacgatgat | 639 |

<210> SEQ ID NO 40
<211> LENGTH: 591
<212> TYPE: DNA
<213> ORGANISM: Artificial Sequence
<220> FEATURE:
<223> OTHER INFORMATION: Modified yeast SFP1-93

<400> SEQUENCE: 40

| | |
|---|---|
| atggtgttcg gtcagctgta tgcccttttc atcttcacgt tatcatgttg tatttccaaa | 60 |
| actgtgcaag cagattcatc caaggaaagc tcttccttta tttcgttcga caaagagagt | 120 |
| aactgggata ccatcagcac tatatcttca acggcagatg ttatatcatc cgttgacagt | 180 |
| gctatcgctg tttttgaatt tgacaatttc tcattattgg acaacttgat gattgacgaa | 240 |
| gaatacccat tcttcaatag attctttgcc aatgatgtca gtttaactgt tcatgacgat | 300 |
| tcgcctttga acatctctca atcattatct cccattatgg aacaatttac tgtggatgaa | 360 |
| ttacctgaaa gtgcctctga cttactatat gaatactcct tagatgataa aagcatcgtt | 420 |
| ttgttcaagt ttacctcgga tgcctacgat ttgaaaaaat tagatgaatt tattgattct | 480 |
| tgcttatcgt ttttggaaga taaatctggc gacaatttga ctgtggttat taactctctt | 540 |
| ggttgggctt tgaagatga agatggtgac gatgaatatg caacagaaga g | 591 |

<210> SEQ ID NO 41
<211> LENGTH: 552
<212> TYPE: DNA
<213> ORGANISM: Artificial Sequence
<220> FEATURE:
<223> OTHER INFORMATION: Modified yeast SFP1-94

<400> SEQUENCE: 41

| | |
|---|---|
| atggtgttcg gtcagctgta tgcccttttc atcttcacgt tatcatgttg tatttccaaa | 60 |
| actgtgcaag cagattcatc caaggaaagc tcttccttta tttcgttcga caaagagagt | 120 |
| aactgggata ccatcagcac tatatcttca acggcagatg ttatatcatc cgttgacagt | 180 |

```
gctatcgctg tttttgaatt tgacaatttc tcattattgg acaacttgat gattgacgaa      240
gaatacccat tcttcaatag attctttgcc aatgatgtca gtttaactgt tcatgacgat      300
tcgcctttga acatctctca atcattatct cccattatgg aacaatttac tgtggatgaa      360
ttacctgaaa gtgcctctga cttactatat gaatactcct tagatgataa aagcatcgtt      420
ttgttcaagt ttacctcgga tgcctacgat ttgaaaaaat tagatgaatt tattgattct      480
tgcttatcgt ttttggaaga taaatctggc gacaatttga ctgtggttat taactctctt      540
ggttgggctt tt                                                          552
```

<210> SEQ ID NO 42
<211> LENGTH: 639
<212> TYPE: DNA
<213> ORGANISM: Artificial Sequence
<220> FEATURE:
<223> OTHER INFORMATION: Modified yeast SFP1-921

<400> SEQUENCE: 42

```
atggtgttcg gtcagctgta tgccttttc atcttcacgt tatcatgttg tatttccaaa       60
actgtgcaag cagattcatc caaggaaagc tcttccttta tttcgttcga caaagagagt      120
aactgggata ccatcagcac tatatcttca acggcagatg ttatatcatc cgttgacagt      180
gctatcgctg tttttgaatt tgacaatttc tcattattgg acaacttgat gattgacgaa      240
gaatacccat tcttcaatag attctttgcc aatgatgtca gtttaactgt tcatgacgat      300
tcgcctttga acatctctca atcattatct cccattatgg aacaatttac tgtggatgaa      360
ttacctgaaa gtgcctctga cttactatat gaatactcct tagatggtaa aagcatcgtt      420
ttgttcaagt ttacctcgga tgcctacgat ttgaaaaaat tagatgaatt tattgattct      480
tgcttatcgt ttttggaaga taaatctggc gacaatttga ctgtggttat taactctctt      540
ggttgggctt tgaagatga agatggtgac gatgaatatg caacagaaga gactttgagc      600
catcatgata acaacaaggg taaagaaggc gacgatgat                             639
```

<210> SEQ ID NO 43
<211> LENGTH: 639
<212> TYPE: DNA
<213> ORGANISM: Artificial Sequence
<220> FEATURE:
<223> OTHER INFORMATION: Modified yeast SFP1-922

<400> SEQUENCE: 43

```
atggtgttcg gtcagctgta tgccttttc atcttcacgt tatcatgttg tatttccaaa       60
actgtgcaag cagattcatc caaggaaagc tcttccttta tttcgttcga caaagagagt      120
aactgggata ccatcagcac tatatcttca acggcagatg ttatatcatc cgttgacagt      180
gctatcgctg tttttgaatt tgacaatttc tcattattgg acaacttgat gattgacgaa      240
gaatacccat tcttcaatag attctttgcc aatgatgtca gtttaactgt tcatgacgat      300
tcgcctttga acatctctca atcattatct cccattatgg aacaatttac tgtggatgaa      360
ttacctgaaa gtgcctctga cttactatat gaatactcct tagatgataa aagcatcgtt      420
ttgttcaagt ttacctcgga tgcctacgat ttgaaaaaat tagatgaatt tattgattct      480
tgcttatcgt ttttggaagg taaatctggc gacaatttga ctgtggttat taactctctt      540
ggttgggctt tgaagatga agatggtgac gatgaatatg caacagaaga gactttgagc      600
catcatgata acaacaaggg taaagaaggc gacgatgat                             639
```

<210> SEQ ID NO 44
<211> LENGTH: 639
<212> TYPE: DNA
<213> ORGANISM: Artificial Sequence
<220> FEATURE:
<223> OTHER INFORMATION: Modified yeast SFP1-923

<400> SEQUENCE: 44

```
atggtgttcg gtcagctgta tgcccttttc atcttcacgt tatcatgttg tatttccaaa      60
actgtgcaag cagattcatc caaggaaagc tcttcctttta tttcgttcga caaagagagt   120
aactgggata ccatcagcac tatatcttca acggcagatg ttatatcatc cgttgacagt    180
gctatcgctg tttttgaatt tgacaatttc tcattattgg acaacttgat gattgacgaa    240
gaatacccat tcttcaatag attctttgcc aatgatgtca gtttaactgt tcatgacgat   300
tcgcctttga acatctctca atcattatct cccattatgg aacaatttac tgtggatgaa    360
ttacctgaaa gtgcctctga cttactatat gaatactcct tagatggtaa aagcatcgtt    420
ttgttcaagt ttacctcgga tgcctacgat ttgaaaaaat tagatgaatt tattgattct   480
tgcttatcgt ttttggaagg taaatctggc gacaatttga ctgtggttat taactctctt   540
ggttgggctt ttgaagatga agatggtgac gatgaatatg caacagaaga gactttgagc   600
catcatgata acaacaaggg taaagaaggc gacgatgat                           639
```

<210> SEQ ID NO 45
<211> LENGTH: 114
<212> TYPE: DNA
<213> ORGANISM: Artificial Sequence
<220> FEATURE:
<223> OTHER INFORMATION: Synthetic modified HL domain

<400> SEQUENCE: 45

```
gttattaact ctcttggttg ggcttttgaa gatgaagatg gtgacgatga atatgcaaca      60
gaagagactt tgagccatca tgataacaac aagggtaaag aaggcgacga tgat           114
```

<210> SEQ ID NO 46
<211> LENGTH: 18
<212> TYPE: DNA
<213> ORGANISM: Artificial Sequence
<220> FEATURE:
<223> OTHER INFORMATION: Synthetic primer EXD-F

<400> SEQUENCE: 46

```
catggtgaag gtactttc                                                    18
```

<210> SEQ ID NO 47
<211> LENGTH: 37
<212> TYPE: DNA
<213> ORGANISM: Artificial Sequence
<220> FEATURE:
<223> OTHER INFORMATION: Synthetic primer

<400> SEQUENCE: 47

```
cgtggtgatg gtgatgatga gcagcagcgg tagctac                               37
```

<210> SEQ ID NO 48
<211> LENGTH: 37
<212> TYPE: DNA
<213> ORGANISM: Artificial Sequence
<220> FEATURE:
<223> OTHER INFORMATION: Synthetic primer

<400> SEQUENCE: 48
cgtggtgatg gtgatgatgg gaggctggag atgcggc    37

<210> SEQ ID NO 49
<211> LENGTH: 37
<212> TYPE: DNA
<213> ORGANISM: Artificial Sequence
<220> FEATURE:
<223> OTHER INFORMATION: Synthetic primer

<400> SEQUENCE: 49
cgtggtgatg gtgatgatga cctctgacac cagaggc    37

<210> SEQ ID NO 50
<211> LENGTH: 37
<212> TYPE: DNA
<213> ORGANISM: Artificial Sequence
<220> FEATURE:
<223> OTHER INFORMATION: Synthetic primer

<400> SEQUENCE: 50
cgtggtgatg gtgatgatgg tacaatctaa tgactgg    37

<210> SEQ ID NO 51
<211> LENGTH: 38
<212> TYPE: DNA
<213> ORGANISM: Artificial Sequence
<220> FEATURE:
<223> OTHER INFORMATION: Synthetic primer

<400> SEQUENCE: 51
cgtggtgatg gtgatgatgg tagtaaatac ctaaaaag    38

<210> SEQ ID NO 52
<211> LENGTH: 37
<212> TYPE: DNA
<213> ORGANISM: Artificial Sequence
<220> FEATURE:
<223> OTHER INFORMATION: Synthetic primer

<400> SEQUENCE: 52
cgtggtgatg gtgatgatgt tcgttaccaa tggaaac    37

<210> SEQ ID NO 53
<211> LENGTH: 37
<212> TYPE: DNA
<213> ORGANISM: Artificial Sequence
<220> FEATURE:
<223> OTHER INFORMATION: Synthetic primer

<400> SEQUENCE: 53
cgtggtgatg gtgatgatgg ttgttgatca cagcaat    37

<210> SEQ ID NO 54
<211> LENGTH: 38
<212> TYPE: DNA
<213> ORGANISM: Artificial Sequence
<220> FEATURE:
<223> OTHER INFORMATION: Synthetic primer

<400> SEQUENCE: 54
cgtggtgatg gtgatgatgg aaggcagtga ataagaag    38

<210> SEQ ID NO 55
<211> LENGTH: 54
<212> TYPE: DNA

<213> ORGANISM: Artificial Sequence
<220> FEATURE:
<223> OTHER INFORMATION: Synthetic primer

<400> SEQUENCE: 55

| catcatcacc atcaccacgg tgacgatgac gataagcatg gtgaaggtac tttc | 54 |

<210> SEQ ID NO 56
<211> LENGTH: 54
<212> TYPE: DNA
<213> ORGANISM: Artificial Sequence
<220> FEATURE:
<223> OTHER INFORMATION: Synthetic primer

<400> SEQUENCE: 56

| catcatcacc atcaccacgg tgacgatgac gataagttcc caaccattcc ctta | 54 |

<210> SEQ ID NO 57
<211> LENGTH: 39
<212> TYPE: DNA
<213> ORGANISM: Artificial Sequence
<220> FEATURE:
<223> OTHER INFORMATION: Synthetic primer

<400> SEQUENCE: 57

| cactccgttc aagtcgactt agaagccaca gctgccctc | 39 |

<210> SEQ ID NO 58
<211> LENGTH: 1059
<212> TYPE: DNA
<213> ORGANISM: Artificial Sequence
<220> FEATURE:
<223> OTHER INFORMATION: Synthetic YG2T92-IL2

<400> SEQUENCE: 58

| atggtgttcg gtcagctgta tgcccttttc atcttcacgt tatcatgttg tatttccaaa | 60 |
| actgtgcaag cagattcatc caaggaaagc tcttcctta tttcgttcga caaagagagt | 120 |
| aactgggata ccatcagcac tatatcttca acggcagatg ttatatcatc cgttgacagt | 180 |
| gctatcgctg tttttgaatt tgacaatttc tcattattgg acaacttgat gattgacgaa | 240 |
| gaatacccat tcttcaatag attctttgcc aatgatgtca gtttaactgt tcatgacgat | 300 |
| tcgcctttga acatctctca atcattatct cccattatgg aacaatttac tgtggatgaa | 360 |
| ttacctgaaa gtgcctctga cttactatat gaatactcct tagatgataa aagcatcgtt | 420 |
| ttgttcaagt ttacctcgga tgcctacgat ttgaaaaaat tagatgaatt tattgattct | 480 |
| tgcttatcgt ttttggaaga taaatctggc gacaatttga ctgtggttat taactctctt | 540 |
| ggttgggctt ttgaagatga agatggtgac gatgaatatg caacagaaga gactttgagc | 600 |
| catcatgata caacaagggg taagaaggc gacgatgatc tcgccttaga taaaagagca | 660 |
| cctacttcaa gttctacaaa gaaaacacag ctacaactgg agcatttact gctggattta | 720 |
| cagatgattt tgaatggaat taataattac aagaatccca aactcaccag gatgctcaca | 780 |
| tttaagtttt acatgcccaa gaaggccaca gaactgaaac atcttcagtg tctagaagaa | 840 |
| gaactcaaac ctctggagga agtgctaaat ttagctcaaa gcaaaaactt tcacttaaga | 900 |
| cccagggact taatcagcaa tatcaacgta atagttctgg aactaagggg atctgaaaca | 960 |
| acattcatgt gtgaatatgc tgatgagaca gcaaccattg tagaatttct gaacagatgg | 1020 |
| attacctttt gtcaaagcat catctcaaca ctaacttaa | 1059 |

-continued

```
<210> SEQ ID NO 59
<211> LENGTH: 756
<212> TYPE: DNA
<213> ORGANISM: Artificial Sequence
<220> FEATURE:
<223> OTHER INFORMATION: Synthetic YGaT923-EXD4

<400> SEQUENCE: 59
atggtgttcg gtcagctgta tgcccttttc atcttcacgt tatcatgttg tatttccaaa      60
actgtgcaag cagattcatc caaggaaagc tcttcctttta tttcgttcga caaagagagt    120
aactgggata ccatcagcac tatatcttca acggcagatg ttatatcatc cgttgacagt    180
gctatcgctg tttttgaatt tgacaatttc tcattattgg acagcttgat gattgacgaa    240
gaatacccat tcttcaatag attctttgcc aatgatgtca gtttaactgt tcatgacgat    300
tcgcctttgc aaatctctca atcattatct cccattatgg aacaatttac tgtggatgaa    360
ttacctgaaa gtgcctctga cttactatat gaatactcct tagatggtaa aagcatcgtt    420
ttgttcaagt ttacctcgga tgcctacgat ttgaaaaaat tagatgaatt tattgattct    480
tgcttatcgt ttttggaagg taaatctggc gacaatttga ctgtggttat taactctctt    540
ggttgggctt ttgaagatga agatggtgac gatgaatatg caacagaaga gactttgagc    600
catcatcacc atcaccacgg tgacgatgac gataagcatg gtgaaggtac ttttcacctct   660 gatttgtcta gcaaatggaa gaagaagct gttagattgt tcttggaatg gttgaagaac    720
ggtggtccat cctccggtgc tccaccacca tcttaa                              756

<210> SEQ ID NO 60
<211> LENGTH: 408
<212> TYPE: DNA
<213> ORGANISM: Artificial Sequence
<220> FEATURE:
<223> OTHER INFORMATION: Synthetic SCW4-1-EXD4

<400> SEQUENCE: 60
atgcgtctct ctaacctaat tgcttctgcc tctcttttat ctgctgctac tcttgctgct      60
cccgctaacc acgaacacaa ggacaagcgt gctgtggtca ctaccactgt tcaaaaacaa    120
accactatca ttgttaatgg tgccgcttca actccagttg ctgctttgga agaaaatgct    180
gttgtcaact ccgctccagc tgccgctacc agtacaacat cgtctgctgc ttctgtagct    240
accgctgctg ctcatcatca ccatcaccac ggtgacgatg acgataagca tggtgaaggt    300 actttcaccct ctgatttgtc taagcaaatg gaagaagaag ctgttagatt gttcttggaa    360
tggttgaaga acggtggtcc atcctccggt gctccaccac catcttaa                 408

<210> SEQ ID NO 61
<211> LENGTH: 561
<212> TYPE: DNA
<213> ORGANISM: Artificial Sequence
<220> FEATURE:
<223> OTHER INFORMATION: Synthetic SCW4-3-EXD4

<400> SEQUENCE: 61
atgcgtctct ctaacctaat tgcttctgcc tctcttttat ctgctgctac tcttgctgct      60
cccgctaacc acgaacacaa ggacaagcgt gctgtggtca ctaccactgt tcaaaaacaa    120
accactatca ttgttaatgg tgccgcttca actccagttg ctgctttgga agaaaatgct    180
gttgtcaact ccgctccagc tgccgctacc agtacaacat cgtctgctgc ttctgtagct    240
accgctgctg cttcctcttc tgagaacaac tcacaagttt ctgctgccgc atctccagcc    300
```

| | |
|---|---:|
| tccagctctg ctgctacatc tactcaatct tcctcttcct cccaagcttc ttcctctagt | 360 |
| tcttccggcg aagacgtcag cagctttgcc tctggtgtca gaggtcatca tcaccatcac | 420 |
| cacggtgacg atgacgataa gcatggtgaa ggtactttca cctctgattt gtctaagcaa | 480 |
| atggaagaag aagctgttag attgttcttg gaatggttga agaacggtgg tccatcctcc | 540 |
| ggtgctccac caccatctta a | 561 |

<210> SEQ ID NO 62
<211> LENGTH: 942
<212> TYPE: DNA
<213> ORGANISM: Saccharomyces sp.

<400> SEQUENCE: 62

| | |
|---|---:|
| atgcgtttct ctactacact cgctactgca gctactgcgc tattttcac agcctcccaa | 60 |
| gtttcagcta ttggtgaact agcctttaac ttgggtgtca gaacaacga tggtacttgt | 120 |
| aagtccactt ccgactatga aaccgaatta caagctttga gagctacac ttccaccgtc | 180 |
| aaagtttacg ctgcctcaga ttgtaacact ttgcaaaact taggtcctgc tgctgaagct | 240 |
| gagggattta ctatctttgt cggtgtttgg ccaacagacg acagtcatta cgctgctgaa | 300 |
| aaggctgctt tgcaaaccta tttgccaaaa attaaagaat ccactgttgc tggtttcttg | 360 |
| gttggttctg aagccttata ccgtaacgat tgactgcct ctcaattatc agacaaaatt | 420 |
| aatgacgtcc gtagtgtcgt tgctgacatt tccgattctg acgaaaagtc atactctggt | 480 |
| aagcaagtcg gtactgtcga ttcctggaat gttttggttg ctggttacaa ttctgccgtt | 540 |
| atcgaagctt ccgattttgt tatggctaac gcgttctcct actggcaagg tcaaaccatg | 600 |
| caaaatgcct cttactcatt ctttgatgat attatgcaag ctctacaggt tatccaatct | 660 |
| actaaaggtt ctaccgatat taccttctgg gttggtgaga ccggttggcc aactgatggt | 720 |
| accaactttg aaagttctta cccatctgtt gacaacgcca acaattctg gaagaaggt | 780 |
| atctgttcca tgagagcttg gggtgttaac gttattgttt ttgaagcctt tgatgaagat | 840 |
| tggaagccaa acacctctgg tacctctgat gtcgagaagc actgggtgt tttcacttca | 900 |
| agtgacaatt tgaaatactc cttggactgt gacttttcat ga | 942 |

<210> SEQ ID NO 63
<211> LENGTH: 1575
<212> TYPE: DNA
<213> ORGANISM: Saccharomyces sp.

<400> SEQUENCE: 63

| | |
|---|---:|
| atgcaactat ctaaaagtat actactggca gcattagctg ctacaccatc tctggtgaat | 60 |
| gccatgctcc ccatccatat caagaattat aggttcatta agccatcctc tgccacaaat | 120 |
| agcgaatccg ataacgaagt tttttttgtg aaaggtgtcg attatcagcc tggtgggtcg | 180 |
| tctggttacg atgctgactc tgatacagat attctttctg accctgaagt gtgtgccaga | 240 |
| gacgcctacg ctttccaaca acttggtgtc aacacagtga gaatttactc cctgaaccct | 300 |
| gacctaaatc atgacaagtg catgactatc ttcaacaatg ctggtatcta cgccattttg | 360 |
| gatgttaata gtggtaatta cggggagagt ttgaaccgtg ctgacccatc tggaacatat | 420 |
| gactctttgt atttgtcaag agtcttcaaa tttattgacg ctttcaagaa ctaccctaac | 480 |
| gtgctaggat tcttttctgg caacgaagtc ataaatgatc aaagcgacta tgcaaaaatt | 540 |
| gatcctccat acatccgcgc tgttcaaaga gatatgaaac agtatatttc aaaacatgcg | 600 |
| aacagaagca tcccagtcgg atattctgct gctgacaata ctgatttgag gttagcaacc | 660 |

```
ttcaagtact tgcagtgtaa ttcgttggat ggaaacaaag tcaatgatga tttggacata      720
tctaaatctg atttctttgg cctaaatact tatgaatggt gctctggcac ttctagttgg      780
gaatcttctg gctatgacaa gttaaactca actttcgaag atgctgttat tccgttgata      840
ttttctgagt atggttgcaa caaaatacaa ccaagaactt tgacgaagt  ctctgagggt      900 ttgtatggtg gtttaaagaa cgtcttctct ggtgggttgg tatacgaata cactgaagaa      960
gctaataatt acgtttggt  taagcttgat gatagcggtt ctttaactta taaggatgat     1020
tttgttaatt tagaatcaca attgaagaac gtttcattgc caacaacaaa agaaagcgaa     1080
atatcttctg actctatcta caagtgcgat aacagtgcca tcaccaatat ttattctggc     1140
tttggaacga acaatttcac tttgccttct caaccagcag aaattgccaa tatgattgaa     1200
tacggtgtta atggcaccaa caccggtaag atattgactg attatgctgt tccaactact     1260
tttaactata caattaaaaa caataaagat gataccattt cagctactat ttcatacgac     1320
aaagctaact cactgaacga actagacgtc acagccacaa cggtcgcaaa gtcagcttcc     1380
acatcacaat catcttctcg ctccttaact tcaagcacca gtccatcttc aagcactggc     1440
tcatcttcaa gcaccggttc atcttcagct tcaagcagcc ccaaaagtaa aggcgtcgga     1500
aatattgtta atgtttcctt tagtcagtct ggataccttg cattatttgc aggtctgatt     1560
tctgctctac tctga                                                     1575

<210> SEQ ID NO 64
<211> LENGTH: 1455
<212> TYPE: DNA
<213> ORGANISM: Saccharomyces sp.

<400> SEQUENCE: 64
atgttactac gttctcttac aagtgccttc gttttaagtg ctggtttggc tcaggctgct       60
agcagcagta acagttccac accatccatt gaaattaaag gcaatgcatt ttttaattcg      120
gaatcaggtg aaaggtttta tatccgtggt gttgattacc agcctggtgg ttcttctaac      180
ttgactgatc ccttagcaga cgcatctgtc tgtgacagag acgtccccgt tctgaaagat      240
ctagggataa atactgtcag agtttatact gtggataact cgcaagatca ttcccattgt      300
atgaaactat tgcaggagaa cggtatatac ttgatcctgg atgtcaatac ccccacgagt      360
gctatttctc gttacgatcc agcctgctcc tataacgctg actacttaca aaatgtcttt      420
gccaccattg ataccttgc  tgattacgac aatgttctag gttttttcgc tggtaacgag      480
gtcatcaata gtgttaatac taccaacact gctacttatg tcaaggcagt ggtcagggac      540
atgaagaaat acatcaaggc tagaaaatac agacaaattc cggtaggtta ctcggctgct      600
gatatcgtcg ctaacagaca attggctgct gaatacttta ctgtggtga  tgaagctgac      660 gctagaatcg acatgtttgg tgttaatgac tattcttggt gtggtgaatc ttcatttgtg      720
gtatcgggtt attccaccaa gatgaagcta tatcaagatt actccgttcc tgtcttctta      780
agtgaatttg gttgtaacca agtcaagagc tctcgtccat tcacagaaat tgaagctatc      840
tattccactc aaatgtcttc tgtattctcc ggtgggctag tctacgaata ttccaatgaa      900
actaacaatt acgggctcgt tcaaattgat ggtgacaagg tcactaaatt gacagatttt      960
gaaaacttga aaaatgaata cagcaaagta tccaacccag aaggcaatgg tggttacagt     1020
acttccaaca actattctac atgtcctgat tatgaaaagg gtgtctggga agctaataac     1080
actttgcctg ctatgccaag tgctgcttct gcttacttca catctggagc aggttctcct     1140
```

| | |
|---|---|
| atgggaaccg gaatcgccac ccaacaaagt tgtgatgcta aggacgatga cgacgaagaa | 1200 |
| gacgacgaca cctcctcttc atcctcttct tcctcttcat cttcatcttc cgcttcttca | 1260 |
| tcttctgaat catcatcctc gacttcaaag gcatcttcct cctcccttc tgctagcgaa | 1320 |
| acgagcttgc taaaatctgc cgcatctgct acttcgtcca gccaatcgtc tcgaaatca | 1380 |
| aagggtgctg ccggaattat tgagattcct ttgatattcc gtgctttggc agaactttat | 1440 |
| aacttggttt tatga | 1455 |

<210> SEQ ID NO 65
<211> LENGTH: 1335
<212> TYPE: DNA
<213> ORGANISM: Saccharomyces sp.

<400> SEQUENCE: 65

| | |
|---|---|
| atgcaattac attcacttat cgcttcaact gcgctcttaa taacgtcagc tttggctgct | 60 |
| acttcctctt cttccagcat accctcttcc tgtaccataa gctcacatgc cacggccaca | 120 |
| gctcagagtg acttagataa atatagccgc tgtgatacgt tagtcgggaa cttaactatt | 180 |
| ggtggtggtt tgaagactgg tgctttggct aatgttaaag aaatcaacgg gtctctaact | 240 |
| atatttaacg ctacaaatct aacctcattc gctgctgatt ccttggagtc catcacagat | 300 |
| tcttttgaacc tacagagttt gacaatcttg acttctgctt catttgggtc tttacagagc | 360 |
| gttgatagta taaaactgat tactctaccc gccatctcca gttttacttc aaatatcaaa | 420 |
| tctgctaaca acatttatat ttccgacact tcgttacaat ctgtcgatgg attctcagcc | 480 |
| ttgaaaaaag ttaacgtgtt caacgtcaat aacaataaga aattaacctc gatcaaatct | 540 |
| ccagttgaaa cagtcagcga ttcttttacaa ttttcgttca acggtaacca gactaaaatc | 600 |
| accttcgatg acttggtttg ggcaaacaat atcagtttga ccgatgtcca ctctgtttcc | 660 |
| ttcgctaact tgcaaaagat taactcttca ttgggtttca tcaacaactc catctcaagt | 720 |
| ttgaatttca ctaagctaaa caccattggc caaaccttca gtatcgtttc caatgactac | 780 |
| ttgaagaact tgtcgttctc taatttgtca accataggtg gtgctcttgt cgttgctaac | 840 |
| aacactggtt tacaaaaaat tggtggtctc gacaacctaa caaccattgg cggtactttg | 900 |
| gaagttgttg gtaacttcac ctcccttgaac ctagactctt tgaagtctgt caagggtggc | 960 |
| gcagatgtcg aatcaaagtc aagcaatttc tcctgtaatg cttttgaaagc tttgcaaaag | 1020 |
| aaaggggggta tcaagggtga atcttttgtc tgcaaaaatg gtgcatcatc cacatctgtt | 1080 |
| aaactatcgt ccacttccaa atctcaatca agccaaacta ctgccaaggt ttccaagtca | 1140 |
| tcttctaagg ccgaggaaaa gaagttcact tctggcgata tcaaggctgc tgcttctgcc | 1200 |
| tctagtgttt ctagttctgg cgcttccagc tctagctcta agagttccaa aggcaatgcc | 1260 |
| gctatcatgg caccaattgg ccaaacaacc cctttggtcg gtcttttgac ggcaatcatc | 1320 |
| atgtctataa tgtaa | 1335 |

<210> SEQ ID NO 66
<211> LENGTH: 1161
<212> TYPE: DNA
<213> ORGANISM: Saccharomyces sp.

<400> SEQUENCE: 66

| | |
|---|---|
| atgcgtctct ctaacctaat tgcttctgcc tctcttttat ctgctgctac tcttgctgct | 60 |
| cccgctaacc acgaacacaa ggacaagcgt gctgtggtca ctaccactgt tcaaaaacaa | 120 |
| accactatca ttgttaatgg tgccgcttca actccagttg ctgctttgga agaaaatgct | 180 |

-continued

```
gttgtcaact ccgctccagc tgccgctacc agtacaacat cgtctgctgc ttctgtagct      240
accgctgctg cttcctcttc tgagaacaac tcacaagttt ctgctgccgc atctccagcc      300 tccagtctg ctgctacatc tactcaatct tcctcttcct cccaagcttc ttcctctagt      360
tcttccggcg aagacgtcag cagctttgcc tctggtgtca gaggtatcac ttataccccca    420 tacgagtcca gcggtgcttg taaatccgct tcggaagttg cttccgattt agctcaattg     480
actgacttcc cagtcattag attgtacggt accgactgta accaagttga aaatgttttc     540
aaggctaagg cttcgaacca aaaagtcttt ttaggtattt actacgttga ccaaatccaa     600
gacggtgtca acaccatcaa gtctgctgtt gaatcttacg gttcttggga cgatgtcacc     660
actgtttcca ttggtaacga attggttaac ggtaaccaag ctaccccatc ccaagtcggt    720
caatacattg actctggtag atctgccttg aaggctgccg gttacactgg tccagttgtt    780
tctgttgata cttttattgc tgtgatcaac aaccctgaat tgtgtgacta ctccgactac    840
atggctgtta atgcccatgc ttactttgac aagaacacag ttgcccaaga ctccggtaaa    900
tggttactag aacaaatcca agagtctggg actgcttgtg atggtaagaa gaatgttgtt    960
atcactgagt ctggttggcc atcaaagggt gagacttacg tgttgctgt tccatctaag    1020 gaaaatcaaa aggacgctgt tccgccatt accagctcct gtggtgctga taccttctta    1080
ttcactgcct tcaacgacta ctggaaggcc gacggtgctt acggtgttga aaaatactgg   1140
ggtattctat ccaatgaata a                                              1161
```

<210> SEQ ID NO 67
<211> LENGTH: 1170
<212> TYPE: DNA
<213> ORGANISM: Saccharomyces sp.

<400> SEQUENCE: 67

```
atgcgttttt caaatttcct aactgtatct gcattattaa ccggagctct aggagctcct      60
gctgttcgcc ataaacatga aaagcgtgac gttgttactg ccacagtcca tgcgcaggtt     120
actgttgtcg tttccggtaa cagcggcgaa actattgttc cagtgaacga gaatgctgtt    180
gtagctacta ccagcagtac tgcagttgct ctcaagcaa ctacatccac tttagaacca     240
acaacttccg ctaatgtcgt cacttctcaa caacaaacca gcactcttca atcttccgag    300
gcagcatcta cggttggttc ttcgacttca tcctcaccct catcctcatc ctcaacttca   360
tcttcagctt catcctccgc ttcatctagt atctcagcct ccggtgctaa gggtattact    420
tacagtcctt acaatgatga tgggtcctgt aaatctactg ctcaagtcgc ctcagattta   480
gaacagttga ctggttttga acacatcaga ttatatggcg ttgactgtag tcaggttgag   540
aatgtcttgc aagctaaaac ttcaagccag aaattattct taggcatata ttacgttgac   600
aaaattcaag acgccgttga actattaaa tctgcagttg agtcttatgg ctcctgggat    660
gatattacca ctgtttctgt cggtaacgaa ctggtcaatg cgggttctgc cactacgacg   720
caagtcggtg aatacgtttc cacggccaag tcagctttaa cctctgctgg ttatacaggc   780
tcagtcgttt ccgttgatac cttcattgct gttataaata accctgacct gtgtaattat   840
tctgactata tggctgtcaa cgcccatgca tacttcgatg aaaatactgc ggcccaagat   900
gcaggaccat gggtactaga acaaatcgaa agggtttaca ctgcttgtgg tgggaaaaag   960
gacgtcgtta ttaccgaaac tggttggcca tctaagggtg atacttacgg cgaagctgtc  1020
ccatctaaag caaaccaaga agccgccatt tcttctatca aaagctcctg cggctcttca   1080
```

```
gcttacttat ttaccgcctt caatgatcta tggaaagatg atgggcaata cggtgttgaa    1140
aaatactggg gtattctatc aagtgattaa                                     1170

<210> SEQ ID NO 68
<211> LENGTH: 1428
<212> TYPE: DNA
<213> ORGANISM: Saccharomyces sp.

<400> SEQUENCE: 68
atgaaattct caactgccgt tactacgttg attagttctg gtgccatcgt gtctgcttta     60
ccacacgtgg atgttcacca agaagatgcc caccaacata gagggccgt tgcgtacaaa    120 tacgtttacg aaactgttgt tgtcgattct gatggccaca ctgtaactcc tgctgcttca    180
gaagtcgcta ctgctgctac ctctgctatc attacaacat ctgtgttggc tccaacctcc    240
tccgcagccg ctgggatagc cgcttccatt gctgtttcat ctgctgcctt agccaagaat    300
gagaaaatct ctgatgccgc tgcatctgcc actgcctcaa catctcaagg gcatcctcc    360 tcctcctcct cctcctcggc aacttctacc ctagaaagca gctctgtttc ttcatctagt    420
gaagaagctg ctccaacatc tactgtcgtg tcaacttctt ccgcaaccca atctagtgct    480
tcttctgcca ctaaatctag tacttcttcc acttcaccat ctacttctac ttctacttcc    540
acttcttcta cttcctcttc ctcttcctcc tcctcctcct cttcttcttc ttcttctggc    600
agtggtagta tctacggtga tttggccgac ttttcaggcc caagtgagaa attccaagac    660
ggcactattc catgtgacaa attcccatct ggtcaaggtg tcatttctat tgactggatt    720
ggcgagggtg gatggtccgg tgtggaaaac accgacactt ccactggcgg ttcatgcaag    780
gaggggtcct actgttccta ctcctgccaa ccaggtatgt ctaagaccca atggccatcc    840
gatcaaccat ctgacggtag atctgtcggg ggtttgttgt gtaaaaatgg ttatttgtac    900
cgttctaaca ctgacgcgga ttacttatgt gaatggggtg tcgaggctgc ctatgttgtt    960
tctaaactaa gcaagggtgt cgccatttgc agaaccgact accgggcac tgaaaacatg    1020 gttatcccaa cctatgttga aggggtagc tctttgccat tgaccgttgt tgaccaagat    1080
acttacttta cttgggaagg caaaaagaca tctgctcaat actacgttaa taacgccggc    1140
gtctcagttg aagatgggtg tatctggggt acttctggat ctggtattgg taactgggca    1200
ccattaaact tggtgctgg ctccactggt ggagtgacat acttatcatt gattcctaac    1260
ccaaacaaca gcgacgcatt gaactacaac gtcaagatag ttgctgctga tgattcatcc    1320
aatgtcatcg gtaatgtgt ttacgaaaat ggtgagttct ctggcggtgc tgacgggtgt    1380
accgtctctg ttacttccgg taaagctcat ttcgtcttat acaattaa              1428

<210> SEQ ID NO 69
<211> LENGTH: 1098
<212> TYPE: DNA
<213> ORGANISM: Saccharomyces sp.

<400> SEQUENCE: 69
atgaaattat ccgctctatt agctttatca gcctccaccg ccgtcttggc cgctccagct     60
gtccaccata gtgacaacca ccaccacaac gacaagcgtg ccgttgtcac cgttactcag    120
tacgtcaacg cagacggcgc tgttgttatt ccagctgcca ccaccgctac ctcggcggct    180
gctgatggaa aggtcgagtc tgttgctgct gccaccacta ctttgtcctc gactccgcc    240 gccgctacta cctctgccgc cgcctcttct tcctcctctt cctcttcctc ctcttcctct    300
tcttcctctg ttggttctgg agattttgaa gatggtacca tttcctgttc tgatttccca    360
```

```
tccggacaag gtgctgtctc cttggactgg ttaggtctag gcggctgggc ttccatcatg    420
gacatgaacg gtaacaccgc cacctcttgt caagacggat actactgttc ttacgcttgt    480
tctccaggtt acgctaagac ccaatggcct tctgaacaac cttccgatgg tagatccgtt    540
ggtggtttat actgtaagaa cggtaaatta taccgttcca acaccgacac taacagtttg    600
tgtgtagaag gtcaaggctc tgctcaagct gttaacaagg tctccggctc cattgctatc    660
tgtggtaccg attatccagg ttctgaaaac atggtcgttc ctaccgtagt tggcgctggt    720
tcctcccaac caatcaacgt catcaaggag gactcctact atcaatggca aggtaagaag    780
acctctgccc aatactacgt taacaacgct ggtgtctctg tggaagatgg ttgtatctgg    840
ggtactgagg gttccggtgt cggtaactgg gccccagttg tcttgggtgc tggttacact    900
gatggtatca cttacttgtc catcattcca aacccaaaca caaagaagc accaaacttt    960 aacatcaaga tcgttgccac cgatggctct accgtcaatg gtgcttgctc ttacgaaaat   1020
ggtgtctact ctggctctgg ctctgacggt tgtactgttt cagttacttc tggttctgct   1080
aactttgtct tctactag                                                 1098
```

<210> SEQ ID NO 70
<211> LENGTH: 1065
<212> TYPE: DNA
<213> ORGANISM: Saccharomyces sp.

<400> SEQUENCE: 70

```
atgaagttcc aagttgtttt atctgcccctt ttggcatgtt catctgccgt cgtcgcaagc     60
ccaatcgaaa acctattcaa atacagggct gttaaggcat ctcacagtaa gaatatcaac    120
tccactttgc cggcctggaa tgggtctaac tctagcaatg ttacctacgc taatggaaca    180
aacagtacta ccaatactac tactgccgaa agcagtcaat tacaaatcat tgtaacaggt    240
ggtcaagtac caatcaccaa cagttctttg acccacacaa actacaccag attattcaac    300
agttcttctg ctttgaacat taccgaattg tacaatgttg cccgtgttgt taacgaaacg    360
atccaagata gtcatccgc cggtgccgtt gttgttgcca acgccaaatc tttggaagct    420
gtctcattct tcttctctat cattttttgac accgaaaagc ctattgttgt cactgaagat    480
tccgcttatg ccattccagt cgctaacaat aagaacgcta ccaaacgtgg tgtcttgtcc    540
gtcacttctg acaaattagt gtactccggt gtcttcactc cacctactgc ttgttcttac    600
ggtgctggtt tgcctgttgc tatcgttgat gaccaagacg aagttaaatg gttcttcgat    660
gcttctaagc caactttaat ctcttctgac tcgattatca gaaaggaata cagtaacttc    720
actactcctt atggtctatt agaaaacggt gttccaattg ttccaattgt ctatgacggt    780
ggttactctt ccagtttgat tgactccttg agttctgccg ttcaaggttt ggttgttgtt    840
tcttctggtt ctaccaactc aacctcatct actattgaaa gcactgaaat cccagtcgta    900
tatgctcaag ctaacactcc attaaacttt attgacaaca aagatgttcc aaagaacgct    960
gtgggtgctg gttacctatc cccaattaag gcccaaatct tgttgtccat tgctgccgtt   1020
aatggtgtca cctccaagtc cgctctggaa agcatttttcc catga                  1065
```

<210> SEQ ID NO 71
<211> LENGTH: 1710
<212> TYPE: DNA
<213> ORGANISM: Saccharomyces sp.

<400> SEQUENCE: 71

-continued

```
atgaaactga aaactgtaag atctgcggtc ctttcgtcac tctttgcatc gcaggttctc    60
ggtaagataa taccagcagc aaacaagcgc gacgacgact cgaattccaa gttcgtcaag   120
ttgcccttc ataagcttta cggggactcg ctagaaaatg tgggaagcga caaaaaaccg   180
gaagtacgcc tattgaagag ggctgacggt tatgaagaaa ttataattac caaccagcaa   240
agtttctatt cggtggactt ggaagtgggc acgccaccac agaacgtaac ggtcctggtg   300
gacacaggct cctctgatct atggattatg ggctcggata atccatactg ttcttcgaac   360
agtatgggta gtagccggag acgtgttatt gacaaacgtg atgattcgtc aagcggcgga   420
tctttgatta atgatataaa cccatttggc tggttgacgg gaacgggcag tgccattggc   480
cccactgcta cgggcttagg aggcggttca ggtacggcaa ctcaatccgt gcctgcttcg   540
gaagccacca tggactgtca acaatacggg acattttcca cttcgggctc ttctacattt   600
agatcaaaca acacctattt cagtattagc tacggtgatg ggacttttgc ctccggtact   660
tttggtacgg atgttttgga tttaagcgac ttgaacgtta ccgggttgtc ttttgccgtt   720
gccaatgaaa cgaattctac tatgggtgtg ttaggtattg gtttgcccga attagaagtc   780
acttattctg gctctactgc gtctcatagt ggaaaagctt ataaatacga caacttcccc   840
attgtattga aaaattctgg tgctatcaaa agcaacacat attctttgta tttgaacgac   900
tcggacgcta tgcatggcac cattttgttc ggagccgtgg accacagtaa atataccggc   960
acctataca caatccccat cgtaaacact ctgagtgcta gtggatttag ctctcccatt  1020
caatttgatg tcactattaa tggtatcggt attagtgatt ctgggagtag taacaagacc  1080
ttgactacca ctaaaatacc tgctttgttg gattccggta ctactttgac ttatttacct  1140
caaacagtgg taagtatgat cgctactgaa ctaggtgcgc aatactcttc caggatagg  1200
tattacgtat tggactgtcc atctgatgat agtatggaaa tagtgttcga ttttggtggt  1260
tttcacatca atgcaccact ttcgagtttt atcttgagta ctggcactac atgtcttta   1320
ggtattatcc caacgagtga tgacacaggt accatttttgg gtgattcatt tttgactaac  1380
gcgtacgtgg tttatgattt ggagaatctt gaaatatcca tggcacaagc tcgctataat  1440
accacaagcg aaaatatcga aattattaca tcctctgttc caagcgccgt aaaggcacca  1500
ggctatacaa acacttggtc cacaagtgca tctattgtta ccggtggtaa catatttact  1560
gtaaattcct cacaaactgc ttcctttagc ggtaacctga cgaccagtac tgcatccgcc  1620
acttctacat caagtaaaag aaatgttggt gatcatatag ttccatcttt acccctcaca  1680
ttaatttctc ttctttttgc attcatctga                                   1710
```

<210> SEQ ID NO 72
<211> LENGTH: 750
<212> TYPE: DNA
<213> ORGANISM: Saccharomyces sp.

<400> SEQUENCE: 72

```
atgaagttct cttccggcaa atctatcatc tttgcaacta ttgcttctct agctttgagt    60
gctcctgtca cttacgacac caactctact gctgagttac aatctccttc atctcaagaa   120
attctgggtt ggagtcacgc aacttttcct accatttacc aaacctgtaa tgagacgaac   180
gcaagaatgt tgaatgcagc ttttaaggat accgctgaaa tcaccgctta tggtaaagat   240
agacttttga actatggtgt cgatgacgtt tactacaaaa gatggtttgg taatggtagt   300
attttcaccg tcatgggtgt ctttgagcaa ttgatggagg cttccaaggg tgccatgctc   360
atgagatgtg atgatattga tggcttgtgt gcagctaatc caaactatta cgctggtcat   420
```

```
caccgtcaat ctgctccagc tgaaactgtt atttgtgatt acttctacac ttccaaaaag    480
ccactatcaa caatttgttt cgaaggtact attgtcgatg tcggtccaaa acattatgca    540
ggtattgata tgttacatcg ttacttgcac gtccctacca tgagtatgga tggatatgtt    600
ggcgagtacg cggaaactct tgaagaagtt gtggactaca cccagaacaa tgctacttac    660
gcagttagaa acaccgacaa ctatctttac tatctcgctg acgtttacag tgcttctgtt    720
atacctggtg gctgtctagg taacttgtaa                                     750
```

<210> SEQ ID NO 73
<211> LENGTH: 915
<212> TYPE: DNA
<213> ORGANISM: Artificial Sequence
<220> FEATURE:
<223> OTHER INFORMATION: Synthetic SCW4-2-hGH

<400> SEQUENCE: 73

```
atgcgtctct ctaacctaat tgcttctgcc tctcttttat ctgctgctac tcttgctgct     60
cccgctaacc acgaacacaa ggacaagcgt gctgtggtca ctaccactgt tcaaaaacaa    120
accactatca ttgttaatgg tgccgcttca actccagttg ctgctttgga agaaaatgct    180
gttgtcaact ccgctccagc tgccgctacc agtacaacat cgtctgctgc ttctgtagct    240
accgctgctg cttcctcttc tgagaacaac tcacaagttt ctgctgccgc atctccagcc    300
tcccatcatc accatcacca cggtgacgat gacgataagt cccaaccat tcccttatcc    360 aggcttttg acaacgctat gctccgcgcc catcgtctgc accagctggc ctttgacacc    420
taccaggagt ttgaagaagc ctatatccca aggaacaga agtattcatt cctgcagaac    480
ccccagacct ccctctgttt ctcagagtct attccgacac cctccaacag ggaggaaaca    540
caacagaaat ccaacctaga gctgctccgc atctccctgc tgctcatcca gtcgtggctg    600
gagcccgtgc agttcctcag gagtgtcttc gccaacagcc tggtgtacgg cgcctctgac    660
agcaacgtct atgacctcct aaaggaccta gaggaaggca tccaaacgct gatggggagg    720
ctggaagatg gcagcccccg gactgggcag atcttcaagc agacctacag caagttcgac    780
acaaactcac acaacgatga cgcactactc aagaactacg gctgctcta ctgcttcagg    840 aaggacatgg acaaggtcga cattcctg cgcatcgtgc agtgccgctc tgtggagggc    900
agctgtggct ctaa                                                     915
```

<210> SEQ ID NO 74
<211> LENGTH: 4
<212> TYPE: PRT
<213> ORGANISM: Artificial Sequence
<220> FEATURE:
<223> OTHER INFORMATION: Synthetic yeast kex2-like protease recognition
      sequence

<400> SEQUENCE: 74

Leu Asp Lys Arg
1

<210> SEQ ID NO 75
<211> LENGTH: 4
<212> TYPE: PRT
<213> ORGANISM: Artificial Sequence
<220> FEATURE:
<223> OTHER INFORMATION: Synthetic factor Xa-recognition sequence

<400> SEQUENCE: 75

-continued

Ile Glu Gly Arg
1

<210> SEQ ID NO 76
<211> LENGTH: 4
<212> TYPE: PRT
<213> ORGANISM: Artificial Sequence
<220> FEATURE:
<223> OTHER INFORMATION: Synthetic subtilisin-recognition sequence

<400> SEQUENCE: 76

Ala Ala His Tyr
1

<210> SEQ ID NO 77
<211> LENGTH: 7
<212> TYPE: PRT
<213> ORGANISM: Artificial Sequence
<220> FEATURE:
<223> OTHER INFORMATION: Synthetic tobacco etch virus protease-
      recognition sequence

<400> SEQUENCE: 77

Glu Asn Leu Tyr Phe Gln Gly
1               5

<210> SEQ ID NO 78
<211> LENGTH: 4
<212> TYPE: PRT
<213> ORGANISM: Artificial Sequence
<220> FEATURE:
<223> OTHER INFORMATION: Synthetic thrombin-recognition sequence

<400> SEQUENCE: 78

Arg Gly Pro Arg
1

<210> SEQ ID NO 79
<211> LENGTH: 5
<212> TYPE: PRT
<213> ORGANISM: Artificial Sequence
<220> FEATURE:
<223> OTHER INFORMATION: Synthetic enterokinase cleavage sequence

<400> SEQUENCE: 79

Asp Asp Asp Asp Lys
1               5

<210> SEQ ID NO 80
<211> LENGTH: 313
<212> TYPE: PRT
<213> ORGANISM: Saccharomyces sp.

<400> SEQUENCE: 80

Met Arg Phe Ser Thr Thr Leu Ala Thr Ala Ala Thr Ala Leu Phe Phe
1               5                   10                  15

Thr Ala Ser Gln Val Ser Ala Ile Gly Glu Leu Ala Phe Asn Leu Gly
                20                  25                  30

Val Lys Asn Asn Asp Gly Thr Cys Lys Ser Thr Ser Asp Tyr Glu Thr
            35                  40                  45

Glu Leu Gln Ala Leu Lys Ser Tyr Thr Ser Val Lys Val Tyr Ala
        50                  55                  60

Ala Ser Asp Cys Asn Thr Leu Gln Asn Leu Gly Pro Ala Ala Glu Ala
65                  70                  75                  80

```
Glu Gly Phe Thr Ile Phe Val Gly Val Trp Pro Thr Asp Asp Ser His
             85                  90                  95
Tyr Ala Ala Glu Lys Ala Ala Leu Gln Thr Tyr Leu Pro Lys Ile Lys
            100                 105                 110
Glu Ser Thr Val Ala Gly Phe Leu Val Gly Ser Glu Ala Leu Tyr Arg
        115                 120                 125
Asn Asp Leu Thr Ala Ser Gln Leu Ser Asp Lys Ile Asn Asp Val Arg
    130                 135                 140
Ser Val Val Ala Asp Ile Ser Asp Ser Asp Gly Lys Ser Tyr Ser Gly
145                 150                 155                 160
Lys Gln Val Gly Thr Val Asp Ser Trp Asn Val Leu Val Ala Gly Tyr
                165                 170                 175
Asn Ser Ala Val Ile Glu Ala Ser Asp Phe Val Met Ala Asn Ala Phe
            180                 185                 190
Ser Tyr Trp Gln Gly Gln Thr Met Gln Asn Ala Ser Tyr Ser Phe Phe
        195                 200                 205
Asp Asp Ile Met Gln Ala Leu Gln Val Ile Gln Ser Thr Lys Gly Ser
    210                 215                 220
Thr Asp Ile Thr Phe Trp Val Gly Glu Thr Gly Trp Pro Thr Asp Gly
225                 230                 235                 240
Thr Asn Phe Glu Ser Ser Tyr Pro Ser Val Asp Asn Ala Lys Gln Phe
                245                 250                 255
Trp Lys Glu Gly Ile Cys Ser Met Arg Ala Trp Gly Val Asn Val Ile
            260                 265                 270
Val Phe Glu Ala Phe Asp Glu Asp Trp Lys Pro Asn Thr Ser Gly Thr
        275                 280                 285
Ser Asp Val Glu Lys His Trp Gly Val Phe Thr Ser Ser Asp Asn Leu
    290                 295                 300
Lys Tyr Ser Leu Asp Cys Asp Phe Ser
305                 310

<210> SEQ ID NO 81
<211> LENGTH: 524
<212> TYPE: PRT
<213> ORGANISM: Saccharomyces sp.

<400> SEQUENCE: 81

Met Gln Leu Ser Lys Ser Ile Leu Leu Ala Leu Ala Ala Thr Pro
1               5                  10                  15
Ser Leu Val Asn Ala Met Leu Pro Ile His Ile Lys Asn Tyr Arg Phe
            20                  25                  30
Ile Lys Pro Ser Ser Ala Thr Asn Ser Glu Ser Asp Asn Glu Val Phe
        35                  40                  45
Phe Val Lys Gly Val Asp Tyr Gln Pro Gly Gly Ser Ser Gly Tyr Asp
    50                  55                  60
Ala Asp Ser Asp Thr Asp Ile Leu Ser Asp Pro Glu Val Cys Ala Arg
65                  70                  75                  80
Asp Ala Tyr Ala Phe Gln Gln Leu Gly Val Asn Thr Val Arg Ile Tyr
                85                  90                  95
Ser Leu Asn Pro Asp Leu Asn His Asp Lys Cys Met Thr Ile Phe Asn
            100                 105                 110
Asn Ala Gly Ile Tyr Ala Ile Leu Asp Val Asn Ser Gly Asn Tyr Gly
        115                 120                 125
Glu Ser Leu Asn Arg Ala Asp Pro Ser Gly Thr Tyr Asp Ser Leu Tyr
    130                 135                 140
```

```
Leu Ser Arg Val Phe Lys Phe Ile Asp Ala Phe Lys Asn Tyr Pro Asn
145                 150                 155                 160

Val Leu Gly Phe Phe Ser Gly Asn Glu Val Ile Asn Asp Gln Ser Asp
            165                 170                 175

Tyr Ala Lys Ile Asp Pro Pro Tyr Ile Arg Ala Val Gln Arg Asp Met
        180                 185                 190

Lys Gln Tyr Ile Ser Lys His Ala Asn Arg Ser Ile Pro Val Gly Tyr
    195                 200                 205

Ser Ala Ala Asp Asn Thr Asp Leu Arg Leu Ala Thr Phe Lys Tyr Leu
210                 215                 220

Gln Cys Asn Ser Leu Asp Gly Asn Lys Val Asn Asp Asp Leu Asp Ile
225                 230                 235                 240

Ser Lys Ser Asp Phe Phe Gly Leu Asn Thr Tyr Glu Trp Cys Ser Gly
            245                 250                 255

Thr Ser Ser Trp Glu Ser Ser Gly Tyr Asp Lys Leu Asn Ser Thr Phe
            260                 265                 270

Glu Asp Ala Val Ile Pro Leu Ile Phe Ser Glu Tyr Gly Cys Asn Lys
        275                 280                 285

Asn Thr Pro Arg Thr Phe Asp Glu Val Ser Glu Gly Leu Tyr Gly Gly
        290                 295                 300

Leu Lys Asn Val Phe Ser Gly Gly Leu Val Tyr Glu Tyr Thr Glu Glu
305                 310                 315                 320

Ala Asn Asn Tyr Gly Leu Val Lys Leu Asp Asp Ser Gly Ser Leu Thr
            325                 330                 335

Tyr Lys Asp Asp Phe Val Asn Leu Glu Ser Gln Leu Lys Asn Val Ser
            340                 345                 350

Leu Pro Thr Thr Lys Glu Ser Glu Ile Ser Ser Asp Ser Ile Tyr Lys
        355                 360                 365

Cys Asp Asn Ser Ala Ile Thr Asn Ile Tyr Ser Gly Phe Gly Thr Asn
370                 375                 380

Asn Phe Thr Leu Pro Ser Gln Pro Ala Glu Ile Ala Asn Met Ile Glu
385                 390                 395                 400

Tyr Gly Val Asn Gly Thr Asn Thr Gly Lys Ile Leu Thr Asp Tyr Ala
            405                 410                 415

Val Pro Thr Thr Phe Asn Tyr Thr Ile Lys Asn Asn Lys Asp Asp Thr
            420                 425                 430

Ile Ser Ala Thr Ile Ser Tyr Asp Lys Ala Asn Ser Leu Asn Glu Leu
        435                 440                 445

Asp Val Thr Ala Thr Val Ala Lys Ser Ala Ser Thr Ser Gln Ser
    450                 455                 460

Ser Ser Arg Ser Leu Thr Ser Ser Thr Ser Pro Ser Ser Ser Thr Gly
465                 470                 475                 480

Ser Ser Ser Ser Thr Gly Ser Ser Ser Ala Ser Ser Ser Ser Lys Ser
            485                 490                 495

Lys Gly Val Gly Asn Ile Val Asn Val Ser Phe Ser Gln Ser Gly Tyr
            500                 505                 510

Leu Ala Leu Phe Ala Gly Leu Ile Ser Ala Leu Leu
            515                 520

<210> SEQ ID NO 82
<211> LENGTH: 484
<212> TYPE: PRT
<213> ORGANISM: Saccharomyces sp.
```

<400> SEQUENCE: 82

```
Met Leu Leu Arg Ser Leu Thr Ser Ala Phe Val Leu Ser Ala Gly Leu
1               5                   10                  15
Ala Gln Ala Ala Ser Ser Asn Ser Ser Thr Pro Ser Ile Glu Ile
            20                  25                  30
Lys Gly Asn Ala Phe Phe Asn Ser Glu Ser Gly Glu Arg Phe Tyr Ile
            35                  40                  45
Arg Gly Val Asp Tyr Gln Pro Gly Gly Ser Ser Asn Leu Thr Asp Pro
        50                  55                  60
Leu Ala Asp Ala Ser Val Cys Asp Arg Asp Val Pro Val Leu Lys Asp
65                  70                  75                  80
Leu Gly Ile Asn Thr Val Arg Val Tyr Thr Val Asp Asn Ser Gln Asp
                85                  90                  95
His Ser His Cys Met Lys Leu Leu Gln Glu Asn Gly Ile Tyr Leu Ile
            100                 105                 110
Leu Asp Val Asn Thr Pro Thr Ser Ala Ile Ser Arg Tyr Asp Pro Ala
            115                 120                 125
Cys Ser Tyr Asn Ala Asp Tyr Leu Gln Asn Val Phe Ala Thr Ile Asp
        130                 135                 140
Thr Phe Ala Asp Tyr Asp Asn Val Leu Gly Phe Phe Ala Gly Asn Glu
145                 150                 155                 160
Val Ile Asn Ser Val Asn Thr Thr Asn Thr Ala Thr Tyr Val Lys Ala
                165                 170                 175
Val Val Arg Asp Met Lys Lys Tyr Ile Lys Ala Arg Lys Tyr Arg Gln
            180                 185                 190
Ile Pro Val Gly Tyr Ser Ala Ala Asp Ile Val Ala Asn Arg Gln Leu
        195                 200                 205
Ala Ala Glu Tyr Phe Asn Cys Gly Asp Glu Ala Asp Ala Arg Ile Asp
210                 215                 220
Met Phe Gly Val Asn Asp Tyr Ser Trp Cys Gly Glu Ser Ser Phe Val
225                 230                 235                 240
Val Ser Gly Tyr Ser Thr Lys Met Lys Leu Tyr Gln Asp Tyr Ser Val
                245                 250                 255
Pro Val Phe Leu Ser Glu Phe Gly Cys Asn Gln Val Lys Ser Ser Arg
            260                 265                 270
Pro Phe Thr Glu Ile Glu Ala Ile Tyr Ser Thr Gln Met Ser Ser Val
            275                 280                 285
Phe Ser Gly Gly Leu Val Tyr Glu Tyr Ser Asn Glu Thr Asn Asn Tyr
        290                 295                 300
Gly Leu Val Gln Ile Asp Gly Asp Lys Val Thr Lys Leu Thr Asp Phe
305                 310                 315                 320
Glu Asn Leu Lys Asn Glu Tyr Ser Lys Val Ser Asn Pro Glu Gly Asn
                325                 330                 335
Gly Gly Tyr Ser Thr Ser Asn Asn Tyr Ser Thr Cys Pro Asp Tyr Glu
            340                 345                 350
Lys Gly Val Trp Glu Ala Asn Asn Thr Leu Pro Ala Met Pro Ser Ala
        355                 360                 365
Ala Ser Ala Tyr Phe Thr Ser Gly Ala Gly Ser Pro Met Gly Thr Gly
        370                 375                 380
Ile Ala Thr Gln Gln Ser Cys Asp Ala Lys Asp Asp Asp Glu Glu
385                 390                 395                 400
Asp Asp Asp Thr Ser Ser Ser Ser Ser Ser Ser Ser Ser Ser Ser
                405                 410                 415
```

```
Ser Ala Ser Ser Ser Glu Ser Ser Ser Thr Ser Lys Ala Ser
            420                 425                 430

Ser Ser Ser Pro Ser Ala Ser Glu Thr Ser Leu Leu Lys Ser Ala Ala
            435                 440                 445

Ser Ala Thr Ser Ser Gln Ser Ser Ser Lys Ser Lys Gly Ala Ala
            450                 455                 460

Gly Ile Ile Glu Ile Pro Leu Ile Phe Arg Ala Leu Ala Glu Leu Tyr
465                 470                 475                 480

Asn Leu Val Leu

<210> SEQ ID NO 83
<211> LENGTH: 444
<212> TYPE: PRT
<213> ORGANISM: Saccharomyces sp.

<400> SEQUENCE: 83

Met Gln Leu His Ser Leu Ile Ala Ser Thr Ala Leu Leu Ile Thr Ser
1               5                   10                  15

Ala Leu Ala Ala Thr Ser Ser Ser Ser Ile Pro Ser Ser Cys Thr
            20                  25                  30

Ile Ser Ser His Ala Thr Ala Thr Ala Gln Ser Asp Leu Asp Lys Tyr
        35                  40                  45

Ser Arg Cys Asp Thr Leu Val Gly Asn Leu Thr Ile Gly Gly Gly Leu
50                  55                  60

Lys Thr Gly Ala Leu Ala Asn Val Lys Glu Ile Asn Gly Ser Leu Thr
65                  70                  75                  80

Ile Phe Asn Ala Thr Asn Leu Thr Ser Phe Ala Ala Asp Ser Leu Glu
                85                  90                  95

Ser Ile Thr Asp Ser Leu Asn Leu Gln Ser Leu Thr Ile Leu Thr Ser
            100                 105                 110

Ala Ser Phe Gly Ser Leu Gln Ser Val Asp Ser Ile Lys Leu Ile Thr
        115                 120                 125

Leu Pro Ala Ile Ser Ser Phe Thr Ser Asn Ile Lys Ser Ala Asn Asn
130                 135                 140

Ile Tyr Ile Ser Asp Thr Ser Leu Gln Ser Val Asp Gly Phe Ser Ala
145                 150                 155                 160

Leu Lys Lys Val Asn Val Phe Asn Val Asn Asn Lys Lys Leu Thr
                165                 170                 175

Ser Ile Lys Ser Pro Val Glu Thr Val Ser Asp Ser Leu Gln Phe Ser
            180                 185                 190

Phe Asn Gly Asn Gln Thr Lys Ile Thr Phe Asp Asp Leu Val Trp Ala
        195                 200                 205

Asn Asn Ile Ser Leu Thr Asp Val His Ser Val Ser Phe Ala Asn Leu
210                 215                 220

Gln Lys Ile Asn Ser Ser Leu Gly Phe Ile Asn Asn Ser Ile Ser Ser
225                 230                 235                 240

Leu Asn Phe Thr Lys Leu Asn Thr Ile Gly Gln Thr Phe Ser Ile Val
                245                 250                 255

Ser Asn Asp Tyr Leu Lys Asn Leu Ser Phe Ser Asn Leu Ser Thr Ile
            260                 265                 270

Gly Gly Ala Leu Val Val Ala Asn Asn Thr Gly Leu Gln Lys Ile Gly
        275                 280                 285

Gly Leu Asp Asn Leu Thr Thr Ile Gly Gly Thr Leu Glu Val Val Gly
290                 295                 300
```

```
Asn Phe Thr Ser Leu Asn Leu Asp Ser Leu Lys Ser Val Lys Gly Gly
305                 310                 315                 320

Ala Asp Val Glu Ser Lys Ser Ser Asn Phe Ser Cys Asn Ala Leu Lys
                325                 330                 335

Ala Leu Gln Lys Lys Gly Gly Ile Lys Gly Glu Ser Phe Val Cys Lys
            340                 345                 350

Asn Gly Ala Ser Ser Thr Ser Val Lys Leu Ser Ser Thr Ser Lys Ser
        355                 360                 365

Gln Ser Ser Gln Thr Thr Ala Lys Val Ser Lys Ser Ser Lys Ala
    370                 375                 380

Glu Glu Lys Lys Phe Thr Ser Gly Asp Ile Lys Ala Ala Ser Ala
385                 390                 395                 400

Ser Ser Val Ser Ser Gly Ala Ser Ser Ser Ser Lys Ser Ser
                405                 410                 415

Lys Gly Asn Ala Ala Ile Met Ala Pro Ile Gly Gln Thr Thr Pro Leu
            420                 425                 430

Val Gly Leu Leu Thr Ala Ile Ile Met Ser Ile Met
            435                 440
```

<210> SEQ ID NO 84
<211> LENGTH: 830
<212> TYPE: PRT
<213> ORGANISM: Saccharomyces sp.

<400> SEQUENCE: 84

```
Met Gln Leu Met Arg Leu Ser Asn Leu Ile Ala Ser Ala Ser Leu Leu
1               5                   10                  15

Ser Ala Ala Thr Leu Ala Ala Pro Ala Asn His Glu His Lys Asp Lys
            20                  25                  30

Arg Ala Val Val Thr Thr Thr Val Gln Lys Gln Thr Thr Ile Ile Val
            35                  40                  45

Asn Gly Ala Ala Ser Thr Pro Val Ala Ala Leu Glu Glu Asn Ala Val
    50                  55                  60

Val Asn Ser Ala Pro Ala Ala Ala Thr Ser Thr Thr Ser Ser Ala Ala
65                  70                  75                  80

Ser Val Ala Thr Ala Ala Ala Ser Ser Ser Glu Asn Asn Ser Gln Val
                85                  90                  95

Ser Ala Ala Ala Ser Pro Ala Ser Ser Ser Ala Ala Thr Ser Thr Gln
            100                 105                 110

Ser Ser Ser Ser Ser Gln Ala Ser Ser Ser Ser Ser Gly Glu Asp
        115                 120                 125

Val Ser Ser Phe Ala Ser Gly Val Arg Gly Ile Thr Tyr Thr Pro Tyr
    130                 135                 140

Glu Ser Ser Gly Ala Cys Lys Ser Ala Ser Glu Val Ala Ser Asp Leu
145                 150                 155                 160

Ala Gln Leu Thr Asp Phe Pro Val Ile Arg Leu Tyr Gly Thr Asp Cys
            165                 170                 175

Asn Gln Val Glu Asn Val Phe Lys Ala Lys Ala Ser Asn Gln Lys Val
            180                 185                 190

Phe Leu Gly Ile Tyr Tyr Val Asp Gln Ile Gln Asp Gly Val Asn Thr
        195                 200                 205

Ile Lys Ser Ala Val Glu Ser Tyr Gly Ser Trp Asp Asp Val Thr Thr
    210                 215                 220

Val Ser Ile Gly Asn Glu Leu Val Asn Gly Asn Gln Ala Thr Pro Ser
```

```
            225                 230                 235                 240
        Gln Val Gly Gln Tyr Ile Asp Ser Gly Arg Ser Ala Leu Lys Ala Ala
                        245                 250                 255
        Gly Tyr Thr Gly Pro Val Val Ser Val Asp Thr Phe Ile Ala Val Ile
                        260                 265                 270
        Asn Asn Pro Glu Leu Cys Asp Tyr Ser Asp Tyr Met Ala Val Asn Ala
                        275                 280                 285
        His Ala Tyr Phe Asp Lys Asn Thr Val Ala Gln Asp Ser Gly Lys Trp
                        290                 295                 300
        Leu Leu Glu Gln Ile Gln Arg Val Trp Thr Ala Cys Asp Gly Lys Lys
        305                 310                 315                 320
        Asn Val Val Ile Thr Glu Ser Gly Trp Pro Ser Lys Gly Glu Thr Tyr
                        325                 330                 335
        Gly Val Ala Val Pro Ser Lys Glu Asn Gln Lys Asp Ala Val Ser Ala
                        340                 345                 350
        Ile Thr Ser Ser Cys Gly Ala Asp Thr Phe Leu Phe Thr Ala Phe Asn
                        355                 360                 365
        Asp Tyr Trp Lys Ala Asp Gly Ala Tyr Gly Val Glu Lys Tyr Trp Gly
                        370                 375                 380
        Ile Leu Ser Asn Glu His Ser Leu Ile Ala Ser Thr Ala Leu Leu Ile
        385                 390                 395                 400
        Thr Ser Ala Leu Ala Ala Thr Ser Ser Ser Ser Ile Pro Ser Ser
                        405                 410                 415
        Cys Thr Ile Ser Ser His Ala Thr Ala Thr Gln Ser Asp Leu Asp
                        420                 425                 430
        Lys Tyr Ser Arg Cys Asp Thr Leu Val Gly Asn Leu Thr Ile Gly Gly
                        435                 440                 445
        Gly Leu Lys Thr Gly Ala Leu Ala Asn Val Lys Glu Ile Asn Gly Ser
                        450                 455                 460
        Leu Thr Ile Phe Asn Ala Thr Asn Leu Thr Ser Phe Ala Ala Asp Ser
        465                 470                 475                 480
        Leu Glu Ser Ile Thr Asp Ser Leu Asn Leu Gln Ser Leu Thr Ile Leu
                        485                 490                 495
        Thr Ser Ala Ser Phe Gly Ser Leu Gln Ser Val Asp Ser Ile Lys Leu
                        500                 505                 510
        Ile Thr Leu Pro Ala Ile Ser Ser Phe Thr Ser Asn Ile Lys Ser Ala
                        515                 520                 525
        Asn Asn Ile Tyr Ile Ser Asp Thr Ser Leu Gln Ser Val Asp Gly Phe
                        530                 535                 540
        Ser Ala Leu Lys Lys Val Asn Val Phe Asn Val Asn Asn Lys Lys
        545                 550                 555                 560
        Leu Thr Ser Ile Lys Ser Pro Val Glu Thr Val Ser Asp Ser Leu Gln
                        565                 570                 575
        Phe Ser Phe Asn Gly Asn Gln Thr Lys Ile Thr Phe Asp Asp Leu Val
                        580                 585                 590
        Trp Ala Asn Asn Ile Ser Leu Thr Asp Val His Ser Val Ser Phe Ala
                        595                 600                 605
        Asn Leu Gln Lys Ile Asn Ser Ser Leu Gly Phe Ile Asn Asn Ser Ile
                        610                 615                 620
        Ser Ser Leu Asn Phe Thr Lys Leu Asn Thr Ile Gly Gln Thr Phe Ser
        625                 630                 635                 640
        Ile Val Ser Asn Asp Tyr Leu Lys Asn Leu Ser Phe Ser Asn Leu Ser
                        645                 650                 655
```

Thr Ile Gly Gly Ala Leu Val Ala Asn Asn Thr Gly Leu Gln Lys
            660                 665                 670

Ile Gly Gly Leu Asp Asn Leu Thr Thr Ile Gly Gly Thr Leu Glu Val
    675                 680                 685

Val Gly Asn Phe Thr Ser Leu Asn Leu Asp Ser Leu Lys Ser Val Lys
690                 695                 700

Gly Gly Ala Asp Val Glu Ser Lys Ser Ser Asn Phe Ser Cys Asn Ala
705                 710                 715                 720

Leu Lys Ala Leu Gln Lys Lys Gly Gly Ile Lys Gly Glu Ser Phe Val
                725                 730                 735

Cys Lys Asn Gly Ala Ser Ser Thr Ser Val Lys Leu Ser Ser Thr Ser
            740                 745                 750

Lys Ser Gln Ser Ser Gln Thr Thr Ala Lys Val Ser Lys Ser Ser
                755                 760                 765

Lys Ala Glu Glu Lys Lys Phe Thr Ser Gly Asp Ile Lys Ala Ala Ala
    770                 775                 780

Ser Ala Ser Ser Val Ser Ser Ser Gly Ala Ser Ser Ser Ser Ser Lys
785                 790                 795                 800

Ser Ser Lys Gly Asn Ala Ala Ile Met Ala Pro Ile Gly Gln Thr Thr
                805                 810                 815

Pro Leu Val Gly Leu Leu Thr Ala Ile Ile Met Ser Ile Met
            820                 825                 830

<210> SEQ ID NO 85
<211> LENGTH: 389
<212> TYPE: PRT
<213> ORGANISM: Saccharomyces sp.

<400> SEQUENCE: 85

Met Arg Phe Ser Asn Phe Leu Thr Val Ser Ala Leu Leu Thr Gly Ala
1               5                   10                  15

Leu Gly Ala Pro Ala Val Arg His Lys His Glu Lys Arg Asp Val Val
            20                  25                  30

Thr Ala Thr Val His Ala Gln Val Thr Val Val Ser Gly Asn Ser
            35                  40                  45

Gly Glu Thr Ile Val Pro Val Asn Glu Asn Ala Val Val Ala Thr Thr
    50                  55                  60

Ser Ser Thr Ala Val Ala Ser Gln Ala Thr Thr Ser Thr Leu Glu Pro
65                  70                  75                  80

Thr Thr Ser Ala Asn Val Val Thr Ser Gln Gln Gln Thr Ser Thr Leu
                85                  90                  95

Gln Ser Ser Glu Ala Ala Ser Thr Val Gly Ser Ser Thr Ser Ser Ser
                100                 105                 110

Pro Ser Ser Ser Ser Thr Ser Ser Ala Ser Ser Ala Ser
            115                 120                 125

Ser Ser Ile Ser Ala Ser Gly Ala Lys Gly Ile Thr Tyr Ser Pro Tyr
    130                 135                 140

Asn Asp Asp Gly Ser Cys Lys Ser Thr Ala Gln Val Ala Ser Asp Leu
145                 150                 155                 160

Glu Gln Leu Thr Gly Phe Asp Asn Ile Arg Leu Tyr Gly Val Asp Cys
                165                 170                 175

Ser Gln Val Glu Asn Val Leu Gln Ala Lys Thr Ser Ser Gln Lys Leu
            180                 185                 190

Phe Leu Gly Ile Tyr Tyr Val Asp Lys Ile Gln Asp Ala Val Asp Thr

```
                    195                 200                 205
Ile Lys Ser Ala Val Glu Ser Tyr Gly Ser Trp Asp Asp Ile Thr Thr
210                 215                 220

Val Ser Val Gly Asn Glu Leu Val Asn Gly Gly Ser Ala Thr Thr Thr
225                 230                 235                 240

Gln Val Gly Glu Tyr Val Ser Thr Ala Lys Ser Ala Leu Thr Ser Ala
                    245                 250                 255

Gly Tyr Thr Gly Ser Val Val Ser Val Asp Thr Phe Ile Ala Val Ile
                    260                 265                 270

Asn Asn Pro Asp Leu Cys Asn Tyr Ser Asp Tyr Met Ala Val Asn Ala
                    275                 280                 285

His Ala Tyr Phe Asp Glu Asn Thr Ala Ala Gln Asp Ala Gly Pro Trp
290                 295                 300

Val Leu Glu Gln Ile Glu Arg Val Tyr Thr Ala Cys Gly Gly Lys Lys
305                 310                 315                 320

Asp Val Val Ile Thr Glu Thr Gly Trp Pro Ser Lys Gly Asp Thr Tyr
                    325                 330                 335

Gly Glu Ala Val Pro Ser Lys Ala Asn Gln Glu Ala Ala Ile Ser Ser
                    340                 345                 350

Ile Lys Ser Ser Cys Gly Ser Ser Ala Tyr Leu Phe Thr Ala Phe Asn
                    355                 360                 365

Asp Leu Trp Lys Asp Asp Gly Gln Tyr Gly Val Glu Lys Tyr Trp Gly
370                 375                 380

Ile Leu Ser Ser Asp
385

<210> SEQ ID NO 86
<211> LENGTH: 475
<212> TYPE: PRT
<213> ORGANISM: Saccharomyces sp.

<400> SEQUENCE: 86

Met Lys Phe Ser Thr Ala Val Thr Thr Leu Ile Ser Ser Gly Ala Ile
1               5                   10                  15

Val Ser Ala Leu Pro His Val Asp Val His Gln Glu Asp Ala His Gln
                20                  25                  30

His Lys Arg Ala Val Ala Tyr Lys Tyr Val Tyr Glu Thr Val Val Val
                35                  40                  45

Asp Ser Asp Gly His Thr Val Thr Pro Ala Ala Ser Glu Val Ala Thr
50                  55                  60

Ala Ala Thr Ser Ala Ile Ile Thr Thr Ser Val Leu Ala Pro Thr Ser
65                  70                  75                  80

Ser Ala Ala Ala Gly Ile Ala Ala Ser Ile Ala Val Ser Ser Ala Ala
                85                  90                  95

Leu Ala Lys Asn Glu Lys Ile Ser Asp Ala Ala Ala Ser Ala Thr Ala
                100                 105                 110

Ser Thr Ser Gln Gly Ala Ser Ser Ser Ser Ser Ser Ser Ser Ala Thr
                115                 120                 125

Ser Thr Leu Glu Ser Ser Ser Val Ser Ser Ser Glu Glu Ala Ala
                130                 135                 140

Pro Thr Ser Thr Val Val Ser Thr Ser Ser Ala Thr Gln Ser Ser Ala
145                 150                 155                 160

Ser Ser Ala Thr Lys Ser Ser Ser Ser Thr Ser Pro Ser Thr Ser
                165                 170                 175
```

```
Thr Ser Thr Ser Thr Ser Ser Thr Ser Ser Ser Ser Ser Ser
            180                 185                 190

Ser Ser Ser Ser Ser Ser Gly Ser Gly Ser Ile Tyr Gly Asp Leu
        195                 200                 205

Ala Asp Phe Ser Gly Pro Ser Glu Lys Phe Gln Asp Gly Thr Ile Pro
210                 215                 220

Cys Asp Lys Phe Pro Ser Gly Gln Gly Val Ile Ser Ile Asp Trp Ile
225                 230                 235                 240

Gly Glu Gly Gly Trp Ser Gly Val Glu Asn Thr Asp Thr Ser Thr Gly
                245                 250                 255

Gly Ser Cys Lys Glu Gly Ser Tyr Cys Ser Tyr Ser Cys Gln Pro Gly
                260                 265                 270

Met Ser Lys Thr Gln Trp Pro Ser Asp Gln Pro Ser Asp Gly Arg Ser
            275                 280                 285

Val Gly Gly Leu Leu Cys Lys Asn Gly Tyr Leu Tyr Arg Ser Asn Thr
        290                 295                 300

Asp Ala Asp Tyr Leu Cys Glu Trp Gly Val Glu Ala Ala Tyr Val Val
305                 310                 315                 320

Ser Lys Leu Ser Lys Gly Val Ala Ile Cys Arg Thr Asp Tyr Pro Gly
                325                 330                 335

Thr Glu Asn Met Val Ile Pro Thr Tyr Val Glu Gly Gly Ser Ser Leu
            340                 345                 350

Pro Leu Thr Val Val Asp Gln Asp Thr Tyr Phe Thr Trp Glu Gly Lys
        355                 360                 365

Lys Thr Ser Ala Gln Tyr Tyr Val Asn Asn Ala Gly Val Ser Val Glu
370                 375                 380

Asp Gly Cys Ile Trp Gly Thr Gly Ser Gly Ile Gly Asn Trp Ala
385                 390                 395                 400

Pro Leu Asn Phe Gly Ala Gly Ser Thr Gly Gly Val Thr Tyr Leu Ser
        405                 410                 415

Leu Ile Pro Asn Pro Asn Asn Ser Asp Ala Leu Asn Tyr Asn Val Lys
            420                 425                 430

Ile Val Ala Ala Asp Asp Ser Ser Asn Val Ile Gly Glu Cys Val Tyr
        435                 440                 445

Glu Asn Gly Glu Phe Ser Gly Gly Ala Asp Gly Cys Thr Val Ser Val
450                 455                 460

Thr Ser Gly Lys Ala His Phe Val Leu Tyr Asn
465                 470                 475

<210> SEQ ID NO 87
<211> LENGTH: 365
<212> TYPE: PRT
<213> ORGANISM: Saccharomyces sp.

<400> SEQUENCE: 87

Met Lys Leu Ser Ala Leu Leu Ala Leu Ser Ala Ser Thr Ala Val Leu
1               5                   10                  15

Ala Ala Pro Ala Val His His Ser Asp Asn His His His Asn Asp Lys
                20                  25                  30

Arg Ala Val Val Thr Val Thr Gln Tyr Val Asn Ala Asp Gly Ala Val
            35                  40                  45

Val Ile Pro Ala Ala Thr Thr Ala Ser Ala Ala Ala Asp Gly Lys
        50                  55                  60

Val Glu Ser Val Ala Ala Ala Thr Thr Leu Ser Ser Thr Ala Ala
65                  70                  75                  80
```

```
Ala Ala Thr Thr Ser Ala Ala Ala Ser Ser Ser Ser Ser Ser
                85                  90                  95

Ser Ser Ser Ser Ser Ser Val Gly Ser Gly Asp Phe Glu Asp Gly
            100                 105                 110

Thr Ile Ser Cys Ser Asp Phe Pro Ser Gly Gln Gly Ala Val Ser Leu
        115                 120                 125

Asp Trp Leu Gly Leu Gly Gly Trp Ala Ser Ile Met Asp Met Asn Gly
    130                 135                 140

Asn Thr Ala Thr Ser Cys Gln Asp Gly Tyr Tyr Cys Ser Tyr Ala Cys
145                 150                 155                 160

Ser Pro Gly Tyr Ala Lys Thr Gln Trp Pro Ser Glu Gln Pro Ser Asp
                165                 170                 175

Gly Arg Ser Val Gly Gly Leu Tyr Cys Lys Asn Gly Lys Leu Tyr Arg
            180                 185                 190

Ser Asn Thr Asp Thr Asn Ser Leu Cys Val Glu Gly Gln Gly Ser Ala
        195                 200                 205

Gln Ala Val Asn Lys Val Ser Gly Ser Ile Ala Ile Cys Gly Thr Asp
    210                 215                 220

Tyr Pro Gly Ser Glu Asn Met Val Val Pro Thr Val Gly Ala Gly
225                 230                 235                 240

Ser Ser Gln Pro Ile Asn Val Ile Lys Glu Asp Ser Tyr Tyr Gln Trp
                245                 250                 255

Gln Gly Lys Lys Thr Ser Ala Gln Tyr Tyr Val Asn Asn Ala Gly Val
            260                 265                 270

Ser Val Glu Asp Gly Cys Ile Trp Gly Thr Gly Ser Gly Val Gly
        275                 280                 285

Asn Trp Ala Pro Val Val Leu Gly Ala Gly Tyr Thr Asp Gly Ile Thr
    290                 295                 300

Tyr Leu Ser Ile Ile Pro Asn Pro Asn Asn Lys Glu Ala Pro Asn Phe
305                 310                 315                 320

Asn Ile Lys Ile Val Ala Thr Asp Gly Ser Thr Val Asn Gly Ala Cys
                325                 330                 335

Ser Tyr Glu Asn Gly Val Tyr Ser Gly Ser Gly Ser Asp Gly Cys Thr
            340                 345                 350

Val Ser Val Thr Ser Gly Ser Ala Asn Phe Val Phe Tyr
        355                 360                 365

<210> SEQ ID NO 88
<211> LENGTH: 719
<212> TYPE: PRT
<213> ORGANISM: Saccharomyces sp.

<400> SEQUENCE: 88

Met Lys Phe Gln Val Val Leu Ser Ala Leu Leu Ala Cys Ser Ser Ala
1               5                   10                  15

Val Val Ala Ser Pro Ile Glu Asn Leu Phe Lys Tyr Arg Ala Val Lys
            20                  25                  30

Ala Ser His Ser Lys Asn Ile Asn Ser Thr Leu Pro Ala Trp Asn Gly
        35                  40                  45

Ser Asn Ser Ser Asn Val Thr Tyr Ala Asn Gly Thr Asn Ser Thr Thr
    50                  55                  60

Asn Thr Thr Thr Ala Glu Ser Ser Gln Leu Gln Ile Ile Val Thr Gly
65                  70                  75                  80

Gly Gln Val Pro Ile Thr Asn Ser Ser Leu Thr His Thr Asn Tyr Thr
```

```
                    85                  90                  95
Arg Leu Phe Asn Ser Ser Ala Leu Asn Ile Thr Glu Leu Tyr Asn
                100                 105                 110

Val Ala Arg Val Val Asn Glu Thr Ile Gln Asp Lys Ser Ser Ala Gly
            115                 120                 125

Ala Val Val Ala Asn Ala Lys Ser Leu Glu Ala Val Ser Phe Phe
    130                 135                 140

Phe Ser Ile Ile Phe Asp Thr Glu Lys Pro Ile Val Val Thr Glu Asp
145                 150                 155                 160

Ser Ala Tyr Ala Ile Pro Val Ala Asn Asn Lys Asn Ala Thr Lys Arg
                165                 170                 175

Gly Val Leu Ser Val Thr Ser Asp Lys Leu Val Tyr Ser Gly Val Phe
            180                 185                 190

Thr Pro Pro Thr Ala Cys Ser Tyr Gly Ala Gly Leu Pro Val Ala Ile
                195                 200                 205

Val Asp Asp Gln Asp Glu Val Lys Trp Phe Phe Asp Ala Ser Lys Pro
    210                 215                 220

Thr Leu Ile Ser Ser Asp Ser Ile Ile Arg Lys Glu Tyr Ser Asn Phe
225                 230                 235                 240

Thr Thr Pro Tyr Gly Leu Leu Glu Asn Gly Val Pro Ile Val Pro Ile
                245                 250                 255

Val Tyr Asp Gly Gly Tyr Ser Ser Leu Ile Asp Ser Leu Ser Ser
        260                 265                 270

Ala Val Gln Gly Leu Val Val Ser Ser Gly Ser Thr Asn Ser Thr
        275                 280                 285

Ser Ser Thr Ile Glu Ser Thr Glu Ile Pro Val Val Tyr Ala Gln Ala
290                 295                 300

Asn Thr Pro Leu Asn Phe Ile Asp Asn Lys Asp Val Pro Lys Asn Ala
305                 310                 315                 320

Val Gly Ala Gly Tyr Leu Ser Pro Ile Lys Ala Gln Ile Leu Leu Ser
                325                 330                 335

Ile Ala Ala Val Asn Gly Val Thr Ser Lys Ser Ala Leu Glu Ser Ile
            340                 345                 350

Phe Pro Met Lys Leu Ser Ala Leu Leu Ala Leu Ser Ala Ser Thr Ala
        355                 360                 365

Val Leu Ala Ala Pro Ala Val His His Ser Asp Asn His His His Asn
    370                 375                 380

Asp Lys Arg Ala Val Thr Val Thr Gln Tyr Val Asn Ala Asp Gly
385                 390                 395                 400

Ala Val Val Ile Pro Ala Ala Thr Thr Ala Thr Ser Ala Ala Ala Asp
                405                 410                 415

Gly Lys Val Glu Ser Val Ala Ala Thr Thr Thr Leu Ser Ser Thr
        420                 425                 430

Ala Ala Ala Ala Thr Thr Ser Ala Ala Ser Ser Ser Ser Ser Ser
    435                 440                 445

Ser Ser Ser Ser Ser Ser Ser Ser Val Gly Ser Gly Asp Phe Glu
    450                 455                 460

Asp Gly Thr Ile Ser Cys Ser Asp Phe Pro Ser Gly Gln Gly Ala Val
465                 470                 475                 480

Ser Leu Asp Trp Leu Gly Leu Gly Gly Trp Ala Ser Ile Met Asp Met
                485                 490                 495

Asn Gly Asn Thr Ala Thr Ser Cys Gln Asp Gly Tyr Tyr Cys Ser Tyr
            500                 505                 510
```

```
Ala Cys Ser Pro Gly Tyr Ala Lys Thr Gln Trp Pro Ser Glu Gln Pro
        515                 520                 525

Ser Asp Gly Arg Ser Val Gly Gly Leu Tyr Cys Lys Asn Gly Lys Leu
    530                 535                 540

Tyr Arg Ser Asn Thr Asp Thr Asn Ser Leu Cys Val Glu Gly Gln Gly
545                 550                 555                 560

Ser Ala Gln Ala Val Asn Lys Val Ser Gly Ile Ala Ile Cys Gly
                565                 570                 575

Thr Asp Tyr Pro Gly Ser Glu Asn Met Val Pro Thr Val Val Gly
                580                 585                 590

Ala Gly Ser Ser Gln Pro Ile Asn Val Ile Lys Glu Asp Ser Tyr Tyr
        595                 600                 605

Gln Trp Gln Gly Lys Lys Thr Ser Ala Gln Tyr Tyr Val Asn Asn Ala
    610                 615                 620

Gly Val Ser Val Glu Asp Gly Cys Ile Trp Gly Thr Glu Gly Ser Gly
625                 630                 635                 640

Val Gly Asn Trp Ala Pro Val Leu Gly Ala Gly Tyr Thr Asp Gly
                645                 650                 655

Ile Thr Tyr Leu Ser Ile Ile Pro Asn Pro Asn Asn Lys Glu Ala Pro
                660                 665                 670

Asn Phe Asn Ile Lys Ile Val Ala Thr Asp Gly Ser Thr Val Asn Gly
        675                 680                 685

Ala Cys Ser Tyr Glu Asn Gly Val Tyr Ser Gly Ser Gly Ser Asp Gly
        690                 695                 700

Cys Thr Val Ser Val Thr Ser Gly Ser Ala Asn Phe Val Phe Tyr
705                 710                 715

<210> SEQ ID NO 89
<211> LENGTH: 569
<212> TYPE: PRT
<213> ORGANISM: Saccharomyces sp.

<400> SEQUENCE: 89

Met Lys Leu Lys Thr Val Arg Ser Ala Val Leu Ser Ser Leu Phe Ala
1               5                   10                  15

Ser Gln Val Leu Gly Lys Ile Ile Pro Ala Ala Asn Lys Arg Asp Asp
            20                  25                  30

Asp Ser Asn Ser Lys Phe Val Lys Leu Pro Phe His Lys Leu Tyr Gly
        35                  40                  45

Asp Ser Leu Glu Asn Val Gly Ser Asp Lys Lys Pro Glu Val Arg Leu
    50                  55                  60

Leu Lys Arg Ala Asp Gly Tyr Glu Glu Ile Ile Ile Thr Asn Gln Gln
65                  70                  75                  80

Ser Phe Tyr Ser Val Asp Leu Glu Val Gly Thr Pro Pro Gln Asn Val
                85                  90                  95

Thr Val Leu Val Asp Thr Gly Ser Ser Asp Leu Trp Ile Met Gly Ser
            100                 105                 110

Asp Asn Pro Tyr Cys Ser Ser Asn Ser Met Gly Ser Ser Arg Arg Arg
        115                 120                 125

Val Ile Asp Lys Arg Asp Asp Ser Ser Gly Gly Ser Leu Ile Asn
    130                 135                 140

Asp Ile Asn Pro Phe Gly Trp Leu Thr Gly Thr Gly Ser Ala Ile Gly
145                 150                 155                 160

Pro Thr Ala Thr Gly Leu Gly Gly Gly Ser Gly Thr Ala Thr Gln Ser
```

-continued

```
                165                 170                 175
Val Pro Ala Ser Glu Ala Thr Met Asp Cys Gln Gln Tyr Gly Thr Phe
                180                 185                 190

Ser Thr Ser Gly Ser Ser Thr Phe Arg Ser Asn Asn Thr Tyr Phe Ser
                195                 200                 205

Ile Ser Tyr Gly Asp Gly Thr Phe Ala Ser Gly Thr Phe Gly Thr Asp
            210                 215                 220

Val Leu Asp Leu Ser Asp Leu Asn Val Thr Gly Leu Ser Phe Ala Val
225                 230                 235                 240

Ala Asn Glu Thr Asn Ser Thr Met Gly Val Leu Gly Ile Gly Leu Pro
                245                 250                 255

Glu Leu Glu Val Thr Tyr Ser Gly Ser Thr Ala Ser His Ser Gly Lys
                260                 265                 270

Ala Tyr Lys Tyr Asp Asn Phe Pro Ile Val Leu Lys Asn Ser Gly Ala
                275                 280                 285

Ile Lys Ser Asn Thr Tyr Ser Leu Tyr Leu Asn Asp Ser Asp Ala Met
            290                 295                 300

His Gly Thr Ile Leu Phe Gly Ala Val Asp His Ser Lys Tyr Thr Gly
305                 310                 315                 320

Thr Leu Tyr Thr Ile Pro Ile Val Asn Thr Leu Ser Ala Ser Gly Phe
                325                 330                 335

Ser Ser Pro Ile Gln Phe Asp Val Thr Ile Asn Gly Ile Gly Ile Ser
                340                 345                 350

Asp Ser Gly Ser Ser Asn Lys Thr Leu Thr Thr Thr Lys Ile Pro Ala
            355                 360                 365

Leu Leu Asp Ser Gly Thr Thr Leu Thr Tyr Leu Pro Gln Thr Val Val
            370                 375                 380

Ser Met Ile Ala Thr Glu Leu Gly Ala Gln Tyr Ser Ser Arg Ile Gly
385                 390                 395                 400

Tyr Tyr Val Leu Asp Cys Pro Ser Asp Asp Ser Met Glu Ile Val Phe
                405                 410                 415

Asp Phe Gly Gly Phe His Ile Asn Ala Pro Leu Ser Ser Phe Ile Leu
                420                 425                 430

Ser Thr Gly Thr Thr Cys Leu Leu Gly Ile Ile Pro Thr Ser Asp Asp
            435                 440                 445

Thr Gly Thr Ile Leu Gly Asp Ser Phe Leu Thr Asn Ala Tyr Val Val
            450                 455                 460

Tyr Asp Leu Glu Asn Leu Glu Ile Ser Met Ala Gln Ala Arg Tyr Asn
465                 470                 475                 480

Thr Thr Ser Glu Asn Ile Glu Ile Ile Thr Ser Ser Val Pro Ser Ala
                485                 490                 495

Val Lys Ala Pro Gly Tyr Thr Asn Thr Trp Ser Thr Ser Ala Ser Ile
                500                 505                 510

Val Thr Gly Gly Asn Ile Phe Thr Val Asn Ser Ser Gln Thr Ala Ser
            515                 520                 525

Phe Ser Gly Asn Leu Thr Thr Ser Thr Ala Ser Ala Thr Ser Thr Ser
            530                 535                 540

Ser Lys Arg Asn Val Gly Asp His Ile Val Pro Ser Leu Pro Leu Thr
545                 550                 555                 560

Leu Ile Ser Leu Leu Phe Ala Phe Ile
                565
```

<210> SEQ ID NO 90

<211> LENGTH: 249
<212> TYPE: PRT
<213> ORGANISM: Saccharomyces sp.

<400> SEQUENCE: 90

```
Met Lys Phe Ser Ser Gly Lys Ser Ile Ile Phe Ala Thr Ile Ala Ser
1               5                   10                  15

Leu Ala Leu Ser Ala Pro Val Thr Tyr Asp Thr Asn Ser Thr Ala Glu
                20                  25                  30

Leu Gln Ser Pro Ser Ser Gln Glu Ile Leu Gly Trp Ser His Ala Thr
            35                  40                  45

Phe Pro Thr Ile Tyr Gln Thr Cys Asn Glu Thr Asn Ala Arg Met Leu
        50                  55                  60

Asn Ala Ala Phe Lys Asp Thr Ala Glu Ile Thr Ala Tyr Gly Lys Asp
65                  70                  75                  80

Arg Leu Leu Asn Tyr Gly Val Asp Asp Val Tyr Tyr Lys Arg Trp Phe
                85                  90                  95

Gly Asn Gly Ser Ile Phe Thr Val Met Gly Val Phe Glu Gln Leu Met
                100                 105                 110

Glu Ala Ser Lys Gly Ala Met Leu Met Arg Cys Asp Asp Ile Asp Gly
            115                 120                 125

Leu Cys Ala Ala Asn Pro Asn Tyr Tyr Ala Gly His His Arg Gln Ser
        130                 135                 140

Ala Pro Ala Glu Thr Val Ile Cys Asp Tyr Phe Tyr Thr Ser Lys Lys
145                 150                 155                 160

Pro Leu Ser Thr Ile Cys Phe Glu Gly Thr Ile Val Asp Val Gly Pro
                165                 170                 175

Lys His Tyr Ala Gly Ile Asp Met Leu His Arg Tyr Leu His Val Pro
                180                 185                 190

Thr Met Ser Met Asp Gly Tyr Val Gly Glu Tyr Ala Glu Thr Leu Glu
            195                 200                 205

Glu Val Val Asp Tyr Thr Gln Asn Asn Ala Thr Tyr Ala Val Arg Asn
        210                 215                 220

Thr Asp Asn Tyr Leu Tyr Tyr Leu Ala Asp Val Tyr Ser Ala Ser Val
225                 230                 235                 240

Ile Pro Gly Gly Cys Leu Gly Asn Leu
                245
```

<210> SEQ ID NO 91
<211> LENGTH: 13
<212> TYPE: PRT
<213> ORGANISM: Artificial Sequence
<220> FEATURE:
<223> OTHER INFORMATION: linker peptide

<400> SEQUENCE: 91

```
Ala Ala Ser Ala Ser Ala Gly Leu Ala Leu Asp Lys Arg
1               5                   10
```